US012751955B2

(12) United States Patent
Gomi et al.

(10) Patent No.: US 12,751,955 B2
(45) Date of Patent: Oct. 6, 2026

(54) FORMULATION FOR ORAL ADMINISTRATION, COMPRISING TRIAZINE DERIVATIVE

(71) Applicant: Shionogi & Co., Ltd., Osaka (JP)

(72) Inventors: Masato Gomi, Osaka (JP); Kensuke Horiuchi, Osaka (JP); Masayuki Morimoto, Osaka (JP); Keisuke Takagaki, Osaka (JP)

(73) Assignee: SHIONOGI & CO., LTD., Osaka (JP)

( * ) Notice: Subject to any disclaimer, the term of this patent is extended or adjusted under 35 U.S.C. 154(b) by 462 days.

(21) Appl. No.: 18/277,445

(22) PCT Filed: Nov. 22, 2022

(86) PCT No.: PCT/JP2022/043092
§ 371 (c)(1),
(2) Date: Aug. 16, 2023

(87) PCT Pub. No.: WO2023/027198
PCT Pub. Date: Mar. 2, 2023

(65) Prior Publication Data

US 2024/0148741 A1 May 9, 2024

(30) Foreign Application Priority Data

| | | |
|---|---|---|
| Nov. 24, 2021 | (JP) | 2021-189932 |
| Nov. 26, 2021 | (JP) | 2021-191635 |
| Jan. 19, 2022 | (JP) | 2022-006725 |
| Jan. 28, 2022 | (JP) | 2022-012386 |
| Feb. 7, 2022 | (JP) | 2022-017132 |
| Feb. 25, 2022 | (JP) | 2022-027629 |
| Mar. 23, 2022 | (JP) | 2022-046304 |
| Sep. 8, 2022 | (JP) | 2022-142767 |
| Sep. 21, 2022 | (CN) | 202211151791.9 |

(51) Int. Cl.

| | |
|---|---|
| ***A01N 43/00*** | (2006.01) |
| ***A01N 43/46*** | (2006.01) |
| ***A61K 9/16*** | (2006.01) |
| ***A61K 9/20*** | (2006.01) |
| ***A61K 31/53*** | (2006.01) |
| ***A61K 31/55*** | (2006.01) |

(52) U.S. Cl.
CPC ............ *A61K 31/53* (2013.01); *A61K 9/1623* (2013.01); *A61K 9/1652* (2013.01); *A61K 9/2018* (2013.01); *A61K 9/2054* (2013.01)

(58) Field of Classification Search
None
See application file for complete search history.

(56) References Cited

U.S. PATENT DOCUMENTS

| | | | |
|---|---|---|---|
| 11,655,240 | B1 | 5/2023 | Wei et al. |
| 2023/0128162 | A1 | 4/2023 | Tachibana et al. |
| 2023/0212154 | A1 | 7/2023 | Tachibana et al. |

FOREIGN PATENT DOCUMENTS

| | | |
|---|---|---|
| CN | 113620888 | 11/2021 |
| CN | 113666914 | 11/2021 |
| CN | 113735838 | 12/2021 |
| CN | 113773300 | 12/2021 |
| CN | 113801097 | 12/2021 |
| CN | 114591304 | 6/2022 |
| CN | 114716417 | 7/2022 |
| CN | 114948969 | 8/2022 |
| CN | 115252619 | 11/2022 |
| EP | 2 399 910 | 12/2011 |
| EP | 2 604 595 | 6/2013 |
| EP | 3 009 432 | 4/2016 |
| WO | 2010/092966 | 8/2010 |
| WO | 2012/009258 | 1/2012 |
| WO | 2012/020749 | 2/2012 |
| WO | 2013/089212 | 6/2013 |
| WO | 2014/200078 | 12/2014 |
| WO | 2021/205298 | 10/2021 |
| WO | 2021/250648 | 12/2021 |
| WO | 2022/138988 | 6/2022 |

OTHER PUBLICATIONS

International Preliminary Report on Patentability issued May 2, 2024 in International (PCT) Application No. PCT/JP2022/043092.
Extended European Search Report issued Dec. 18, 2024 in European Patent Application No. 22861484.8.
COVID-19 Dashboard by the Center for Systems Science and Engineering at Johns Hopkins University, (Sep. 21, 2022).
Neeltge van Doremalen et al., "Aerosol and Surface Stability of SARS-CoV-2 as Compared with SARS-CoV-1", The New England Journal of Medicine, vol. 382, pp. 1564-1567, 2020.
Report of the WHO-China Joint Mission on Coronavirus Disease 2019 (COVID-19), Feb. 16-24, 2020, pp. 1-40.
Kanchan Anand et al., "Coronavirus Main Proteinase ($3CL^{pro}$) Structure: Basis for Design of Anti-SARS Drugs", Science, 2003, vol. 300, pp. 1763-1767, Jun. 13, 2003.
Maren de Vries et al., "A Comparative Analysis of SARS-CoV-2 Antivirals Characterizes $3CL^{pro}$ Inhibitor PF-00835231 as a Potential New Treatment for COVID-19", Journal of Virology, vol. 95, Issue 10, e01819-20, 2021, pp. 1-22.
Chunlong Ma et al., "Boceprevir, GC-376, and calpain inhibitors II, XII inhibit SARS-CoV-2 viral replication by targeting the viral main protease", Cell Research, 2020, vol. 30, pp. 678-692.
Linlin Zhang et al., "Crystal structure of SARS-CoV-2 main protease provides a basis for design of improved α-ketoamide inhibitors", Science, 2020, vol. 368, pp. 409-412.

(Continued)

*Primary Examiner* — Layla Soroush
(74) *Attorney, Agent, or Firm* — Wenderoth, Lind & Ponack, L.L.P.

(57) ABSTRACT

The present invention provides a formulation for oral administration, comprising a triazine derivative having virus proliferation inhibitory action.

16 Claims, 27 Drawing Sheets

Specification includes a Sequence Listing.

(56) References Cited

OTHER PUBLICATIONS

Chun-Hui Zhang et al., "Potent Noncovalent Inhibitors of the Main Protease of SARS-CoV-2 from Molecular Sculpting of the Drug Perampanel Guided by Free Energy Perturbation Calculations", ACS Central Science, 2021, vol. 7, No. 3, pp. 467-475.
G. Atassi et al., "Preclinical evaluation of the anti tumor activity of new epoxyde derivatives", Cancer Treatment Reviews, 1984, 11 Suppl. A:99-110, Abstract.
Atassi, G et al., "Preclinical evaluation of antitumor activity of new epoxide derivates", Contributions to Oncology, 1984, vol. 18, pp. 221-234, Abstract.
Fischer, H et al., "Investigation of the antitumor activity of new epoxide derivatives. Part II: N-Glycidylated oxo-nitrogen heterocycles", Arzneimittel-Forschung, 1984, vol. 34, Iss. 6, pp. 663-668, Abstract.
Dafydd Owen, "Oral inhibitors of the SARS-CoV-2 main protease for the treatment of COVID-19", 261st Am Chem Soc (ACS) Natl Meet, Apr. 5, 2021 / Apr. 16, 2021 Virtual, N/A, Abst 243.
Dafydd R. Owen et al., "An oral SARS-CoV-2 Mpro inhibitor clinical candidate for the treatment of COVID-19", Science, 2021, vol. 374, pp. 1586-1593.
Pfizer Press Release, Nov. 5, 2021, "Pfizer's Novel COVID-19 Oral Antiviral Treatment Candidate Reduced Risk of Hospitalization or Death by 89% in Interim Analysis of Phase 2/3 EPIC-HR Study", pp. 1-11.
AIMECS 2021, AFMC International Medicinal Chemistry Symposium 2021, Online Symposium, Nov. 29, 2021-Dec. 2, 2021, pp. 1-12 and pp. 1-18.
Yuto Unoh et al., "Discovery of S-217622, a Non-Covalent Oral SARS-CoV-2 3CL Protease Inhibitor Clinical Candidate for Treating COVID-19", bioRxiv, Jan. 26, 2022, pp. 1-52, https://doi.org/10.1101/2022.01.26.477782.
Yuto Unoh et al., "Discovery of S-217622, a Noncovalent Oral SARS-CoV-2 3CL Protease Inhibitor Clinical Candidate for Treating COVID-19", Journal of Medicinal Chemistry, vol. 65, pp. 6499-6512, 2022.
Olujide O. Olubiyi et al., "High Throughput Virtual Screening to Discover Inhibitors of the Main Protease of the Coronavirus SARS-CoV-2", Molecules, vol. 25, 3193, pp. 1-20, 2020.
Kenichi Akaji et al., "Design and Evaluation of Anti-SARS-Coronavirus Agents Based on Molecular Interactions with the Viral Protease", Molecules, Vo. 25, 3920, pp. 1-19, 2020.
Yuzhi Liu et al., "The development of Coronavirus 3C-Like protease ($3CL^{pro}$) inhibitors from 2010 to 2020", European Journal of Medicinal Chemistry, vol. 206, 112711, pp. 1-18, 2020.
Extended European Search Report issued Dec. 1, 2025 in European Patent Application No. 23714052.0.

Fig. 2

| No. | 2θ(°) | Intensity | No. | 2θ(°) | Intensity | No. | 2θ(°) | Intensity | No. | 2θ(°) | Intensity |
|---|---|---|---|---|---|---|---|---|---|---|---|
| 1 | 3.4200 | 210.3583 | 17 | 15.1600 | 194.0755 | 33 | 21.4600 | 709.0836 | 49 | 27.1400 | 339.1359 |
| 2 | 5.3800 | 180.6752 | 18 | 15.3600 | 160.1640 | 34 | 21.7800 | 375.1318 | 50 | 27.6200 | 216.6629 |
| 3 | 5.6600 | 214.3410 | 19 | 15.6000 | 181.4276 | 35 | 21.9400 | 487.5561 | 51 | 27.7200 | 256.8279 |
| 4 | 5.9400 | 265.2505 | 20 | 16.3400 | 243.9242 | 36 | 22.0600 | 429.3932 | 52 | 27.9200 | 242.5821 |
| 5 | 7.7600 | 513.7367 | 21 | 16.5400 | 168.9487 | 37 | 22.6200 | 749.8068 | 53 | 28.1600 | 317.5602 |
| 6 | 8.8600 | 173.9452 | 22 | 17.0800 | 315.4594 | 38 | 23.1000 | 491.4590 | 54 | 28.2600 | 310.9375 |
| 7 | 9.4800 | 621.8839 | 23 | 17.6200 | 202.2376 | 39 | 23.2000 | 452.7953 | 55 | 28.4400 | 211.6360 |
| 8 | 10.1000 | 777.2543 | 24 | 18.0600 | 643.2245 | 40 | 23.5000 | 2643.1279 | 56 | 29.1000 | 219.5811 |
| 9 | 10.9000 | 1684.4740 | 25 | 18.3000 | 221.2361 | 41 | 23.7400 | 1280.4906 | 57 | 29.6400 | 393.1694 |
| 10 | 11.4800 | 775.3323 | 26 | 18.6200 | 961.6690 | 42 | 24.6400 | 5047.3081 | 58 | 30.1000 | 181.8493 |
| 11 | 11.9200 | 379.1448 | 27 | 19.0800 | 766.5743 | 43 | 25.4000 | 587.0492 | 59 | 30.1600 | 172.2840 |
| 12 | 12.3000 | 486.3645 | 28 | 19.5000 | 383.6412 | 44 | 25.6400 | 407.2333 | 60 | 30.8000 | 280.2609 |
| 13 | 13.3000 | 395.4130 | 29 | 19.8400 | 258.1814 | 45 | 25.7000 | 379.0891 | 61 | 31.1200 | 468.9870 |
| 14 | 13.7800 | 452.2804 | 30 | 20.2800 | 419.3952 | 46 | 25.9000 | 328.3577 | 62 | 31.3200 | 296.4213 |
| 15 | 14.7000 | 569.5134 | 31 | 20.5600 | 211.8717 | 47 | 26.4000 | 187.6130 | 63 | 31.7200 | 205.5943 |
| 16 | 14.9200 | 178.2413 | 32 | 20.8400 | 603.8334 | 48 | 27.0400 | 355.1769 | | | |

Peak table

Detector A Ch1 255nm

| Peak # | Retention time | Area | Height | Area % | Number of theoretical plates (USP | Symmetry factor | S/N | Resolution (USP) |
|---|---|---|---|---|---|---|---|---|
| 1 | 8.185 | 47315 | 6866 | 0.677 | 30628 | 1.278 | 15.40 | — |
| 2 | 9.575 | 9230 | 1001 | 0.132 | 35477 | — | 2.25 | 7.122 |
| 3 | 9.917 | 1752 | 310 | 0.025 | 48518 | — | 0.69 | 1.784 |
| 4 | 10.138 | 9208 | 1485 | 0.132 | 53498 | 1.280 | 3.33 | 1.243 |
| 5 | 10.437 | 1588 | 244 | 0.023 | 50407 | 1.083 | 0.55 | 1.659 |
| 6 | 11.363 | 1356 | 284 | 0.019 | 90284 | 1.191 | 0.59 | 5.491 |
| 7 | 12.006 | 2079 | 215 | 0.030 | 25217 | — | 0.48 | 2.834 |
| 8 | 12.427 | 3378 | 324 | 0.048 | 39961 | — | 0.73 | 1.527 |
| 9 | 12.960 | 6635569 | 909273 | 94.918 | 68225 | 1.335 | 2040.02 | 2.386 |
| 10 | 13.968 | 2381 | 249 | 0.034 | 37385 | — | 0.56 | 4.137 |
| 11 | 14.295 | 264769 | 33412 | 3.787 | 71942 | 1.272 | 74.96 | 1.302 |
| 12 | 15.173 | 2880 | 342 | 0.041 | 72263 | — | 0.77 | 3.998 |
| 13 | 15.457 | 7632 | 827 | 0.109 | 71854 | 1.591 | 1.85 | 1.246 |
| 14 | 19.083 | 1740 | 210 | 0.025 | 108260 | 1.201 | 0.47 | 15.714 |
| Total | | 6990858 | 955020 | 100.000 | | | | |

Peak table

Detector A Ch1 255nm

| Peak # | Retention time | Area | Height | Area % | Number of theoretical plates (USP | Symmetry factor | S/N | Resolution (USP) |
|---|---|---|---|---|---|---|---|---|
| 1 | 8.194 | 25361 | 3786 | 0.342 | 31117 | 1.250 | 9.56 | --- |
| 2 | 8.875 | 1519 | 201 | 0.021 | 34906 | --- | 0.51 | 3.623 |
| 3 | 9.286 | 1811 | 180 | 0.024 | 21890 | --- | 0.46 | 1.861 |
| 4 | 9.472 | 2404 | 202 | 0.032 | 15531 | --- | 0.51 | 0.671 |
| 5 | 10.012 | 56041 | 4163 | 0.756 | 12436 | 1.147 | 10.51 | 1.630 |
| 6 | 10.418 | 1159 | 216 | 0.016 | 70797 | 1.298 | 0.54 | 1.573 |
| 7 | 12.966 | 7315438 | 985267 | 98.741 | 68259 | 1.339 | 2487.32 | 14.351 |
| 8 | 14.122 | 4990 | 463 | 0.067 | 50369 | 1.684 | 1.17 | 5.135 |
| Total | | 7408723 | 994478 | 100.000 | | | | |

Fig. 10

| No. | 2θ(°) |
|---|---|
| 1 | 5.956 |
| 2 | 7.738 |
| 3 | 9.451 |
| 4 | 10.0454 |
| 5 | 10.8724 |
| 6 | 11.426 |
| 7 | 11.919 |
| 8 | 12.266 |
| 9 | 13.3038 |
| 10 | 13.780 |
| 11 | 14.641 |
| 12 | 15.106 |
| 13 | 15.59582 |
| 14 | 16.25 |
| 15 | 17.037 |
| 16 | 17.46877 |
| 17 | 17.918 |
| 18 | 18.574 |
| 19 | 19.038 |
| 20 | 19.441 |
| 21 | 19.785 |
| 22 | 20.199 |
| 23 | 20.77 |
| 24 | 21.28 |
| 25 | 21.63940 |
| 26 | 21.868 |
| 27 | 22.553 |
| 28 | 23.012 |
| 29 | 23.384 |
| 30 | 23.66469 |
| 31 | 23.69 |
| 32 | 23.98114 |
| 33 | 24.558 |
| 34 | 25.249 |
| 35 | 25.630 |
| 36 | 26.893 |
| 37 | 27.66 |
| 38 | 28.096 |
| 39 | 28.55872 |
| 40 | 28.984 |
| 41 | 29.49 |
| 42 | 30.04 |
| 43 | 30.51158 |
| 44 | 30.909 |
| 45 | 31.941 |
| 46 | 32.50 |
| 47 | 33.122 |
| 48 | 33.439 |
| 49 | 33.883 |
| 50 | 34.700 |
| 51 | 34.871 |

<PEAK TABLE>

| PEAK # | RETENTION TIME | AREA | HEIGHT | AREA % | NUMBER OF THEORETICAL PLATES (JP) | SYMMETRY FACTOR | S/N | RESOLUTION (JP) |
|---|---|---|---|---|---|---|---|---|
| 1 | 3.521 | 1696 | 266 | 0.022 | 7920 | 1.307 | 3.69 | -- |
| 2 | 5.350 | 4895 | 160 | 0.063 | -- | -- | 2.21 | -- |
| 3 | 5.835 | 10954 | 1380 | 0.141 | 14432 | -- | 19.10 | -- |
| 4 | 6.785 | 3050 | 168 | 0.039 | 2990 | 1.298 | 2.33 | 2.760 |
| 5 | 9.794 | 77977 | 9998 | 1.003 | 39501 | 1.199 | 138.39 | 8.700 |
| 6 | 10.634 | 779 | 76 | 0.010 | 44238 | 2.772 | 1.06 | 4.219 |
| 7 | 11.827 | 1912 | 211 | 0.025 | 63717 | 1.703 | 2.92 | 6.142 |
| 8 | 12.607 | 7675268 | 1173759 | 98.682 | 93898 | 1.237 | 16247.16 | 4.440 |
| 9 | 14.458 | 1214 | 174 | 0.016 | 103722 | 1.201 | 2.41 | 10.790 |
| TOTAL | | 7777745 | 1186193 | 100.000 | | | | |

<UV-VIS CHROMATOGRAM>

<PEAK TABLE>

DETECTOR A 255NM

| PEAK # | RETENTION TIME | AREA | HEIGHT | AREA % | NUMBER OF THEORETICAL PLATES (JP) | SYMMETRY FACTOR | S/N | RESOLUTION (JP) |
|---|---|---|---|---|---|---|---|---|
| 1 | 3.521 | 1696 | 266 | 0.022 | 7920 | 1.307 | 3.69 | -- |
| 2 | 5.350 | 4895 | 160 | 0.064 | -- | -- | 2.21 | -- |
| 3 | 5.835 | 10954 | 1380 | 0.142 | 14432 | -- | 19.10 | -- |
| 4 | 6.785 | 3050 | 168 | 0.040 | 2990 | 1.298 | 2.33 | 2.760 |
| 5 | 10.634 | 779 | 76 | 0.010 | 44238 | 2.772 | 1.06 | 11.048 |
| 6 | 11.827 | 1912 | 211 | 0.025 | 63717 | 1.703 | 2.92 | 6.142 |
| 7 | 12.607 | 7675268 | 1173759 | 99.682 | 93898 | 1.237 | 16247.16 | 4.440 |
| 8 | 14.458 | 1214 | 174 | 0.016 | 103722 | 1.201 | 2.41 | 10.790 |
| TOTAL | | 7699768 | 1176195 | 100.000 | | | | |

| Peak # | Retention time | Area | Height | Area % | Number of theoretical plates (JP) | Symmetry factor | Resolution (JP) | S/N |
|---|---|---|---|---|---|---|---|---|
| 1 | 7.157 | 195 | 30 | 0.003 | 34160 | 1.2 | -- | 0.01 |
| 2 | 9.805 | 638 | 65 | 0.010 | 24919 | 1.1 | 13.166 | 0.01 |
| 3 | 12.216 | 6139185 | 400510 | 99.807 | 16125 | 1.3 | 7.635 | 80.61 |
| 4 | 13.724 | 1891 | 66 | 0.031 | -- | -- | -- | 0.01 |
| 5 | 24.173 | 335 | 55 | 0.005 | 401284 | 1.1 | -- | 0.01 |
| 6 | 24.683 | 1323 | 230 | 0.022 | 435199 | 1.4 | 3.385 | 0.05 |
| 7 | 25.087 | 149 | 66 | 0.002 | 3109805 | 1.0 | 3.916 | 0.01 |
| 8 | 25.288 | 1628 | 214 | 0.026 | 299648 | -- | 1.671 | 0.04 |
| 9 | 25.507 | 448 | 49 | 0.007 | -- | -- | -- | 0.01 |
| 10 | 26.411 | 669 | 157 | 0.011 | 837783 | -- | -- | 0.03 |
| 11 | 26.727 | 556 | 71 | 0.009 | 226144 | 1.1 | 1.859 | 0.01 |
| 12 | 26.965 | 3320 | 422 | 0.054 | 416591 | 2.4 | 1.220 | 0.08 |
| 13 | 27.321 | 356 | 49 | 0.006 | 357397 | 1.8 | 2.041 | 0.01 |
| 14 | 27.842 | 393 | 28 | 0.006 | 104400 | 0.7 | 1.980 | 0.01 |
| Total | | 6151085 | 402011 | 100.000 | | | | |

FORMULATION FOR ORAL ADMINISTRATION, COMPRISING TRIAZINE DERIVATIVE

REFERENCE TO AN ELECTRONIC SEQUENCE LISTING

The contents of the electronic sequence listing (AttachA4_20230822_P2021-00038US01_INFO_Sequence Listing_FS (1).xml; Size: 3,351 bytes; and Date of Creation: Aug. 29, 2023) is herein incorporated by reference in its entirety.

TECHNICAL FIELD

The present invention relates to a formulation for oral administration, comprising a triazine derivative. Specifically, the present invention relates to a formulation for oral administration, comprising a triazine derivative exhibiting coronavirus 3CL protease inhibitory activity, its pharmaceutically acceptable salt, or a complex thereof, as an active ingredient.

BACKGROUND ART

Coronaviruses belonging to the order Nidovirales, family Coronaviridae, and the subfamily Coronavirinae have a genome size of approximately 30 kilobases and are the largest single-stranded plus-stranded RNA viruses in the known RNA viruses. Coronaviruses are classified into four genera of Alphacoronavirus, Betacoronavirus, Gammacoronavirus, and Deltacoronavirus, and seven kinds in total of two kinds of the genus Alphacoronavirus (HCoV-229E and HCoV-NL63) and five kinds of the genus Betacoronavirus (HCoV-HKU1, HCoV-OC43, SARS-CoV, MERS-CoV, and SARS-CoV-2) are known as coronaviruses that infect humans. Among them, four kinds (HCoV-229E, HCoV-NL63, HCoV-HKU1, and HCoV-OC43) are pathogens of cold, and the remaining three kinds are severe acute respiratory syndrome (SARS) coronavirus (SARS-CoV), Middle East respiratory syndrome (MERS) coronavirus (MERS-CoV), and novel coronavirus (SARS-CoV-2) that cause severe pneumonia.

Novel coronavirus infections (COVID-19) outbreak in Wuhan, China in December 2019 has internationally widespread rapidly, and WHO announced pandemic on Mar. 11, 2020. The number of infected persons confirmed on Sep. 21, 2022 reaches 610 million or more, and the number of deaths reaches 6.5 million or more (Non-patent Document 1). Contact infection and aerosol infection have been reported as the main infection route of SARS-CoV-2, and it has been confirmed that SARS-CoV-2 keeps drifting in air with aerosols for about 3 hours and maintains infectivity (Non-patent Document 2). The incubation period is about 2 to 14 days, and cold-like symptoms such as fever (87.9%), dry coughing (67.7%), malaise (38.1%), and phlegm (33.4%) are typical (Non-patent Document 3). In severe cases, respiratory failures caused by acute respiratory distress syndrome, acute pulmonary disorder, interstitial pneumonia, etc. occur. Furthermore, multiple organ failures such as renal failure and hepatic failure have also been reported.

In Japan, as a result of drug repositioning of existing drugs, remdesivir, which is an antiviral drug, dexamethasone, which is an anti-inflammatory drug, and baricitinib, which is an antirheumatic drug, have been approved as therapeutic agents against COVID-19, and in January 2022, tocilizumab, which is an anti-IL-6 receptor antibody, have been received additional approval. Furthermore, in July 2021, Ronapreve (casirivimab/imdevimab), which is an antibody cocktail therapy, was specially approved, in September 2021, sotrovimab was specially approved, and in December 2021, molnupiravir was specially approved. Sufficient evidences are not obtained for efficacy and safety of these medicaments. Therefore, creating a therapeutic agent for COVID-19 is urgent.

Upon infection of cells, coronaviruses synthesize two polyproteins. In these two polyproteins, replication complexes producing viral genomes, and two proteases are included. Proteases cleave polyproteins synthesized from viruses and act indispensably to cause each protein to function. Of two proteases, a protease mostly taking charge of cleaving polyproteins is a 3CL protease (main protease) (Non-patent Document 4).

Regarding COVID-19 therapeutic agents targeting 3CL proteases, it was published in ClinicalTrials.gov in June 2021 that Phase 1b trials for Lufotrelvir (PF-07304814), which is a prodrug of PF-00835231, have completed by Pfizer Inc (NCT04535167). Furthermore, Pfizer Inc. announced in March 2021 to start Phase 1 test of the therapeutic agent PF-07321332 for Novel coronavirus infections. The structural formulae of PF-00835231, Lufotrelvir, and PF-07321332 are as shown below, and these agents are different from the compound of the present invention in chemical structure (Non-patent Documents 5, 12, and 13 and Patent Documents 6 and 7).

PF-00835231:

[Chemical Formula 1]

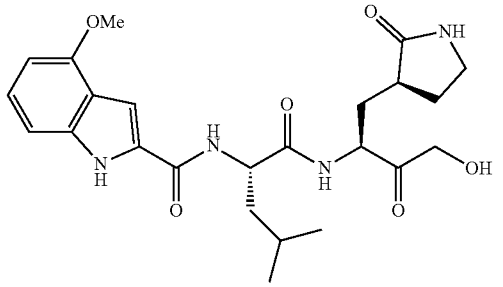

Lufotrelvir(PF-07304814):

[Chemical Formula 2]

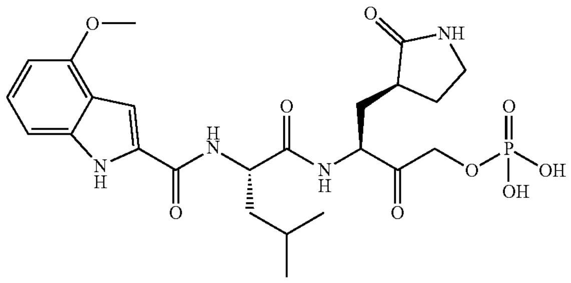

PF-07321332:

-continued

[Chemical Formula 3]

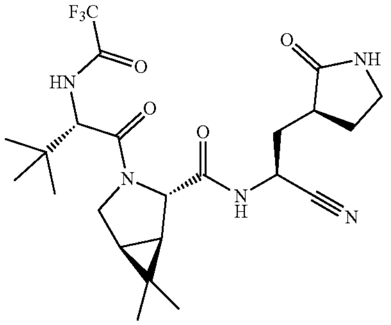

Further, it has been posted on ClinicalTrials.gov in July 2021 that Phase 2/3 test of combination use of PF-07321332 and Ritonavir for COVID-19 patients having high risk factors was started (NCT04960202). Moreover, in November 2021, it was reported on the Pfizer website, PAXLOVID™ (PF-07321332; ritonavir) reduced the risk of hospitalization or death by 89% in high-risk adult patients compared to placebo (Non-Patent Document 14). Furthermore, in December 2021, PAXLOVID™ was approved under Emergency Use Authorization in the United States, and on Feb. 10, 2022, the Paxlovid (registered trademark) PACK was approved as special case approval in Japan.

Although compounds having 3CL protease inhibitory activity are disclosed in Non-patent Documents 5 to 8, the composition, the production method, and the synthetic intermediate related to the present invention have neither been described nor suggested in any literatures.

Although triazine derivatives and uracil derivatives having $P2X_3$ and/or $P2X_{2/3}$ receptor antagonistic activity are disclosed in Patent Documents 1 to 4 and 8 to 12, 3CL protease inhibitory activity and antiviral effect have neither been described nor suggested in any literatures. Furthermore, the production method and the synthetic intermediate according to the present invention have neither been described nor suggested.

Although triazine derivatives having antitumor effects are disclosed in Non-patent Documents 9 to 11, coronavirus 3CL protease inhibitory activity and antiviral effect have not been described in any literatures, and the compound, the production method, and the synthetic intermediate related to the present invention have neither been described nor suggested.

Although triazine derivatives having galanin receptor-regulating action are disclosed in Patent Document 5, 3CL protease inhibitory activity and antiviral effect have neither been described nor suggested in any literatures. Furthermore, the production method and the synthetic intermediate according to the present invention have neither been described nor suggested.

PRIOR ART REFERENCES

Patent Document

[Patent Document 1] International Publication WO 2012/020749 A
[Patent Document 2] International Publication WO 2013/089212 A
[Patent Document 3] International Publication WO 2010/092966 A
[Patent Document 4] International Publication WO 2014/200078 A
[Patent Document 5] International Publication WO 2012/009258 A
[Patent Document 6] International Publication WO 2021/205298 A
[Patent Document 7] International Publication WO 2021/250648 A
[Patent Document 8] Chinese Patent Application Publication CN 113620888 A
[Patent Document 9] Chinese Patent Application Publication CN 113666914 A
[Patent Document 10] Chinese Patent Application Publication CN 113735838 A
[Patent Document 11] Chinese Patent Application Publication CN 113773300 A
[Patent Document 12] Chinese Patent Application Publication CN 113801097 A

Non-Patent Document

[Non-patent Document 1] "COVID-19 Dashboard by the Center for Systems Science and Engineering at Johns Hopkins University", [online], Johns Hopkins University, [searched on Sep. 21, 2022], Internet <URL: https://coronavirus.jhu.edu/map.html>
[Non-patent Document 2] The NEW ENGLAND JOURNAL of MEDICINE (2020), Vol. 382, pp. 1564 to 1567
[Non-patent Document 3] "Report of the WHO-China Joint Mission on Coronavirus disease 2019 (COVID-19)", [online], Feb. 28, 2020, WHO, [searched on Feb. 8, 2021], Internet <URL: https://www.who.int/docs/default-source/coronaviruse/who-china-joint-mission-on-covid-19-final-report.pdf>
[Non-patent Document 4] Science (2003), Vol. 300, pp. 1763 to 1767
[Non-patent Document 5] "A comparative analysis of SARS-CoV-2 antivirals characterizes 3CLpro inhibitor PF-00835231 as a potential new treatment for COVID-19", Journal of Virology, Apr. 26, 2021, [searched on Feb. 15, 2022], Internet <URL: https://journals.asm.org/doi/10.1128/JVI.01819-20><doi: 10.1128/JVI.01819-20>
[Non-patent Document 6] Cell Research (2020), Vol. 30, pp. 678 to 692
[Non-patent Document 7] Science (2020), Vol. 368, pp. 409 to 412
[Non-patent Document 8] ACS Central Science (2021), Vol. 7, No. 3, pp. 467 to 475
[Non-patent Document 9] Cancer Treatment Reviews (1984), Vol. 11, Supplement 1, pp. 99 to 110
[Non-patent Document 10] Contributions to Oncology (1984), Vol. 18, pp. 221 to 234
[Non-patent Document 11] Arzneimittel-Forschung (1984), Issue 11, Vol. 6, pp. 663 to 668
[Non-patent Document 12] 261st Am Chem Soc (ACS) Natl Meet 2021 Apr. 5/2021 Apr. 16 Virtual, N/A Abst 243
[Non-patent Document 13] Science (2021), Vol. 374, pp. 1586 to 1593
[Non-patent Document 14] "Pfizer's Novel COVID-19 Oral Antiviral Treatment Candidate Reduced Risk Of Hospitalization Or Death By 89% In Interim Analysis Of Phase 2/3 EPIC-HR Study", [online], Nov. 5, 2021, Pfizer Press Release, [searched on Feb. 15, 2022], Internet <URL: https://www.pfizer.com/news/press-release/press-release-detail/pfizers-novel-covid-19-oral-antiviral-treatment-candidate>

[Non-patent Document 15] AIMECS 2021 (AFMC International Medicinal Chemistry Symposium 2021), Online Symposium, Nov. 29 to Dec. 2, 2021

[Non-patent Document 16] bioRxiv preprint doi: https://doi.org/10.1101/2022.01.26.477782, "Discovery of S-217622, a Non-Covalent Oral SARS-CoV-2 3CL Protease Inhibitor Clinical Candidate for Treating COVID-19"

[Non-patent Document 17] J. Med. Chem. (2022), Vol. 65, pp. 6499 to 6512, "Discovery of S-217622, a Noncovalent Oral SARS-CoV-2 3CL Protease Inhibitor Clinical Candidate for Treating COVID-19"

SUMMARY OF THE INVENTION

Problems to Be Solved by the Invention

An object of the present invention is to provide a method for producing a triazine derivative exhibiting coronavirus 3CL protease inhibitory activity, its pharmaceutically acceptable salt, or a complex thereof.

Another object of the present invention is to provide a formulation to be orally administered, comprising a triazine derivative exhibiting coronavirus 3CL protease inhibitory activity, its pharmaceutically acceptable salt, or a complex thereof, as an active ingredient.

Means for Solving the Problem

The present invention relates to the following.

(1) A method for preparing a compound represented by Formula (III):

[Chemical Formula 6]

(III)

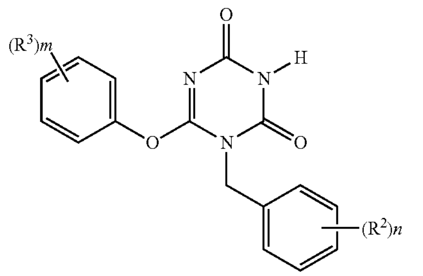

or its salt, the method comprising reacting a compound represented by Formula (I):

[Chemical Formula 4]

(I)

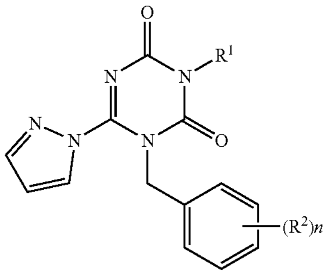

wherein $R^1$ is substituted or unsubstituted C1-C4 alkyl, $R^2$'s are each independently halogen, cyano, or methyl, and n is an integer of 1 to 5, or its salt, and a compound represented by Formula (II):

[Chemical Formula 5]

(II)

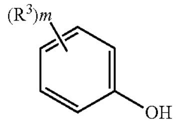

wherein $R^3$'s are each independently substituted or unsubstituted C1-C4 alkyl, and m is an integer of 0 to 5, or its salt, in the presence of an acid.

(2) The method according to the above-described item (1), in which the acid is trifluoroacetic acid.

(3) The method according to the above-described item (1) or (2), in which the compound represented by Formula (III) is a compound represented by Formula (III-1):

[Chemical Formula 7]

(III-1)

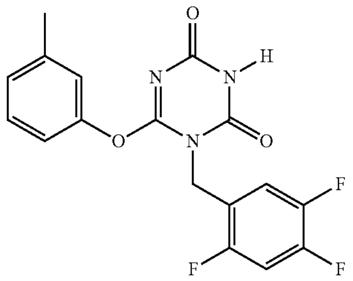

(4) A method for preparing a compound represented by Formula (VI):

[Chemical Formula 10]

(VI)

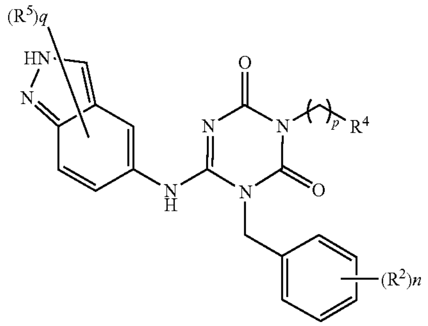

wherein symbols are as defined below, its salt, or a solvate thereof, the method comprising reacting a compound represented by Formula (IV):

[Chemical Formula 8]

(IV)

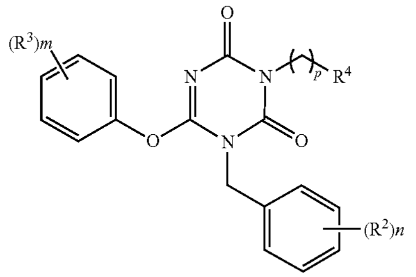

wherein $R^4$ is a substituted or unsubstituted aromatic heterocyclic group or a substituted or unsubstituted aromatic carbocyclic group, p is 0 or 1, and other symbols are as defined in the above-described item (1), or its salt, and a compound represented by Formula (V):

[Chemical Formula 9]

(V)

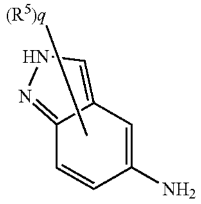

wherein $R^5$'s are each independently halogen or substituted or unsubstituted alkyl, and q is an integer of 0 to 5, or its salt, in the presence of an acid.

(5) The method according to the above-described item (4), in which the acid is acetic acid.

(6) The method according to the above-described item (4) or (5), in which the compound represented by Formula (VI) is a compound represented by Formula (VII):

[Chemical Formula 11]

(VII)

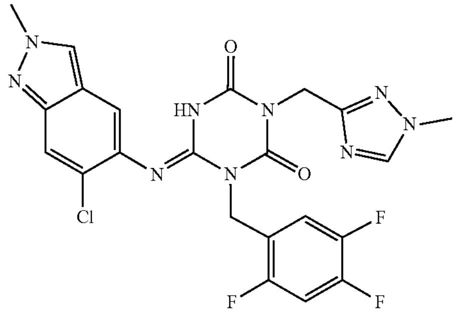

(7) A method for preparing a compound represented by Formula (VII):

[Chemical Formula 13]

(VII)

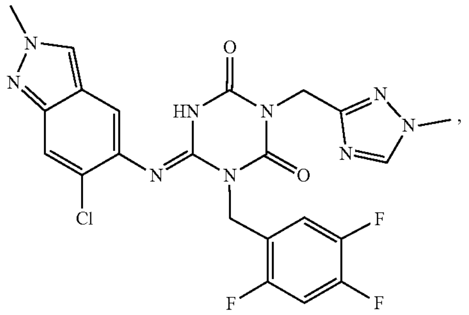

its salt, or a solvate thereof, the method comprising a step of obtaining a compound represented by Formula (III):

[Chemical Formula 12]

(III)

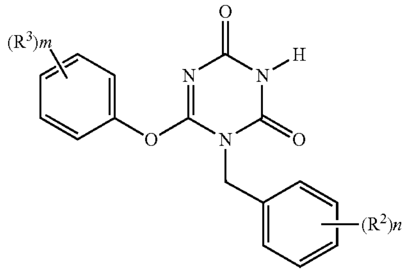

or its salt by the method according to any one of the above-described items (1) to (3).

(8) A method for producing fumaric acid cocrystal Form I of a compound represented by Formula (VII):

[Chemical Formula 14]

(VII)

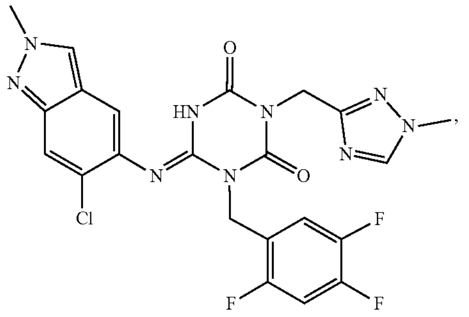

the method comprising crystallizing the compound represented by Formula (VII) or its salt in the presence of fumaric acid, acetone, and water.

(9) The method described in the above-described item (8), in which the method comprises crystallizing the compound represented by Formula (VII):

[Chemical Formula 15]

(VII)

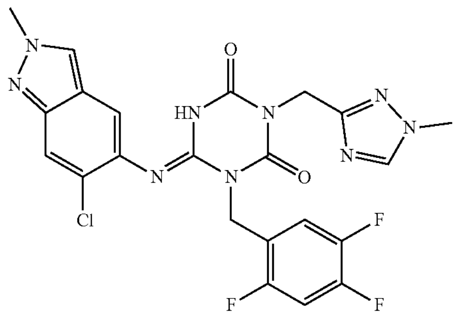

or its salt, which is obtained by using the production method described in any one of the above-described items (1) to (7).

(10) The method described in the above-described item (8) or (9), in which a crystallization temperature is 40 to 60° C., and a crystallization time is 120 minutes or longer.

(11) A compound represented by Formula (VIII):

[Chemical Formula 16]

(VIII)

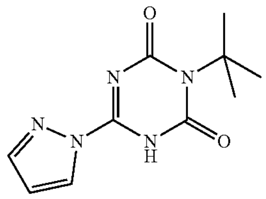

or its salt.

(12) A compound represented by Formula (IX):

[Chemical Formula 17]

(IX)

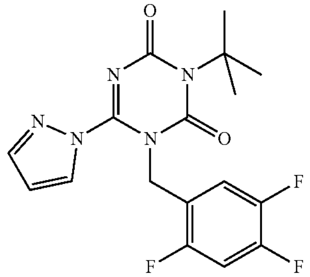

or its salt.

(13) A compound represented by Formula (X):

[Chemical Formula 18]

(X)

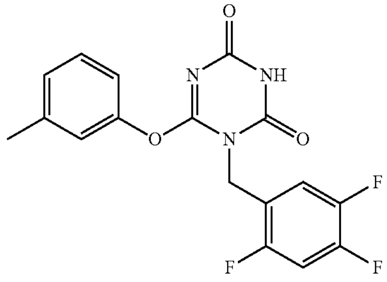

or its salt.

(14) A compound represented by Formula (XI):

[Chemical Formula 19]

(XI)

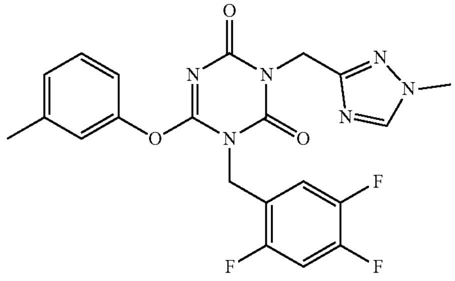

or its salt.

(15) A toluene solvate of a compound represented by Formula (VII):

[Chemical Formula 20]

(VII)

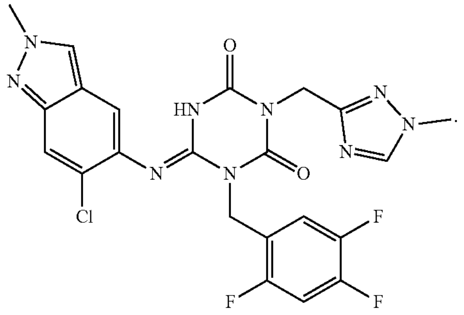

(16) Fumaric acid cocrystal Form I of a compound represented by Formula (VII):

[Chemical Formula 21]

(VII)

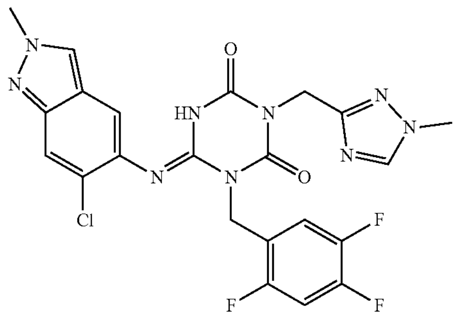

which does not substantially contain a free form of the compound represented by Formula (VII).

(17) A mesylate of a compound represented by the following formula:

[Chemical Formula 22]

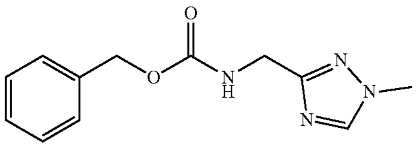

(18) A mesylate of a compound represented by the following formula:

[Chemical Formula 23]

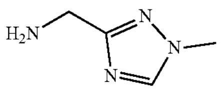

(19) A compound represented by the following formula:

[Chemical Formula 24]

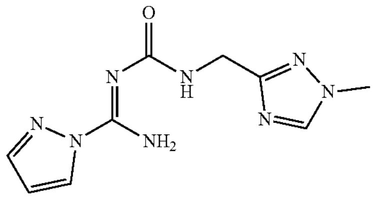

or its salt.

(20) A compound represented by the following formula:

[Chemical Formula 25]

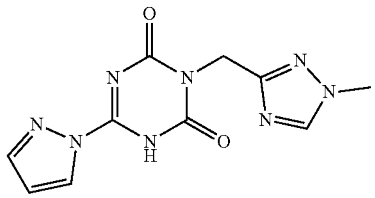

or its salt.

(21) The salt described in the above-described item (20), which is a 1,8-diazabicyclo[5.4.0]-7-undecene salt of a compound represented by the following formula:

[Chemical Formula 26]

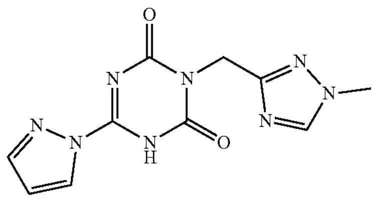

(22) A formulation (pharmaceutical composition) for oral administration, comprising a compound represented by Formula (VII):

[Chemical Formula 27]

(VII)

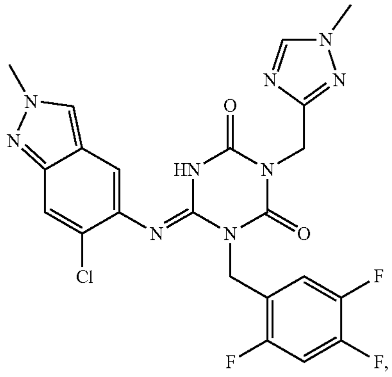

its pharmaceutically acceptable salt, or a complex thereof, as an active ingredient.

(23) The formulation (pharmaceutical composition) according to the above-described item (22), in which the active ingredient is a complex of the compound represented by Formula (VII), and the complex is containing fumaric acid.

(24) The formulation (pharmaceutical composition) according to the above-described item (23), in which the complex is a cocrystal composed of the compound represented by Formula (VII) and fumaric acid in a molar ratio of 1:1.

(25) The formulation (pharmaceutical composition) according to any one of the above-described items (22) to (24), comprising a polymer in the formulation.

(26) The formulation (pharmaceutical composition) according to the above-described item (25), wherein the polymer is one or more selected from a cellulose-based polymer, an acrylic polymer, and a vinyl-based polymer.

(27) The formulation (pharmaceutical composition) according to any one of the above-described items (22) to (26), wherein the active ingredient is a compound obtained by the method according to any one of the above-described items (4) to (10), its pharmaceutically acceptable salt, or a complex thereof.

(28) The formulation (pharmaceutical composition) according to any one of the above-described items (22) to (27), for treating and/or preventing coronavirus disease.

(29) The formulation (pharmaceutical composition) according to any one of the above-described item (28), in which the coronavirus disease is Novel coronavirus infections (COVID-19).

(30) The formulation according to the above-described item (22), comprising 125.0 mg of the compound represented by Formula (VII) as an active ingredient.

(31) The formulation according to the above-described item (23), comprising 152.3 mg of a complex composed of the compound represented by Formula (VII) and fumaric acid in a molar ratio of 1:1.

(32) The formulation according to the above-described item (22), comprising 250.0 mg of the compound represented by Formula (VII) as an active ingredient.

(33) The formulation according to the above-described item (23), comprising 304.6 mg of a complex composed of the compound represented by Formula (VII) and fumaric acid in a molar ratio of 1:1.

(34) The formulation according to the above-described item (22), comprising 25.0 mg of the compound represented by Formula (VII) as an active ingredient.

(35) The formulation according to the above-described item (23), comprising 30.46 mg of a complex composed of the compound represented by Formula (VII) and fumaric acid at a molar ratio of 1:1.

(36) The formulation according to any one of the above-described items (22) to (35), for use in a child who is 12 years old or older and an adult.

(37) The formulation according to any one of the above-described items (22) to (35), for use in a child who is 6 years old or older and younger than 12 years old.

Effect of the Invention

The compound prepared by the manufacturing method according to present invention has inhibitory activity against the coronavirus 3CL protease and is useful as a therapeutic agent and/or prophylactic agent for coronavirus disease.

Furthermore, the compound prepared by the manufacturing method according to the present invention is useful as a pharmaceutical bulk material.

Further, a pharmaceutical composition comprising fumaric acid cocrystal of Compound (I-0005) prepared by the manufacturing method according to the present invention is extremely useful as a therapeutic agent for Novel coronavirus infections (COVID-19). The preparing method according to the present invention is a method by which the compound according to the present invention can be manufactured in a good yield.

The formulation (pharmaceutical composition) for oral administration according to the present invention has inhibitory activity against the coronavirus 3CL protease and is useful as a therapeutic agent and/or prophylactic agent for coronavirus disease.

BRIEF DESCRIPTION OF DRAWINGS

FIG. 2 shows a peak list of the X-ray powder analysis patterns of FIG. 1.

FIG. 10 shows a peak table of the X-ray powder analysis patterns of FIG. 9.

MODE FOR CARRYING OUT THE INVENTION

Figure 1:
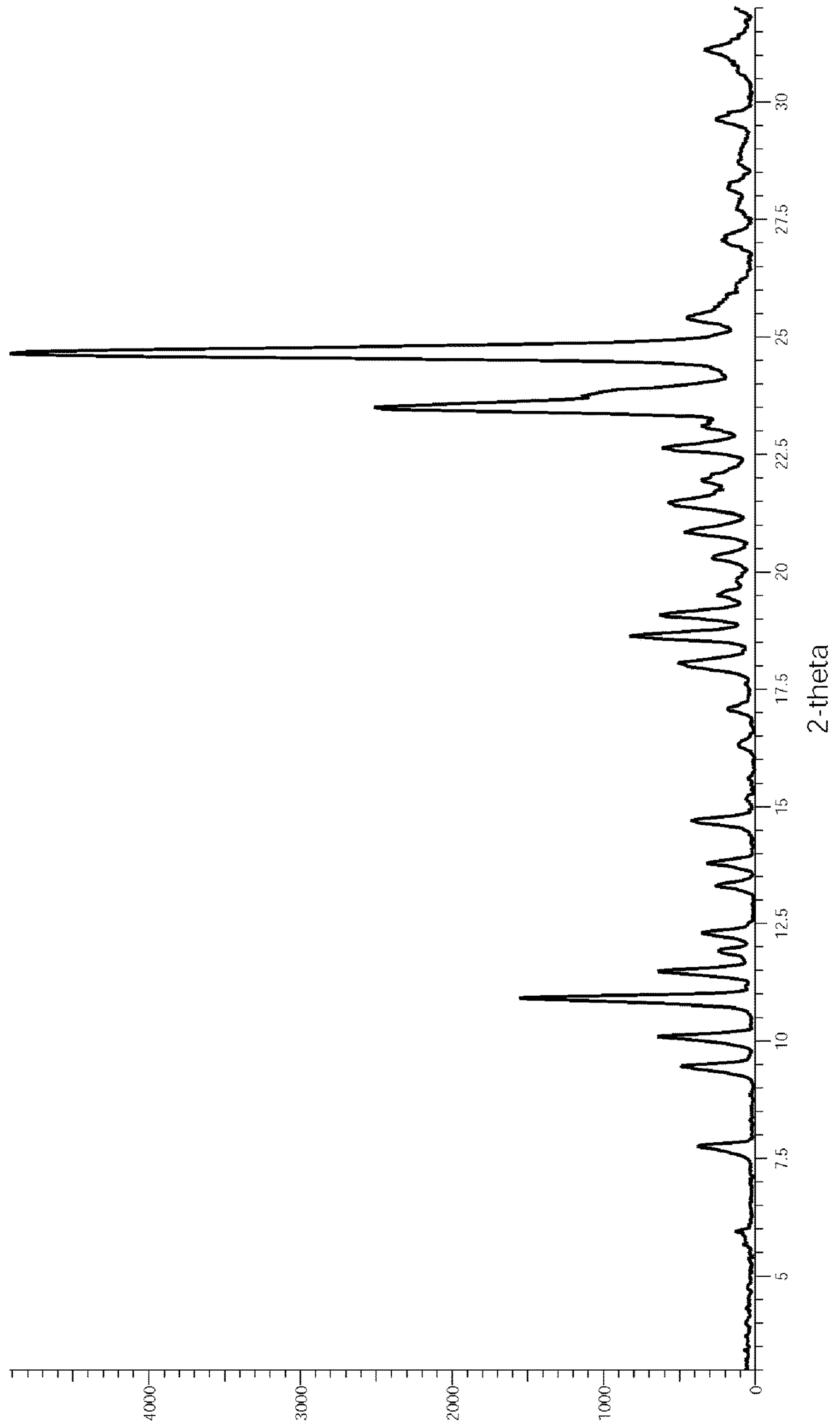
FIG. 1 shows X-ray powder diffraction patterns of fumaric acid cocrystal Form I (Form I) of a compound represented by Formula (VII) in Example a. The horizontal axis represents 2θ (°) and the vertical axis represents intensity (Count).

The meanings of the terms as used herein are described below. Unless otherwise specified, each term has the same meaning when used alone or in combination with other terms.

The term "consisting of" means to have only the described elements.

The term "comprising" or "containing" means not to limit to the described elements and not to exclude undescribed elements.

Furthermore, it should be understood that, throughout the present specification, the expression of a singular form includes the concept of its plural form unless specified otherwise. Therefore, it should be understood that the article of the singular form (for example, in English, "a", "an", "the", and the like) includes the concept of its plural form unless specified otherwise.

Furthermore, it should be understood that the terms used herein are used in a meaning normally used in the art unless specified otherwise. Thus, unless defined otherwise, all technical and scientific terms used herein have the same meaning as those generally understood by those skilled in the art in the field to which the present invention pertains. If there is a contradiction, the present specification (including definitions) precedes.

"Halogen" includes a fluorine atom, a chlorine atom, a bromine atom, and an iodine atom. In particular, halogen is preferably a fluorine atom and a chlorine atom.

"Alkyl" includes a linear or branched hydrocarbon group having 1 to 15 carbon atoms, preferably 1 to 10 carbon atoms, more preferably 1 to 6 carbon atoms, and further preferably 1 to 4 carbon atoms. Examples thereof include methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl, isooctyl, n-nonyl, and n-decyl.

Examples of a preferred embodiment of "alkyl" include methyl, ethyl, n-propyl, isopropyl, n-butyl, isobutyl, sec-butyl, tert-butyl, and n-pentyl. Examples of a further preferred embodiment thereof include methyl, ethyl, n-propyl, isopropyl, and tert-butyl.

"C1-C4 alkyl" includes a linear or branched hydrocarbon group having 1 to 4 carbon atoms. Examples thereof include methyl, ethyl, n-propyl, isopropyl, n-butyl, isobutyl, sec-butyl, and tert-butyl.

An "aromatic carbocyclic group" means a cyclic aromatic hydrocarbon group which is monocyclic or polycyclic having two or more rings. Examples thereof include phenyl, naphthyl, anthryl, and phenanthryl. Examples of a 6-membered aromatic carbocyclic group include phenyl. Examples of a 10-membered aromatic carbocyclic group include naphthyl. Examples of a 14-membered aromatic carbocyclic group include anthryl and phenanthryl.

Examples of a preferred embodiment of the "aromatic carbocyclic group" include phenyl.

An "aromatic carbocycle" means a ring derived from the above-described "aromatic carbocyclic group".

An "aromatic heterocyclic group" means an aromatic cyclic group, which is monocyclic or polycyclic having two or more rings, having one or more, same or different heteroatom(s) selected optionally from O, S, and N.

The aromatic heterocyclic group which is polycyclic having two or more rings include a fused ring group wherein an aromatic heterocyclic group, which is monocyclic or polycyclic having two or more rings, is fused with a ring of the above-described "aromatic carbocyclic group" and may have the binding group at any ring(s).

The aromatic heterocyclic group which is monocyclic is preferably a 5- to 8-membered ring and more preferably a 5- or 6-membered ring. Examples of the 5-membered aromatic heterocyclic group include pyrrolyl, imidazolyl, pyrazolyl, triazolyl, tetrazolyl, furyl, thienyl, isoxazolyl, oxazolyl, oxadiazolyl, isothiazolyl, thiazolyl, and thiadiazolyl. Examples of the 6-membered aromatic heterocyclic group include pyridyl, pyridazinyl, pyrimidinyl, pyrazinyl, and triazinyl.

The aromatic heterocyclic group which is bicyclic is preferably an 8- to 10-membered ring and more preferably a 9- or 10-membered ring. Examples thereof include indolyl, isoindolyl, indazolyl, indolizinyl, quinolinyl, isoquinolinyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, oxazolopyridyl, and thiazolopyridyl. Examples of the 9-membered aromatic heterocyclic group include indolyl, isoindolyl, indazolyl, indolizinyl, purinyl, benzimidazolyl, benzisoxazolyl, benzoxazolyl, benzoxadiazolyl, benzisothiazolyl, benzothiazolyl, benzothiadiazolyl, benzotriazolyl, benzofuranyl, imidazopyridyl, triazolopyridyl, oxazolopyridyl, and thiazolopyridyl. Examples of the 10-membered aromatic heterocyclic group include quinolinyl, isoquinolinyl, cinnolinyl, phthalazinyl, quinazolinyl, naphthyridinyl, quinoxalinyl, pteridinyl, and pyrazinopyridazinyl.

The aromatic heterocyclic group which is polycyclic having three or more rings is preferably a 13- to 15-membered ring. Examples thereof include carbazolyl, acridinyl, xanthenyl, phenothiazinyl, phenoxathiinyl, phenoxazinyl, and dibenzofuryl.

Examples of a preferred embodiment of the "aromatic heterocyclic group" include triazolyl.

An "aromatic heterocycle" means a ring derived from the above-described "aromatic heterocyclic group".

Examples of a substituent of the "substituted alkyl" include the following substituent group A. A carbon atom at any position(s) may be bonded to one or more group(s) selected from the following substituent group A.

Substituent group A: halogen, cyano, and nitro.

Examples of a substituent of the "substituted C1-C4 alkyl" include the following substituent group B. A carbon atom at any position(s) may be bonded to one or more group(s) selected from the following substituent group B.

Substituent group B: halogen, cyano, and nitro.

Examples of substituents on the ring of "aromatic carbocycle" and "aromatic heterocycle" of a "substituted aromatic carbocyclic group" and a "substituted aromatic heterocyclic group", etc. include the following substituent group C. An atom at any position(s) on the ring may be bonded to one or more group(s) selected from the following substituent group B.

Substituent group C: halogen, cyano, nitro, and alkyl.

The compounds represented by Formula (VI) and Formula (VII) are not limited to particular isomers, but include any possible isomers (for example, keto-enol isomer, imine-enamine isomer, diastereoisomer, optical isomer, rotamer, etc.), racemates, and a mixture thereof.

[Chemical Formula 28]

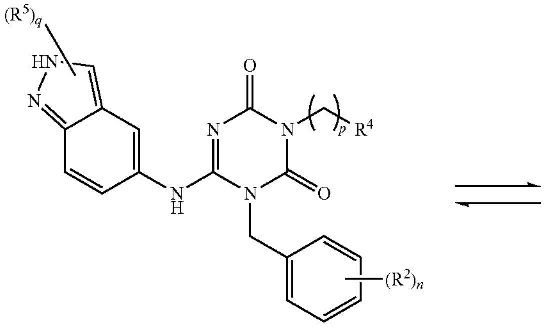

(VI)

-continued

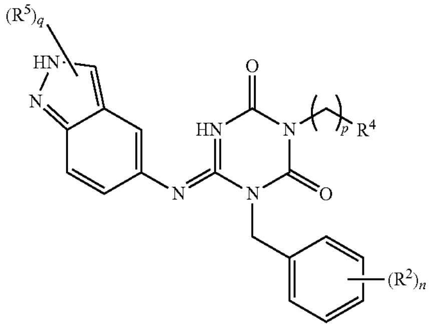

(VI)

For example, the compound represented by Formula (VII) and Compound I-005 include tautomers as shown below.

[Chemical Formula 29]

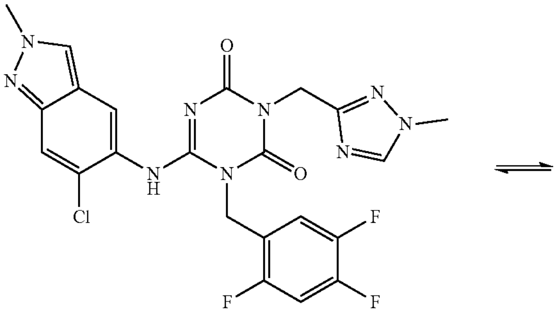

(VII)

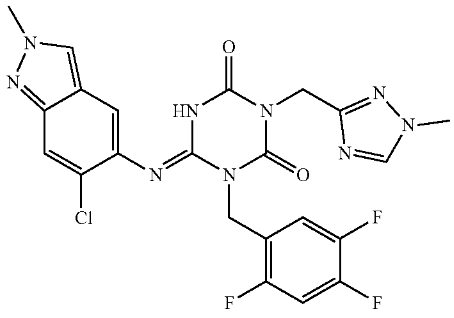

(VII)

The fumaric acid cocrystal Form I of the compound represented by Formula (VII):

[Chemical Formula 30]

(VII)

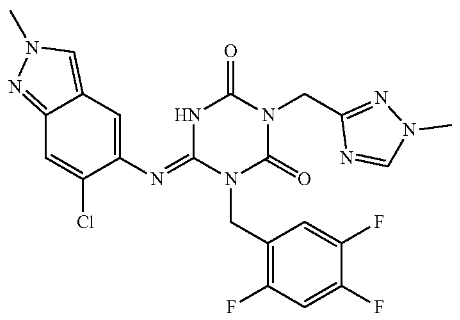

which does not substantially contain a free form of the compound represented by Formula (VII) means the fumaric acid cocrystal Form I of the compound represented by Formula (VII) in which a peak derived from the free form of the compound represented by Formula (VII) is not detected (is equal to or lower than the detection limit) by a measuring instrument such as X-ray powder diffraction measurement.

Furthermore, one or more hydrogen atom, carbon atom, and/or another atom of the compounds represented by Formula (I), Formula (II), Formula (III), Formula (IV), Formula (V), Formula (VI), Formula (VII), Formula (VIII), Formula (IX), Formula (X), and Formula (XI) (hereinafter, referred to as Formula (VII) or the like) may be replaced with an isotope of the hydrogen atom, carbon atom, and/or another atom. Examples of such an isotope include hydrogen, carbon, nitrogen, oxygen, phosphorus, sulfur, fluorine, iodine, and chlorine such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{123}I$, and $^{36}Cl$. The compound represented by Formula (VII) or the like also includes compounds replaced with such an isotope. The compounds replaced with an isotope are also useful as a pharmaceutical product and include all of radiolabeled forms of the compound represented by Formula (VII) or the like. Furthermore, a "method of radioactive labeling" for the production of the "radiolabeled form" is also included in the present invention, and this "radiolabeled form" is useful as a tool for research for metabolic pharmacokinetics, research and/or diagnosis in binding assay.

Furthermore, the crystal of the present invention may be a deuterated form. The crystalline form of the present invention may also be labeled with radioisotopes (for example, $^{3}H$, $^{14}C$, $^{35}S$, and $^{125}I$).

The radiolabeled form of the compound represented by Formula (VII) or the like can be prepared by the method well known in this technical field. For example, a tritium-labeled compound represented by Formula (VII) or the like can be prepared by introducing tritium into a specific compound represented by Formula (VII) or the like by catalytic dehalogenation reaction using tritium. This method includes reaction of a precursor which is a compound represented by Formula (VII) or the like appropriately halogenated with tritium gas in the presence of an appropriate catalyst, for example, Pd/C, and in the presence or absence of a base. For another appropriate method for preparing a tritium-labeled compound, "Isotopes in the Physical and Biomedical Sciences, Vol. 1, Labeled Compounds (Part A), Chapter 6 (1987)" can be referred to. $^{14}C$-labeled compound can be prepared using a raw material having $^{14}C$ carbon.

In the formulation of the present invention, a pharmaceutically acceptable salt of the compound represented by Formula (VII) or the like can be used. Examples of the pharmaceutically acceptable salt of the compound represented by Formula (VII) or the like include salts of the compound represented by Formula (VII) or the like with alkali metal (for example, lithium, sodium, potassium, etc.), alkaline earth metal (for example, calcium, barium, etc.), magnesium, transition metal (for example, zinc, iron, etc.), ammonia, organic base (for example, trimethylamine, triethylamine, dicyclohexylamine, ethanolamine, diethanolamine, triethanolamine, meglumine, ethylenediamine, pyridine, picoline, quinoline, etc.) and amino acid or salts of the compound represented by Formula (VII) or the like with inorganic acid (for example, hydrochloric acid, sulfuric acid, nitric acid, carbonic acid, hydrobromic acid, phosphoric acid, hydroiodic acid, etc.), and organic acid (for example, formic acid, acetic acid, propionic acid, trifluoroacetic acid, citric acid, lactic acid, tartaric acid, oxalic acid, maleic acid, fumaric acid, succinic acid, mandelic acid, glutaric acid, malic acid, benzoic acid, phthalic acid, ascorbic acid, benzenesulfonic acid, p-toluenesulfonic acid, methanesulfonic acid, ethanesulfonic acid, trifluoroacetic acid, etc.). These salts can be formed by the method which is usually performed.

The pharmaceutically acceptable salt of the compound represented by Formula (VII) may be composed of, for example, the compound represented by Formula (VII) and a counter molecule or a counter ion and may include any number of counter molecules or counter ions. The pharmaceutically acceptable salt of the compound represented by Formula (VII) indicates one which mediates ion bonding by proton movement between the compound and a counter molecule or a counter atom.

In the formulation of the present invention, a complex of the compound represented by Formula (VII) or its pharmaceutically acceptable salt can be used. The compound represented by Formula (VII) or its pharmaceutically acceptable salt may form a solvate (for example, hydrate, etc.), a cocrystal, and/or a clathrate, and these are described as "complex" herein.

In the "solvate" used herein, any number of solvent molecules (for example, water molecule, etc.) may be coordinated, for example, to the compound represented by Formula (VII) or the like. By leaving the compound represented by Formula (VII) or the like or its pharmaceutically acceptable salt in the atmosphere, it may absorb moisture to adhere with adsorbed water or form a hydrate thereof.

Examples of the solvent molecule include acetonitrile, chlorobenzene, chloroform, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethylene glycol, formamide, hexane, methanol, 2-methoxyethanol, methylbutyl ketone, methylcyclohexane, N-methylpyrrolidone, nitromethane, pyridine, sulfolane, tetralin, toluene, 1,1,2-trichloroethene, xylene, acetic acid, anisole, 1-butanol, 2-butanol, n-butyl acetate, t-butyl methyl ether, cumene, dimethylsulfoxide, ethyl acetate, diethyl ether, ethyl formate, formic acid, heptane, isobutyl acetate, isopropyl acetate, methyl acetate, 3-methyl-1-butanol, methyl ethyl ketone, methyl isobutyl ketone, 2-methyl-1-propanol, pentane, 1-pentanol, 1-propanol, 2-propanol, propyl acetate, tetrahydrofuran, water (that is, hydrate), ethanol, acetone, 1,1-diethoxypropane, 1,1-dimethoxymethane, 2,2-dimethoxypropane, iso-octane, isopropyl ether, methyl isopropyl ketone, methyltetrahydrofuran, petroleum ether, trichloroacetic acid, and trifluoroacetic acid, preferably, acetic acid, anisole, 1-butanol, 2-butanol, n-butyl acetate, t-butyl methyl ether, cumene, dimethylsulfoxide, ethyl acetate, diethyl ether, ethyl formate, formic acid, heptane, isobutyl acetate, isopropyl acetate, methyl acetate, 3-methyl-1-butanol, methyl ethyl ketone, methyl isobutyl ketone, 2-methyl-1-propanol, pentane, 1-pentanol, 1-propanol, 2-propanol, propyl acetate, tetrahydrofuran, water (that is, hydrate), ethanol, acetone, 1,1-diethoxypropane, 1,1-dimethoxymethane, 2,2-dimethoxypropane, iso-octane, isopropyl ether, methyl isopropyl ketone, methyltetrahydrofuran, petroleum ether, trichloroacetic acid, and trifluoroacetic acid, and more preferably, water (that is, hydrate), ethanol, acetone, 1,1-diethoxypropane, 1,1-dimethoxymethane, 2,2-dimethoxyprop ane, iso-octane, isopropyl ether, methyl isopropyl ketone, methyltetrahydrofuran, petroleum ether, trichloroacetic acid, and trifluoroacetic acid.

The "cocrystal" used herein means that counter molecules are regularly arranged in the same crystal lattice and may include any number of counter molecules. Further, the cocrystal indicates one in which the intermolecular interaction between the compound and the counter molecule is mediated with non-covalent and non-ionic chemical interaction such as hydrogen bonding or van der Waals' force.

For example, the cocrystal of the compound represented by Formula (VII) may be composed of the compound represented by Formula (VII) and a counter molecule and may include any number of counter molecules. Preferably, the cocrystal may be composed of the compound represented by Formula (VII) and fumaric acid and may include any number of fumaric acids. Further preferably, the cocrystal is a cocrystal composed of the compound represented by Formula (VII) and fumaric acid at a molar ratio of 1:1.

The cocrystal is distinguished from a salt in that the compound is essentially uncharged or neutral.

The cocrystal is distinguished from a hydrate or a solvate in that the counter molecule is not water or a solvent.

The compounds represented by Formula (I), Formula (II), Formula (III), Formula (IV), Formula (V), Formula (VI), Formula (VII), Formula (VIII), Formula (IX), Formula (X), and Formula (XI) or its salt of the present invention may form solvates (for example, hydrates, etc.), cocrystals and/or crystalline polymorphisms, and the present invention also includes such various solvates, cocrystals, and crystalline polymorphisms. In the "solvate", any number of solvent molecules (for example, water molecule, etc.) may be coordinated to the compounds represented by Formula (I), Formula (II), Formula (III), Formula (IV), Formula (V), Formula (VI), Formula (VII), Formula (VIII), Formula (IX), Formula (X), and Formula (XI). The crystalline polymorphisms may be formed by recrystallization of the compounds represented by Formula (I), Formula (II), Formula (III), Formula (IV), Formula (V), Formula (VI), Formula (VII), Formula (VIII), Formula (IX), Formula (X), and Formula (XI) or its salt.

The "crystal" used herein means a solid in which constituent atoms, ions, molecules, etc. are three-dimensionally arranged with regularity, and is distinguished from a non-crystalline solid not having such a regular inner structure. The crystal of the present invention may be a single crystal, a twin crystal, a polycrystal, and the like.

Further, in the "crystal", there may be a "crystalline polymorphism" which has the same composition but has different arrangement in the crystal, and crystals including these are referred to as the "crystalline form".

In addition, the compounds represented by Formula (I), Formula (II), Formula (III), Formula (IV), Formula (V), Formula (VI), Formula (VII), Formula (VIII), Formula (IX), Formula (X), and Formula (XI) may be converted into its salt or its pharmaceutically acceptable solvate. The crystals of the present invention may be any of salts, hydrates, solvates, and crystalline polymorphisms thereof, even the case of a mixture of two or more kinds thereof is intended to be encompassed in the scope of the invention.

The crystalline form and the degree of crystallinity can be measured by many techniques including, for example, X-ray powder diffraction measurement, Raman spectroscopy, an infrared absorption spectrum measurement method, moisture adsorption-desorption measurement, differential scanning calorimetry, and dissolution properties.

Furthermore, a "crystalline polymorphism" may be formed by recrystallization of the compound represented by Formula (VII) or the like, its pharmaceutically acceptable salt, or a complex thereof.

In the formulation of the present invention, such various salts, complexes (hydrate, solvate, cocrystal, and clathrate), and the crystalline polymorphism can be used, and a mixture of two or more kinds thereof can also be used.

(X-Ray Powder Diffraction (XRPD))

The X-ray powder diffraction (XRPD) is one of the most sensitive analytical methods for measuring the crystalline form and crystallinity of solid. When crystals are irradiated with X-rays, the X-rays are reflected by the crystal lattice planes and mutually interfere, and the ordered diffraction lines corresponding to the periodicity of the structure are observed. On the other hand, in the case of amorphous solids, usually, since they do not have the ordered iteration periodicity in the structure, diffraction phenomenon does not occur, and featureless broad XRPD patterns (also called halo patterns) are shown.

The crystalline form of the compound represented by Formula (VII) or the like can be identified by the X-ray powder diffraction pattern and characteristic diffraction peaks. The crystalline form of the compound represented by Formula (VII) or the like can be distinguished from the other crystalline form by the presence of characteristic diffraction peaks.

The characteristic diffraction peaks used herein are peaks selected from the observed diffraction pattern. The characteristic diffraction peaks are selected from preferably about ten, more preferably about five, and further preferably about three in the diffraction pattern.

In order to distinguish between multiple crystals, a peak which is shown for the crystal and not shown for the other crystal becomes a more preferable characteristic peak than the intensity of a peak when the crystal is specified. The crystal can be characterized by one or two peak(s) if it is such characteristic peak(s). By comparing the chart obtained by measuring, if these characteristic peaks coincide, the X-ray powder diffraction pattern can be said to substantially match up.

Since an error in the range of ±0.2° may occur in diffraction angles (2θ) in X-ray powder diffraction, in general, the value of the diffraction angle of X-ray powder diffraction should be understood as the one including values in a range of around ±0.2°. Therefore, the present invention includes not only crystalline forms whose diffraction angles of the peaks in X ray powder diffraction perfectly match, but also crystalline forms whose diffraction angles of the peaks match within an error of around ±0.2°.

In general, it is known that the intensities of the peaks shown in the following tables and drawings may vary depending on a number of factors, for example, selected orientation effects of crystals in the X-ray beam, effect of coarse particle, purity of the material to be analyzed, or degree of crystallinity of the sample. Furthermore, the peak positions may also shift for variations in sample height. Further, measurements using a different wavelength will result in different shifts according to the Bragg equation ($n\lambda=2d \sin \theta$). Such another XRPD patterns obtained by using a different wavelength are also within the scope of the present invention.

(Single Crystal Structural Analysis)

By one of methods of identifying a crystal, crystallographic parameters in the crystal, atomic coordinates (values indicating spatial positional relationship of individual atoms), and the three-dimensional structural model can be obtained. Refer to "Manual of X-ray structural analysis" written by Sakurai Toshio, published by Shokabo Co., Ltd. (1983), X-Ray Structure Determination: A Practical Guide, written by Stout & Jensen, Macmillan Co., New York (1968), and the like. The single crystal structural analysis is useful to identify the crystalline structures of the complex, salt, optical isomer, tautomer, and geometric isomer as described in the present invention.

The compound represented by Formula (VII) or the like has coronavirus 3CL protease inhibitory activity, and thus is useful as a therapeutic and/or prophylactic agent for diseases that involve the coronavirus 3CL protease. A "therapeutic agent and/or prophylactic agent" in the present invention also includes a symptom-improving agent. As the diseases that involve the coronavirus 3CL protease, virus diseases are exemplified, and preferably, coronavirus diseases are exemplified.

As an embodiment, examples of the coronavirus include coronaviruses that infect humans. Examples of the coronaviruses that infect humans include HCoV-229E, HCoV-NL63, HCoV-HKU1, HCoV-OC43, SARS-CoV, MERS-CoV, and/or SARS-CoV-2.

As an embodiment, as the coronavirus, Alphacoronavirus and/or Betacoronavirus, more preferably Betacoronavirus, and further preferably Sarbecovirus are exemplified.

As an embodiment, examples of the Alphacoronavirus include HCoV-229E and HCoV-NL63. Particularly preferably, HCoV-229E is exemplified.

As an embodiment, examples of the Betacoronavirus include HCoV-HKU1, HCoV-OC43, SARS-CoV, MERS-CoV, and/or SARS-CoV-2. Preferably, HCoV-OC43 or SARS-CoV-2 is exemplified, and particularly preferably, SARS-CoV-2 is exemplified.

As an embodiment, examples of the Betacoronavirus include β-coronavirus lineage A, β-coronavirus lineage B, and β-coronavirus lineage C. More preferably, β-coronavirus lineage A and β-coronavirus lineage B are exemplified, and particularly preferably, β-coronavirus lineage B is exemplified.

As the β-coronavirus lineage A, for example, HCoV-HKU1 and HCoV-OC43 are exemplified, and preferably, HCoV-OC43 is exemplified. As the β-coronavirus lineage B, for example, SARS-CoV and SARS-CoV-2 are exemplified, and preferably, SARS-CoV-2 is exemplified. As the β-coronavirus lineage B, preferably MERS-CoV is exemplified.

As an embodiment, as the coronavirus, HCoV-229E, HCoV-OC43, and/or SARS-CoV-2 are exemplified, and particularly preferably, SARS-CoV-2 is exemplified.

Examples of the coronavirus disease include infective diseases due to HCoV-229E, HCoV-NL63, HCoV-OC43, HCoV-HKU1, SARS-CoV, MERS-CoV, and/or SARS-CoV-2. Preferably, infective diseases due to HCoV-229E, HCoV-OC43, and/or SARS-CoV-2 are exemplified, and particularly preferably, infective diseases due to SARS-CoV-2 are exemplified.

As the coronavirus disease, particularly preferably, Novel coronavirus infections (COVID-19) is exemplified.

Hereinafter, the preparing method according to the present invention will be described.

Step 1 Method for Preparing Compound Represented by Formula (III)

[Chemical Formula 31]

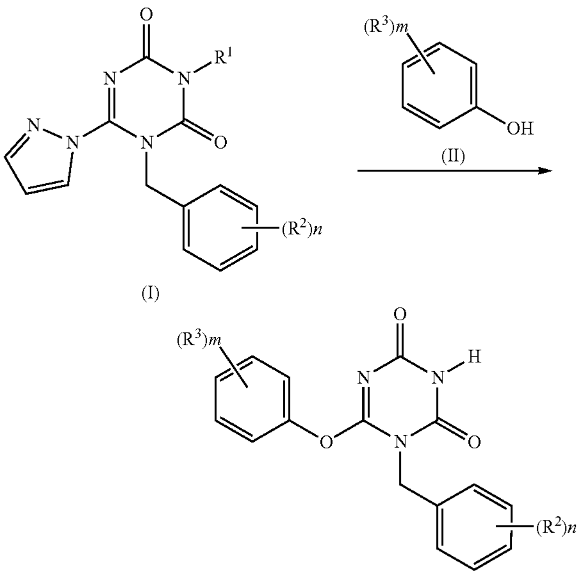

(I)

(III)

Symbols in the formula are the same as defined above.

This step is a method for preparing a compound represented by Formula (III), characterized in that a compound represented by Formula (I) and a compound represented by Formula (II) are reacted in the presence of an acid.

The compound represented by Formula (II) can be used usually in an amount of 1.0 to 5.0 equivalents, for example, 1.0 to 3.0 equivalents with respect to the compound represented by Formula (I).

The solvent is not particularly limited as long as it allows the aforementioned step to proceed efficiently, and an acid may be used as the solvent. Examples thereof include acids, toluene, methylene chloride, and dichloroethane, and these can be used alone or as a mixture. Preferably, acids are exemplified.

Examples of the acids include protonic acid and Lewis acid, and preferably include trifluoroacetic acid.

Regarding the amount of acid used, usually, 1.0 equivalent to a large excess of acid, for example, 5.0 equivalents to a large excess thereof with respect to the compound represented by Formula (I) can be used.

The reaction temperature is not particularly limited, and the reaction can be usually performed at about 0° C. to about 50° C., preferably at room temperature to 40° C.

The reaction time is not particularly limited and is usually 0.1 to 12 hours, and preferably 0.1 to 5 hours.

Step 2 Method for Preparing Compound Represented by Formula (VI)

[Chemical Formula 32]

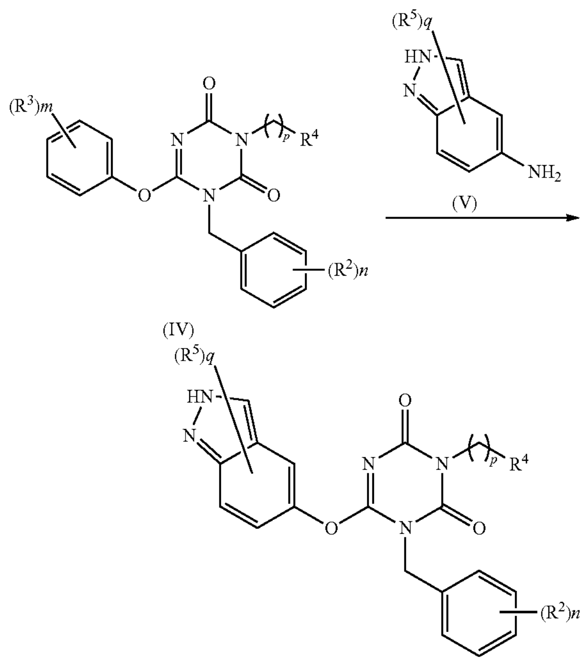

(IV)

(V)

(VI)

Symbols in the formula are the same as defined above.

This step is a method for preparing a compound represented by Formula (VI), characterized in that a compound represented by Formula (IV) and a compound represented by Formula (V) are reacted in the presence of an acid.

The compound represented by Formula (V) can be used usually in an amount of 1.0 to 5.0 equivalents, for example, 1.0 to 1.5 equivalents with respect to the compound represented by Formula (IV).

The solvent is not particularly limited as long as it allows the aforementioned step to proceed efficiently, and an acid may be used as the solvent. Examples thereof include toluene, t-butanol, and t-amyl alcohol, and these can be used alone or as a mixture. Preferably, toluene is exemplified.

Examples of acids include acetic acid and 2,2-dimethylbutanoic acid. Preferably, acetic acid is exemplified.

Regarding the amount of acid used, usually, 1.0 equivalent to 10 equivalents of acid, for example, 3.0 equivalents to 10 equivalents thereof with respect to the compound represented by Formula (IV) can be used.

The reaction temperature is not particularly limited and the reaction can be usually performed at room temperature to about 150° C. or under microwave irradiation, preferably at 50 to 150° C. or under microwave irradiation.

The reaction time is not particularly limited and is usually 0.1 to 12 hours, and preferably 3 to 10 hours.

Step 3 Method for Preparing Fumaric Acid Cocrystal Form I of Compound Represented by Formula (VII)

This step is a method for preparing fumaric acid cocrystal Form I of the compound represented by Formula (VII), characterized in that the compound represented by Formula (VII) is crystallized in the presence of fumaric acid, acetone, and water.

Regarding the amount of fumaric acid used, usually, 1.0 equivalent to 3.0 equivalents of fumaric acid, for example, 1.0 equivalents to 1.5 equivalents thereof with respect to the compound represented by Formula (VII) can be used.

The crystallization temperature is not particularly limited, and the crystallization can be usually performed at 40 to 80° C., preferably at 40 to 60° C.

The crystallization time is not particularly limited and is usually 1 hour or longer, preferably 2 hours or longer, and further preferably 2 to 12 hours.

The crystallization may be performed in the presence of acetone and water, and preferably, can be performed at a ratio of acetone:water=85:15 to 50:50.

The compound represented by Formula (VII), its pharmaceutically acceptable salt, or a complex thereof (hereinafter, referred to as a compound represented by Formula (VII) or the like), and the compound produced by the production method according to the present invention (such as the compound represented by Formula (VII)) have coronavirus 3CL protease inhibitory activity, and thus are useful as a therapeutic and/or prophylactic agent for virus disease.

Further, the compound produced by the production method according to the present invention has usefulness as a pharmaceutical preparation and has preferably any or a plurality of the following superior properties.

a) The compound has weak inhibitory activity against CYP enzymes (for example, CYP1A2, CYP2C9, CYP2C19, CYP2D6, CYP3A4, etc.).
b) The compound shows excellent pharmacokinetics such as high bioavailability or moderate clearance.
c) The compound has high metabolic stability.
d) The compound does not show irreversible inhibitory activity against CYP enzymes (for example, CYP3A4) in the range of the concentration of the measurement conditions described herein.
e) The compound does not show mutagenesis.
f) The compound has a low risk of cardiovascular systems.
g) The compound shows high solubility.
h) The compound shows a high protein unbinding ratio (fu value).
i) The compound has high coronavirus 3CL protease selectivity.
j) The compound has high coronavirus replication inhibitory activity. For example, the compound has high coronavirus replication inhibitory activity with addition of human serum (HS) or human serum albumin (has).

Examples of a coronavirus replication inhibitor include embodiments, for example, having $EC_{50}$ of 10 μM or less, preferably 1 μM or less, and more preferably 100 nM or less, for example, in a CPE effect (SARS-CoV-2) described below.

Furthermore, the salt, crystal, complex, cocrystal of the compound according to the present invention have usefulness as a pharmaceutical preparation and has preferably any or a plurality of the following superior properties.

bb) It shows excellent pharmacokinetics such as high bioavailability, moderate clearance, high AUC, or high maximum drug concentration.
gg) It shows high solubility, high chemical stability, and low moisture absorbency.

The pharmaceutical composition comprising the compound represented by Formula (VII) or the like (for example, the compound produced by the production method according to the present invention) can also be administered orally or parenterally. Examples of methods for parenteral administration include dermal, subcutaneous, intravenous, intraarterial, intramuscular, intraperitoneal, transmucosal, inhalation, transnasal, ophthalmic, inner ear or vaginal administration, and the like.

In the case of oral administration, any forms, which are usually used, such as oral solid formulations (for example, tablets, powders, granules, capsules, pills, films, etc.), oral liquid medicine (for example, suspension, emulsion, elixir, syrup, limonade, spirit, aromatic water, extract, decoction, tincture, etc.) and the like may be prepared according to the usual method and administered. The tablets may be sugar-coated tablets, film-coated tablets, enteric-coating tablets, sustained-release tablets, troche tablets, sublingual tablets, buccal tablets, chewable tablets, or orally disintegrated tablets, powders and granules may be dry syrups, and capsules may be soft capsules, micro capsules, or sustained-release capsules.

In the case of parenteral administration, any forms, which are usually used, such as injections, infusion, external preparations (for example, ear drops, nasal drops, eye drops, aerosol, inhalation, lotion, injection agents, coating agents, mouthwash, enemas, ointments, plasters, jellies, creams, patches, cataplasms, external powders, suppositories, etc.) and the like can be preferably administrated. The injections may be emulsions whose type is O/W, W/O, O/W/O, W/O/W, or the like.

The pharmaceutical composition can be produced by mixing an effective amount of the compound represented by Formula (VII) or the like (for example, the compound produced by the production method according to the present invention) with various pharmaceutical additives suitable for forms of the pharmaceutical composition, such as excipients, binders, disintegrants, and lubricants, as necessary. Further, the pharmaceutical composition can also be used for pediatric patients, geriatric patients, serious cases, or operations by appropriately changing the effective amount of the compound of the present invention, forms and/or various pharmaceutical additives. For example, pediatric pharmaceutical compositions may be administered to patients who are neonates (younger than 4 weeks old after the birth), infants (4 weeks old to younger than 1 year old after the birth), children (1 year old or older and younger than 7 years old), infant children (7 years old or older and younger than 15 years old), or 15 to 18 years old. For example, the geriatric pharmaceutical compositions may be administered to patients who are 65 years old or older.

Although it is desirable to set the dose of the pharmaceutical composition comprising the compound represented by Formula (VII) or the like (for example, the compound produced by the production method according to the present invention) (for example, the pharmaceutical composition containing fumaric acid cocrystal Form I of the compound represented by Formula (VII)) in consideration of the age and body weight of the patient, disease type and degree, administration route, and the like, the dose in the case of oral administration is within the range of usually 0.05 to 200 mg/kg/day and preferably 0.1 to 100 mg/kg/day. Although varying depending on the administration route, the dose in the case of parenteral administration is within the range of usually 0.005 to 200 mg/kg/day and preferably 0.01 to 100 mg/kg/day. It may be administered once to several times a day.

The compound represented by Formula (VII) or the like (for example, the compound produced by the production method according to the present invention) may be used, for example, combining other medicaments for treating Novel coronavirus infections (COVID-19) (as the therapeutic agents, including approved medicaments, and medicaments which are under development or will be developed in the future) (hereinafter, referred to as a concomitant medicament) for the purpose of enforcement of the activity of the compound or reduction of the dose of the compound or the like. In this case, timing of administration of the compound of the present invention and the concomitant medicament is not limited and these may be administered to the subject simultaneously or at regular intervals. Further, the compound of the present invention and the concomitant medicament may be administered as two or more kinds of different compositions containing each active ingredient or as a single formulation containing both active ingredient.

The dose of the concomitant medicament can be appropriately selected on the basis of the dose used on clinical. Furthermore, the mixing ratio of the compound of the present invention and a concomitant medicament can be appropriately selected in consideration of the subject of administration, administration route, target diseases, symptoms, combinations, and the like. For example, when the subject of administration is human, the concomitant medicament may be used in the range of 0.01 to 100 parts by weight with respect to 1 part by weight of the compound of the present invention.

The formulation can be produced by mixing an effective amount of the compound represented by Formula (VII) or the like with various pharmaceutical additives suitable for forms of the formulation, such as excipients, binders, disintegrants, and lubricants, as necessary.

The formulation of the present invention may be a formulation to be orally administered. In the case of oral administration, any forms, which are usually used, such as oral solid formulations (for example, tablets, powders, granules, dry syrup, capsules, pills, films, etc.), oral liquid medicine (for example, suspension, emulsion, elixir, syrup, limonade, spirit, aromatic water, extract, decoction, tincture, etc.) and the like may be prepared according to the usual method and administered. The tablets may be sugar-coated tablets, film-coated tablets, enteric-coating tablets, sustained-release tablets, troche tablets, sublingual tablets, buccal tablets, chewable tablets, or orally disintegrated tablets, powders and granules may be dry syrups, and capsules may be soft capsules, micro capsules, or sustained-release capsules. The formulation is preferably a solid formulation or suspension to be orally administered, more preferably a solid formulation to be orally administered, and particularly preferably a tablet or granule.

Regarding the shape of the tablet, any shape can be adopted; specifically, the tablet can be formed into a shape of a circle, an ellipse, a sphere, a bar, or a donut. Furthermore, the tablet may be a multi-layer tablet, a dry-coated tablet, and the like, but is preferably a single-layer tablet, which is produced easily. Further, impression such as a mark and a letter for improving discriminability, or a cleavage line for division may be imparted.

Further, the formulation of the present invention can also be used for pediatric patients, geriatric patients, serious cases, or operations by appropriately changing the effective amount of the compound represented by Formula (VII) or the like, forms and/or various pharmaceutical additives. For example, pediatric pharmaceutical compositions may be administered to patients who are neonates (younger than 4 weeks old after the birth), infants (4 weeks old to younger than 1 year old after the birth), children (1 year old or older and younger than 7 years old), infant children (7 years old or older and younger than 15 years old), or 15 to 18 years old. For example, the geriatric formulations may be administered to patients who are 65 years old or older.

Although it is desirable to set the dose of the formulation of the present invention (for example, the formulation containing fumaric acid cocrystal Form I of the compound represented by Formula (VII)) in consideration of the age and body weight of the patient, disease type and degree, administration route, and the like, the dose in the case of oral administration is within the range of usually 0.05 to 200 mg/kg/day and preferably 0.1 to 100 mg/kg/day. Although varying depending on the administration route, the dose in the case of parenteral administration is within the range of usually 0.005 to 200 mg/kg/day and preferably 0.01 to 100 mg/kg/day. It may be administered once to several times a day.

The weight of the compound represented by Formula (VII) or the like, which is contained in the formulation of the present invention, is not particularly limited as long as it is such a content that is easily taken by patients and enables the formulation to be produced, and is 1 to 450 mg, preferably 5 to 350 mg, and more preferably 25 to 250 mg.

Specifically, the weight of the compound represented by Formula (VII) or the like, which is contained per tablet, capsule, or pack, is 25 mg, 50 mg, 75 mg, 100 mg, 125 mg, 150 mg, 175 mg, 200 mg, 225 mg, or 250 mg.

In this case, 25 mg indicates a range of 22.5 mg to 27.5 mg, preferably a range of 23.7 mg to 26.3 mg, 50 mg indicates a range of 45.0 mg to 55.0 mg, preferably a range of 47.5 mg to 52.5 mg, 75 mg indicates a range of 67.5 mg to 82.5 mg, preferably a range of 71.2 mg to 78.8 mg, 100 mg indicates a range of 90.0 mg to 110.0 mg, preferably a range of 95.0 mg to 105.0 mg, 125 mg indicates a range of 112.5 mg to 137.5 mg, preferably a range of 118.7 mg to 131.3 mg, 150 mg indicates a range of 135.0 mg to 165.0 mg, preferably a range of 142.5 mg to 157.5 mg, 175 mg indicates a range of 157.5 mg to 192.5 mg, preferably a range of 166.2 to 183.8 mg, 200 mg indicates a range of 180.0 mg to 220.0 mg, preferably a range of 190.0 mg to 210.0 mg, 225 mg indicates a range of 202.5 mg to 247.5 mg, preferably a range of 213.7 mg to 236.3 mg, and 250 mg indicates a range of 225.0 mg to 275.0 mg, preferably a range of 237.5 mg to 262.5 mg.

The compound represented by Formula (VII) or the like may be used, for example, combining other medicaments for treating Novel coronavirus infections (COVID-19) (as the therapeutic agents, including approved medicaments, and medicaments which are under development or will be developed in the future) (hereinafter, referred to as a concomitant medicament) for the purpose of enforcement of the activity of the compound or reduction of the dose of the compound or the like. In this case, timing of administration of the compound represented by Formula (VII) or the like and the concomitant medicament is not limited and these may be administered to the subject simultaneously or at regular intervals. Further, the compound represented by Formula (VII) or the like and the concomitant medicament may be administered as two or more kinds of different formulations containing each active ingredient or as a single formulation containing both active ingredient.

The dose of the concomitant medicament can be appropriately selected on the basis of the dose used on clinical. Furthermore, the mixing ratio of the compound represented by Formula (VII) or the like and the concomitant medicament can be appropriately selected in consideration of the subject of administration, administration route, target diseases, symptoms, combinations, and the like. For example, when the subject of administration is human, the concomitant medicament may be used in the range of 0.01 to 100 parts by weight with respect to 1 part by weight of the compound represented by Formula (VII) or the like.

The formulation of the present invention may comprise a polymer, and as the polymer, polymers described in Japanese Pharmacopoeia, Pharmaceutical Standards outside the Japanese Pharmacopoeia, Japanese Pharmaceutical Excipients, Japanese Standard of Food Additives, or the like can be used.

The formulation comprising the compound represented by Formula (VII), its pharmaceutically acceptable salt, or a complex thereof, and a polymer can improve the solubility of the compound represented by Formula (VII) in the formulation.

Examples of the polymer include a cellulose-based polymer, an acrylic polymer, a vinyl-based polymer, and polysaccharides.

Examples of the cellulose-based polymer include hydroxypropylcellulose (HPC), hypromellose (hydroxypropylmethylcellulose) (HPMC), hydroxyethyl cellulose, hydroxyethylmethylcellulose, hydroxypropylmethylcellulose acetate succinate, hydroxypropylmethylcellulose, phthalate, methylcellulose (MC), methylhydroxyethylcellulose carboxymethylethylcellulose, ethylcellulose, crystalline cellulose, microcrystalline cellulose, crystalline cellulose-carmellose sodium, carmellose, carmellose sodium, carmellose calcium, powder cellulose, low-substituted hydroxypropylcellulose, and fumaric acid-stearic acid-polyvinyl acetal diethylaminoacetate-hydroxypropyl methylcellulose mixture.

Examples of the acrylic polymer include aminoalkyl acrylate copolymer E, polyvinyl acetal diethylaminoacetate, ethyl acrylate-methyl methacrylate copolymer dispersion, aminoalkyl methacrylate copolymer, methacrylic acid copolymer, 2-methyl-5-vinyl pyridine methyl acrylate-methacrylic acid copolymer, dry methacrylic acid copolymer, and dimethylamino ethyl methacrylate-methyl methacrylate copolymer.

Examples of the vinyl-based polymer include polyvinylpyrrolidone, polyvinyl alcohol, polyvinyl alcohol-methyl methacrylate-acrylic acid copolymer, crospovidone, carboxy vinyl polymer, polyvinyl acetal diethylaminoacetate, and polyvinyl alcohol copolymer.

Furthermore, examples of the polysaccharides include pullulan.

The polymer is preferably a cellulose-based polymer, an acrylic polymer, and/or a vinyl-based polymer, more preferably a cellulose-based polymer, and further preferably hypromellose (hydroxypropyl methylcellulose).

Another embodiment is preferably a tablet for oral administration, comprising a compound represented by Formula (VII), its pharmaceutically acceptable salt, or a complex thereof as an active ingredient, and a cellulose-based polymer.

In the formulation of the present invention, one or more additives selected from the group consisting of an excipient, a binder, a disintegrant, and a lubricant may be used.

In the formulation of the present invention, an excipient (also referred to as a filler in some cases) may be used. As the excipient, excipients described in Japanese Pharmacopoeia, Pharmaceutical Standards outside the Japanese Pharmacopoeia, Japanese Pharmaceutical Excipients, Japanese Standard of Food Additives, or the like can be used. Examples of the excipient include sugar derivatives, starch derivatives, cellulose derivatives, inorganic excipients, β-cyclodextrin, magnesium stearate, calcium stearate, sucrose fatty acid ester, crospovidone, soybean lecithin, powdered tragacanth, gum arabic, dextran, and pullulan.

Examples of the sugar derivatives include sugars and sugar alcohols, examples of the sugars include lactose, white soft sugar, glucose, fructose, and sucrose, and examples of the sugar alcohols include mannitol, sorbitol, erythritol, xylitol, powdered maltose starch syrup, and maltitol.

Examples of the starch derivatives include starch, potato starch, corn starch (cornstarch), rice starch, partly pregelatinized starch, pregelatinized starch, porous starch, carboxystarch sodium, hydroxypropyl starch, and low-substituted sodium carboxymethyl starch.

Examples of the cellulose derivatives include crystalline cellulose, powder cellulose, carmellose sodium, carmellose, croscarmellose sodium, carmellose calcium, carboxymethylethylcellulose, and low-substituted hydroxypropylcellulose.

Examples of the inorganic excipients include silicate derivatives, phosphate, carbonates, sulfates, magnesium oxide, titanium oxide, calcium lactate, synthetic hydrotalcite, talc, kaolin, dried aluminum hydroxide, magnesium oxide, and bentonite.

Examples of the silicate derivatives include silicon dioxides such as hydrated silicon dioxide and light anhydrous silicic acid, magnesium aluminometasilicate, synthetic aluminum silicate, and calcium silicate.

Examples of the phosphate include anhydrous dibasic calcium phosphate, calcium monohydrogen phosphate, calcium hydrogen phosphate, sodium hydrogen phosphate, dipotassium phosphate, potassium dihydrogen phosphate, calcium dihydrogen phosphate, and monobasic sodium phosphate.

Examples of the carbonates include precipitated calcium carbonate, calcium carbonate, and magnesium carbonate. Examples of the sulfates include calcium sulfate.

Two or more kinds of these excipients may be mixed at an appropriate ratio and then used.

The excipient in the formulation of the present invention is preferably mannitol and/or croscarmellose sodium.

In the formulation of the present invention, a binder may be used, and binders described in Japanese Pharmacopoeia, Pharmaceutical Standards outside the Japanese Pharmacopoeia, Japanese Pharmaceutical Excipients, Japanese Standard of Food Additives, or the like can be used. Examples of the binder include a cellulose-based binder, a starch-based binder, a vinyl-based binder, polyether, gum arabic, gum arabic powder, powdered acacia, alginic acid, sodium alginate, sucrose, gelatin, dextrin, pullulan, tragacanth, powdered tragacanth, xanthane gum, pectin, sodium polyacrylate, agar, powdered phellodendron bark, guar gum, light anhydrous silicic acid, and hardened oil.

Examples of the cellulose-based binder include carboxymethylcellulose (carmellose, CMC), carboxymethylcellulose sodium (carmellose sodium), hydroxyethyl cellulose (HEC), hydroxypropylcellulose (HPC), hydroxypropyl methylcellulose (hypromellose) (HPMC), methylcellulose (MC), crystalline cellulose, microcrystalline cellulose, ethylcellulose, crystalline cellulose-carmellose sodium, carmellose calcium, powder cellulose, and low-substituted hydroxypropylcellulose.

Examples of the starch-based binder include starch, pregelatinized starch, partly pregelatinized starch, potato starch, wheat starch, rice starch, porous starch, corn starch, hydroxypropyl starch, sodium starch glycolate (sodium carboxymethyl starch).

Examples of the vinyl-based binder include polyvinyl alcohol (PVA), polyvinylpyrrolidone (povidone) (PVP), carboxy vinyl polymer, and copolyvidone.

Examples of the polyether include Macrogol (polyethylene glycol) 200, Macrogol 300, Macrogol 400, Macrogol 600, Macrogol 1000, Macrogol 1500, Macrogol 1540, Macrogol 4000, Macrogol 6000, Macrogol 20000, glycerin, polyoxyethylene [105] polyoxypropylene [5] glycol, and propylene glycol.

Two or more kinds of these binders may be mixed at an appropriate ratio and then used.

The binder in the formulation of the present invention is preferably hydroxypropylcellulose (HPC).

In the formulation of the present invention, a disintegrant may be used, and disintegrants described in Japanese Pharmacopoeia, Pharmaceutical Standards outside the Japanese Pharmacopoeia, Japanese Pharmaceutical Excipients, Japanese Standard of Food Additives, or the like can be used. Examples of the disintegrant include a cellulose-based disintegrant, a starch-based disintegrant, a vinyl-based disintegrant, and magnesium aluminometasilicate.

Examples of the cellulose-based disintegrant include carmellose, carmellose calcium, carmellose sodium, hydroxypropylcellulose, low-substituted hydroxypropylcellulose, croscarmellose sodium (Ac-Di-Sol), crystalline cellulose, and powder cellulose.

Examples of the starch-based disintegrant include partly pregelatinized starch, potato starch, cornstarch, hydroxypropyl starch, sodium carboxymethyl starch, low-substituted sodium carboxymethyl starch, sodium starch glycolate, pregelatinized starch, and starch.

Examples of the vinyl-based disintegrant include crospovidone and polyvinyl alcohol.

Two or more kinds of these disintegrants may be mixed at an appropriate ratio and then used.

Among disintegrants, a swelling disintegrant having an extremely large swelling rate is known as a "super disintegrant". Examples of the super disintegrant include carmellose calcium, low-substituted hydroxypropylcellulose, croscarmellose sodium, crospovidone, and sodium starch glycolate.

Two or more kinds of these super disintegrants may be mixed at an appropriate ratio and then used. Furthermore, a disintegrant and a super disintegrant may be combined.

The disintegrant in the formulation of the present invention is preferably croscarmellose sodium.

In the formulation of the present invention, a lubricant may be contained, and lubricants described in Japanese Pharmacopoeia, Pharmaceutical Standards outside the Japanese Pharmacopoeia, Japanese Pharmaceutical Excipients, Japanese Standard of Food Additives, or the like can be used. Examples of the lubricant include stearic acid and metallic stearate, an inorganic lubricant, a hydrophobic lubricant, a hydrophilic lubricant, and sodium stearyl fumarate.

Examples of the stearic acid and metallic stearate include magnesium stearate, calcium stearate, stearic acid, stearyl alcohol, and polyoxyl 40 stearate.

Examples of the inorganic lubricant include talc, light anhydrous silicic acid, hydrated silicon dioxide, magnesium carbonate, precipitated calcium carbonate, dried aluminum hydroxide gel, magnesium aluminometasilicate, magnesium silicate, synthetic aluminum silicate, magnesium oxide, and magnesium sulfate.

Examples of the hydrophobic lubricant include cacao butter, carnauba wax, glycerin fatty acid ester, hardened oil, white beeswax, soybean hardened oil, beeswax, cetanol, and sodium laurate.

Examples of the hydrophilic lubricant include sucrose fatty acid ester and polyethylene glycol (Macrogol).

Two or more kinds of these lubricants may be mixed at an appropriate ratio and then used.

The binder in the formulation of the present invention is preferably magnesium stearate.

In the formulation of the present invention, a fluidizer may be contained, and fluidizers described in Japanese Pharmacopoeia, Pharmaceutical Standards outside the Japanese Pharmacopoeia, Japanese Pharmaceutical Excipients, Japanese Standard of Food Additives, or the like can be used. Examples of the fluidizer include silicon dioxide, stearic acid and a metallic salt thereof, crystalline cellulose, synthetic aluminum silicate, titanium oxide, heavy anhydrous silicic acid, alumina magnesium hydroxide, tribasic calcium phosphate, talc, corn starch, magnesium aluminometasilicate, granular calcium hydrogen phosphate, calcium silicate, anhydrous dibasic calcium phosphate, and synthetic hydrotalcite.

Examples of the silicon dioxide include hydrated silicon dioxide and light anhydrous silicic acid. Examples of the stearic acid and the metallic salt thereof include stearic acid, calcium stearate, and magnesium stearate.

Two or more kinds of these fluidizers may be mixed at an appropriate ratio and then used.

The binder in the formulation of the present invention is preferably crystalline cellulose.

A method for producing granules of the formulation of the present invention is not particularly limited, but is specifically a method of mixing active ingredients and additives such as a disintegrant and an excipient to produce a mixed powder and then granulating the mixed powder, preferably a wet granulation method of performing granulation by adding water, water or a solvent containing a binder, or a dry granulation method or melt granulation method which perform compression molding without water.

A method for producing tablets of the formulation of the present invention is not particularly limited, but is specifically a tableting method in which granules are produced by the above-described method, a disintegrant and a lubricant are further mixed with the granules, and the mixed granules are tableted by a tablet machine.

As for the formulation of the present invention, after producing the above granules or tablets, the granules or tablets may be coated with a coating layer. When forming a coating layer on the granules, a fluidized-bed granulator coating machine, a fluidized-bed tumbling coating machine, and the like can be used. When forming a coating layer on the tablets, a pan coating machine, an aerated coating machine, and the like can be used. While the granules or tablets are fluidized in a coating machine, the coating solution is sprayed to the granules or tablets and dried so as to form a coating layer.

EXAMPLES

The present invention will be described in more detail below by way of Examples and Reference Examples, as well as Test Examples; however, the present invention is not limited thereto.

Furthermore, the meaning of each abbreviation used herein is as follows.

Boc: tert-butoxycarbonyl
CDI: carbonyldiimidazole
DBU: 1,8-diazabicyclo[5.4.0]-7-undecene
DIEA: N,N-diisopropylethylamine
DMA: N,N-dimethylacetamide
DMF: N,N-dimethylformamide
DMSO: dimethyl sulfoxide
DTT: dithiothreitol
EDC: 1-ethyl-3-(3-dimethylaminopropyl)carbodiimide
EDT: 1,2-ethanedithiol
EDTA: ethylenediaminetetraacetic acid
FBS: fetal bovine serum
HOBT: 1-hydroxybenzotriazole
LHMDS: lithium bis(trimethylsilyl)amide
MEM: Eagle's minimum essential medium
NMP: N-methylpyrrolidone
$Pd(OAc)_2$: palladium acetate
TFA: trifluoroacetic acid
TMSCl: chlorotrimethylsilane
Xantphos: 4,5'-bis(diphenylphosphino)-9,9'-dimethylxanthene
mM: mmol/L
μM: μmol/L
nM: nmol/L

Example a (Method for Identifying Compounds)

NMR analysis obtained in each Example was performed at 400 MHz, and measurement was made using DMSO-$d_6$, $CDCl_3$, and Methanol-$d_4$. Furthermore, in NMR data shown in Examples and Reference Examples, not all measured peaks may be described.

"RT" means retention time in LC/MS: liquid chromatography/mass spectrometry and measured under the following conditions.

(Measurement Conditions 1')

Column: ACQUITY UPLC (registered trademark) BEH C18 (1.7 μm i.d. 2.1×50 mm) (Waters)
Flow rate: 0.8 mL/min
UV detection wavelength: 254 nm
Mobile phases: [A] is a 0.1% formic acid-containing aqueous solution, and [B] is a 0.1% formic acid-containing acetonitrile solution
Gradient: Linear gradient of 5% to 100% solvent [B] for 3.5 minutes was performed, and then 100% solvent [B] was maintained for 0.5 minutes.

(Measurement Conditions 2')

Column: Shim-pack XR-ODS (2.2 μm, i.d. 3.0×50 mm) (Shimadzu)
Flow rate: 1.6 mL/min
UV detection wavelength: 254 nm
Mobile phases: [A] is a 0.1% formic acid-containing aqueous solution, and [B] is a 0.1% formic acid-containing acetonitrile solution
Gradient: Linear gradient of 10% to 100% solvent [B] for 3 minutes was performed, and 100% solvent [B] was maintained for 0.5 minutes.

Note that, herein, the description MS (m/z) indicates the value observed in the mass spectrometry.

(HPLC Measurement Conditions)

Column: Xselect CSH Fluoro-Phenyl (3.5 μm i.d. 4.6×150 mm) (Waters)
Column temperature: constant temperature at near 40° C.
UV detection wavelength: 255 nm
Mobile phases: [A] is a 0.1% formic acid-containing aqueous solution, and [B] is acetonitrile for liquid chromatography
Gradient: 20% solvent [B] was maintained for 2 minutes, linear gradient of 20% to 37% solvent [B] for 6 minutes was performed, linear gradient of 37% to 50% solvent [B] for 10 minutes was performed, and linear gradient of 50% to 95% solvent [B] for 2 minutes was performed.

Flow rate: 1.0 mL/min

Injection amount: 10 μL (X-Ray Powder Diffraction Pattern Measurement)

X-ray powder diffraction pattern measurement of crystals obtained in each Example was performed according to a powder X-ray diffraction measurement method described in General Tests in Japanese Pharmacopoeia. Measurement conditions are as follows.

(Device)

SmartLab manufactured by Rigaku Corporation (Operation Method)

Measuring method: reflection method

Wavelength used: CuKα ray

Tube current: 200 mA

Tube voltage: 45 kV

Sampling plate: aluminum

X-ray incident angle: 2.5°

Sampling width: 0.02°

Detector: HyPix-3000 (two-dimensional detection mode)

(Measurement of Differential Scanning Calorimetry (DSC))

DSC measurement of crystals obtained in Examples was performed. About 3 mg of a sample was weighed into an aluminum pan, crimped, and DSC measurement was performed. Measurement conditions are as follows. Incidentally, in the measurement made by differential scanning calorimetry (DSC), an error can occur in the range of ±2° C.

Device: TA Instrument Q1000/TA Instrument

Measurement temperature range: 0° C. to 295° C.

Rate of temperature increase: 10° C./min

Atmosphere: $N_2$ 50 mL/min (Measurement of TG/DTA Data)

About 3 mg of the crystals obtained in Examples were weighed and packed into an aluminum pan, and measurement was performed in an open system.

Measurement conditions are as follows.

Device: Hitachi High-Technologies TG/DTA STA7200RV

Measurement temperature range: Room temperature to 350° C.

Rate of temperature increase: 10° C./min (Moisture Sorption/Desorption Isotherm Measurement)

About 15 to 25 mg of a sample was weighed into a sample pan, and measurement was made. Measurement conditions are as follows.

Device: DVS Adventure manufactured by Surface Measurement Systems Ltd.

Measurement points: 0% to 95% RH every 5%, and 95% RH to 0% every 5%

Temperature: 25° C.

(Measurement of Single Crystal Structural Analysis and Analysis Method)

The measurement conditions of the single crystal structural analysis and the analysis method are as follows.

(Device)

XtaLAB P200 MM007 manufactured by Rigaku Corporation (Measurement Conditions)

Measurement temperature: 25° C.

Wavelength used: CuKα ray (λ=1.5418 Å)

Software: CrysAlisPro 1.171.39.46e (Rigaku Oxford Diffraction, 2018)

(Data Processing)

Software: CrysAlisPro 1.171.39.46e (Rigaku Oxford Diffraction, 2018)

The data were corrected for the Lorentz, polarization and absorption effects.

(Crystal Structural Analysis)

The phase determination was performed by using the direct method program ShelXT (Sheldrick, G. M., 2015), and the structural refinement by full-matrix least-square method was then performed by using ShelXL (Sheldrick, G. M., 2015). All temperature factors of non-hydrogen atoms were refined with anisotropic parameters. Hydrogen atoms were placed by calculation using default parameters of ShelXL and regarded as riding atom. All hydrogen atoms were refined with isotropic parameters.

Figures were made using PLATON (Spek, 1991)/ORTEP (Johnson, 1976).

Example 1a

Synthesis of Compound (I-005)

[Chemical Formula 33]

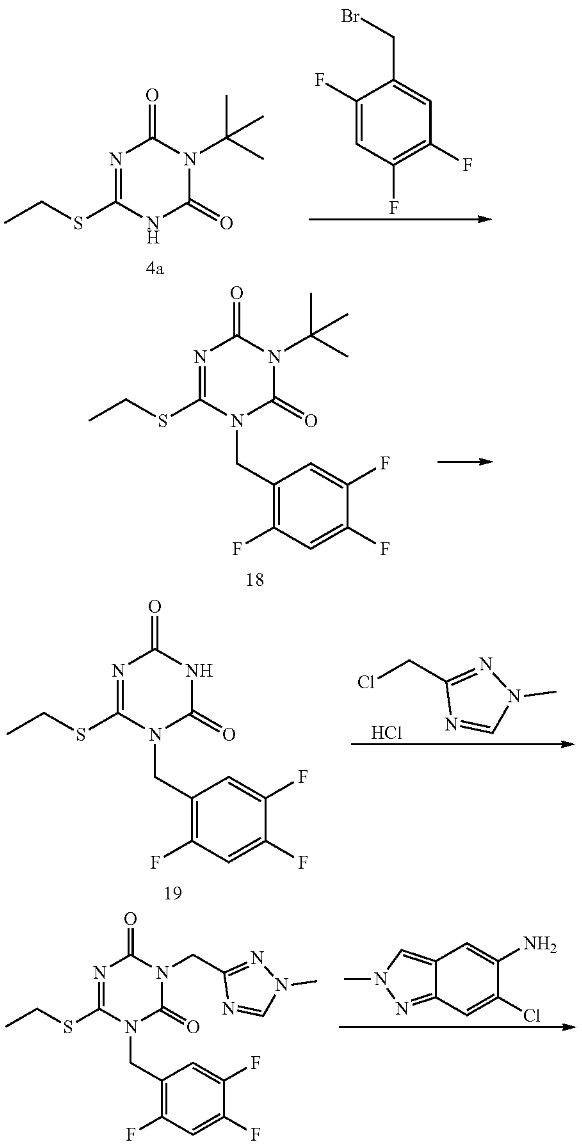

4a

18

19

20

-continued

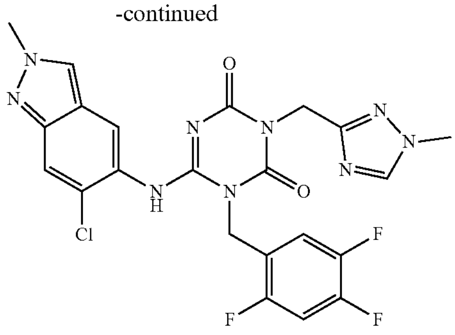

I-005

Step 1 Synthesis of Compound 18

Compound 4a (926 mg, 4.04 mmol), acetonitrile (7.41 mL), potassium carbonate (726 mg, 5.25 mmol), and 2,4,5-trifluorobenzyl bromide (1000 mg, 4.44 mmol) were mixed. The reaction solution was stirred at 80° C. for 40 minutes, left to be cooled, and then diluted with ethyl acetate. The insoluble matters were filtered, and the filtrate was concentrated, to give a crude product (1.51 g, 4.04 mmol, yield: quantitative) of Compound 18.

LC/MS (ESI): m/z=374, RT=2.54 min, LC/MS measurement conditions 1'

Step 2 Synthesis of Compound 19

Compound 18 (1.51 g, 4.04 mmol) and TFA (3.02 mL) were mixed. The reaction solution was stirred at room temperature for 4 hours and left to stand still overnight. TFA was distilled under reduced pressure, and the residue was azeotropically distilled by adding toluene thereto. The residue was suspended in isopropyl ether and then collected by filtration, to give Compound 19 (1.22 g, 3.84 mmol, yield 95%).

LC/MS (ESI): m/z=318, RT=1.68 min, LC/MS measurement conditions 1'

Step 3 Synthesis of Compound 20

Compound 19 (200 mg, 0.63 mmol), DMF (1.8 mL), potassium carbonate (261 mg, 1.89 mmol), and 3-(chloromethyl)-1-methyl-1H-1,2,4-triazole hydrochloride (159 mg, 0.946 mmol) were mixed. The reaction solution was stirred at 60° C. for 2 hours, and a saturated ammonium chloride aqueous solution was added thereto. The aqueous layer was extracted with ethyl acetate, and the organic layer was washed with saturated saline. The organic layer was dried with magnesium sulfate, filtered, and concentrated. The residue was suspended in a mixed solvent of isopropyl ether, hexane, ethyl acetate, and chloroform and collected by filtration. The residue, DMF (1.8 mL), potassium carbonate (261 mg, 1.89 mmol), and 3-(chloromethyl)-1-methyl-1H-1,2,4-triazole hydrochloride (159 mg, 0.946 mmol) were mixed. The reaction solution was stirred at 60° C. for 6 hours, and a saturated ammonium chloride aqueous solution was added thereto. The aqueous layer was extracted with ethyl acetate, and the organic layer was washed with saturated saline. The organic layer was dried with magnesium sulfate, filtered, and concentrated. The residue was suspended in a mixed solvent of isopropyl ether, hexane, ethyl acetate, and chloroform and collected by filtration, to give Compound 20 (116 mg, 0.281 mmol, yield 45%)

LC/MS (ESI): m/z=413, RT=1.84 min, LC/MS measurement conditions 1'

Step 4 Synthesis of Compound (I-005)

Figure 7:
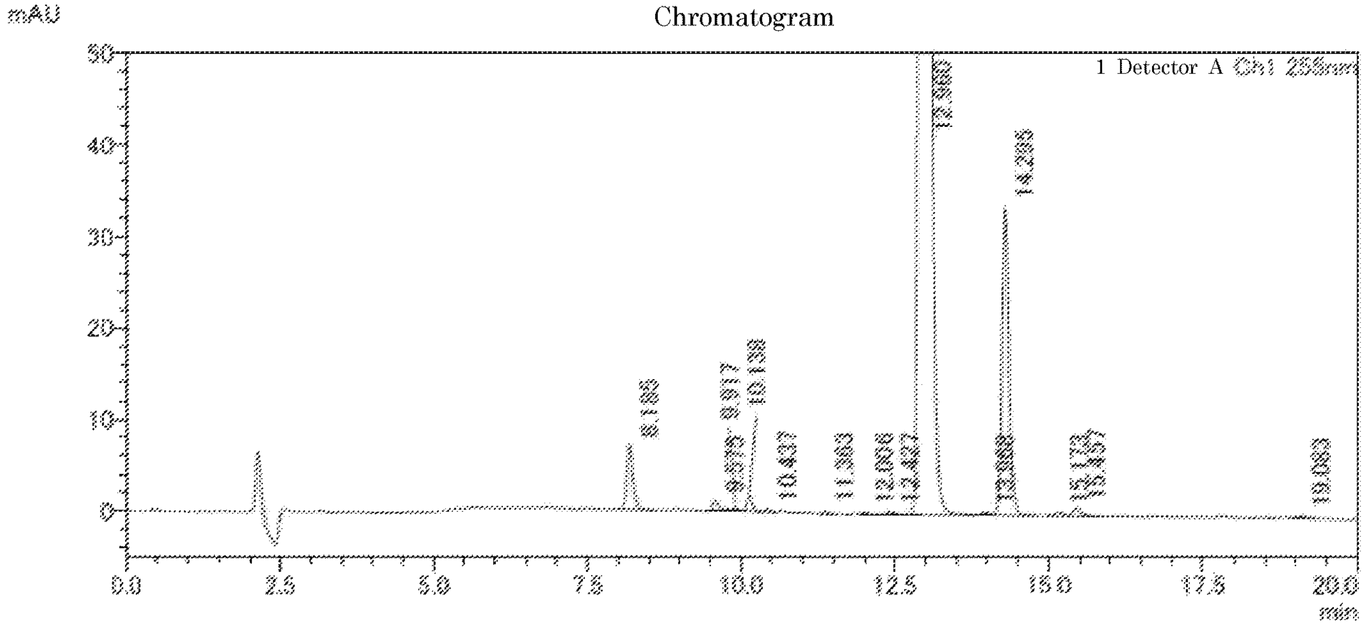
FIG. 7 shows HPLC measurement results of Compound I-005 obtained in Step 4 of Example 1a. The pa % (peak area %) of the compound represented by Formula (VII) (Compound I-005) was about 95 pa %.

Compound 20 (115 mg, 0.279 mmol), THF (2.30 mL), and 6-chloro-2-methyl-2H-indazole-5-amine (60.8 mg, 0.335 mmol) were mixed. LHMDS (558 μL, 0.558 mmol) was added dropwise at 0° C. to the reaction solution. The reaction solution was stirred at 0° C. for 2.5 hours and stirred at room temperature for 40 minutes, and a saturated ammonium chloride aqueous solution was added thereto. The aqueous layer was extracted with chloroform, and the organic layer was concentrated. The residue was purified with silica gel column chromatography (chloroform/methanol), to give Compound (I-005) (61.8 mg, 0.116 mmol, yield 42%). The HPLC measurement results of the obtained Compound I-005 are shown in FIG. 7.

$^1$H-NMR ($CDCl_3$) δ: 7.96 (s, 1H), 7.82 (d, J=2.5 Hz, 2H), 7.48 (br s, 1H), 7.45-7.37 (m, 1H), 7.08 (s, 1H), 6.97-6.88 (m, 1H), 5.35 (s, 2H), 5.17 (s, 2H), 4.21 (s, 3H), 3.89 (s, 3H).

LC/MS (ESI): m/z=532, RT=1.70 min, LC/MS measurement conditions 1'

Example 2a

To Compound (I-005, 1170 mg) were added fumaric acid (278 mg, 1.1 eq) and ethyl acetate (5.85 mL). The mixture was stirred at room temperature for 45 minutes. The resulting solids were collected by filtration and dried to give fumaric acid cocrystal Form I of the compound represented by Formula (VII) (1369.4 mg, 94.6%).

The result of the single crystal structural analysis of fumaric acid cocrystal Form I of the compound represented by Formula (VII) is shown below.

R1 (I>2.00s(I)) was 0.0470, and it was confirmed that there is neither a lack of electronic density neither misplacing of atom from final difference Fourier.

Crystallographic data are shown in Table 1.

TABLE 1

| Space group | P-1 |
|---|---|
| a (Å) | 8.4374(2) |
| b (Å) | 11.6780(3) |
| c (Å) | 15.1612(4) |
| α (°) | 83.827(2) |
| β (°) | 78.868(2) |
| γ (°) | 77.147(2) |
| Volume (Å$^3$) | 1425.77(6) |
| Z | 2 |
| Density (calculated value) (g/cm$^3$) | 1.509 |
| Measurement temperature (K) | 298 |

Herein, Volume means the unit lattice volume, and Z means the number of molecules in the unit lattice.

Figure 3:
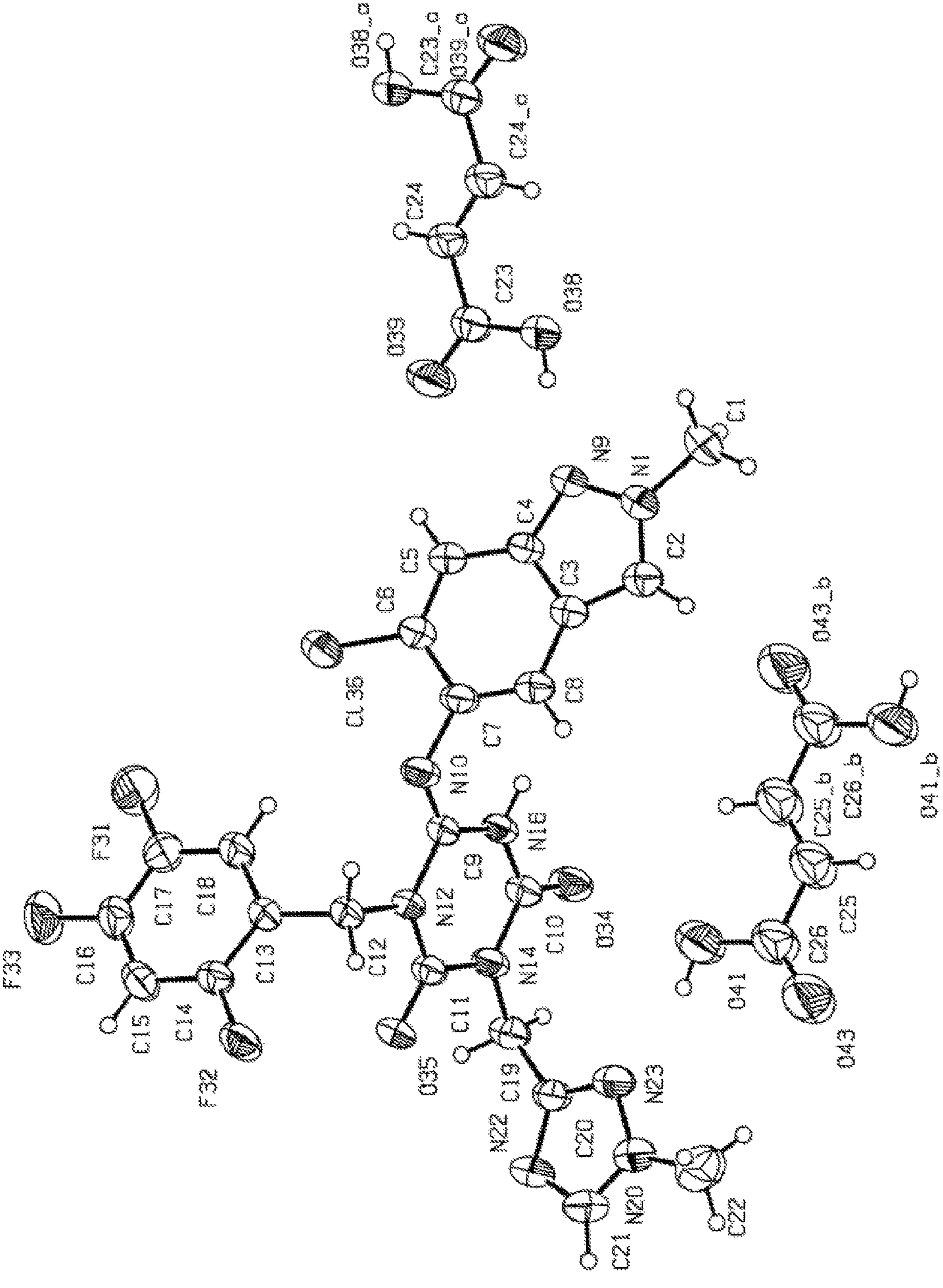
FIG. 3 shows a structure of fumaric acid cocrystal Form I (Form I) of the compound represented by Formula (VII) in an asymmetric unit.

The structure of the fumaric acid cocrystal Form I of the compound represented by Formula (VII) in the asymmetric unit is shown in FIG. 3.

One molecule of each of the compound represented by Formula (VII) and fumaric acid was present in the asymmetric unit. The ionic chemical interaction was not confirmed, and the structure was confirmed to be a cocrystal in a molar ratio of 1:1.

The bond length of N10-C9 was about 1.26 Å, and the bond length of N16-C9 was about 1.37 Å. From this bond length, the compound represented by Formula (VII) of the fumaric acid cocrystal Form I was identified to have an imino structure:

[Chemical Formula 34]

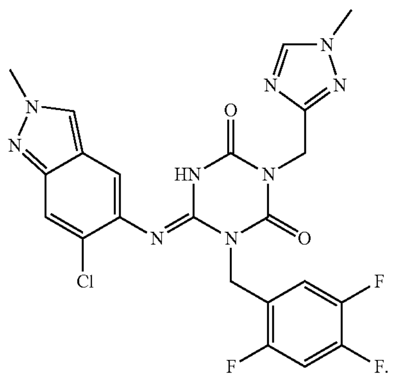

Furthermore, the result of the X-ray powder diffraction of fumaric acid cocrystal Form I of the compound represented by Formula (VII) is shown.

FIG. 1 shows X-ray powder diffraction patterns of fumaric acid cocrystal Form I (Form I) of the compound represented by Formula (VII). The peak table of the X-ray powder diffraction patterns of FIG. 1 is shown in FIG. 2.

In the X-ray powder diffraction pattern, the peaks were observed at the diffraction angle (2θ): 7.8±0.2°, 9.5±0.2°, 10.1±0.2°, 10.9±0.2°, 13.8±0.2°, 14.7±0.2°, 18.6±0.2°, 22.6±0.2°, 23.5±0.2°, and 24.6±0.2°.

In the above-described X-ray powder diffraction peaks, the peaks of the diffraction angle (2θ): 9.5±0.2°, 10.9±0.2°, 18.6±0.2°, 23.5±0.2°, and 24.6±0.2° are particularly characteristic as the fumaric acid cocrystal Form I of the compound represented by Formula (VII).

Figure 4:
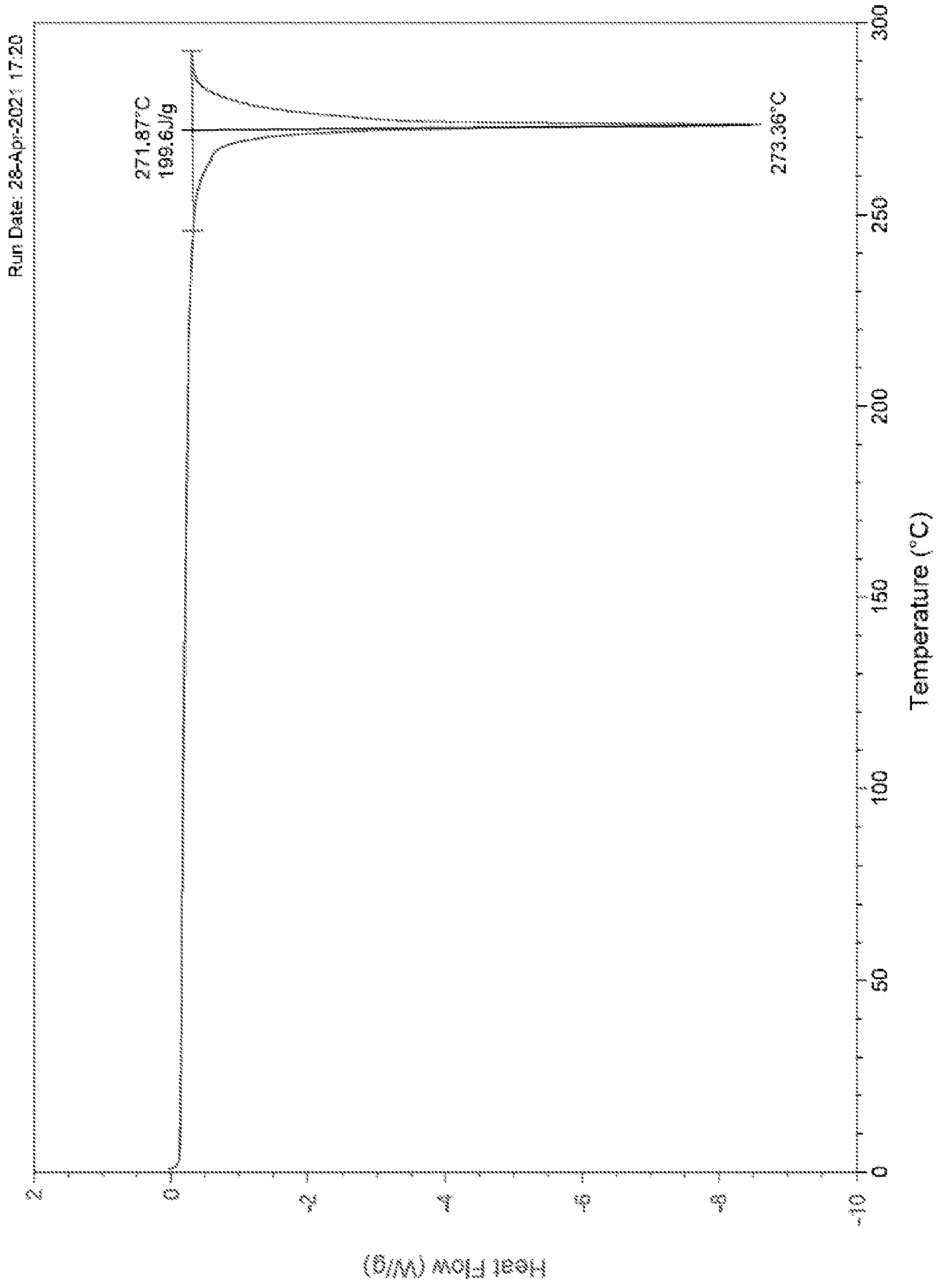
FIG. 4 shows DSC analysis results of fumaric acid cocrystal Form I (Form I) of the compound represented by Formula (VII), which showed the X-ray powder analysis patterns of FIG. 1. The horizontal axis represents temperature (° C.), and the vertical axis represents heat flow (W/g).

FIG. 4 shows DSC analysis results of fumaric acid cocrystal Form I of the compound represented by Formula (VII), which showed the X-ray powder analysis patterns of FIG. 1. The onset temperature of the endothermic peak was about 272° C.

Figure 5:
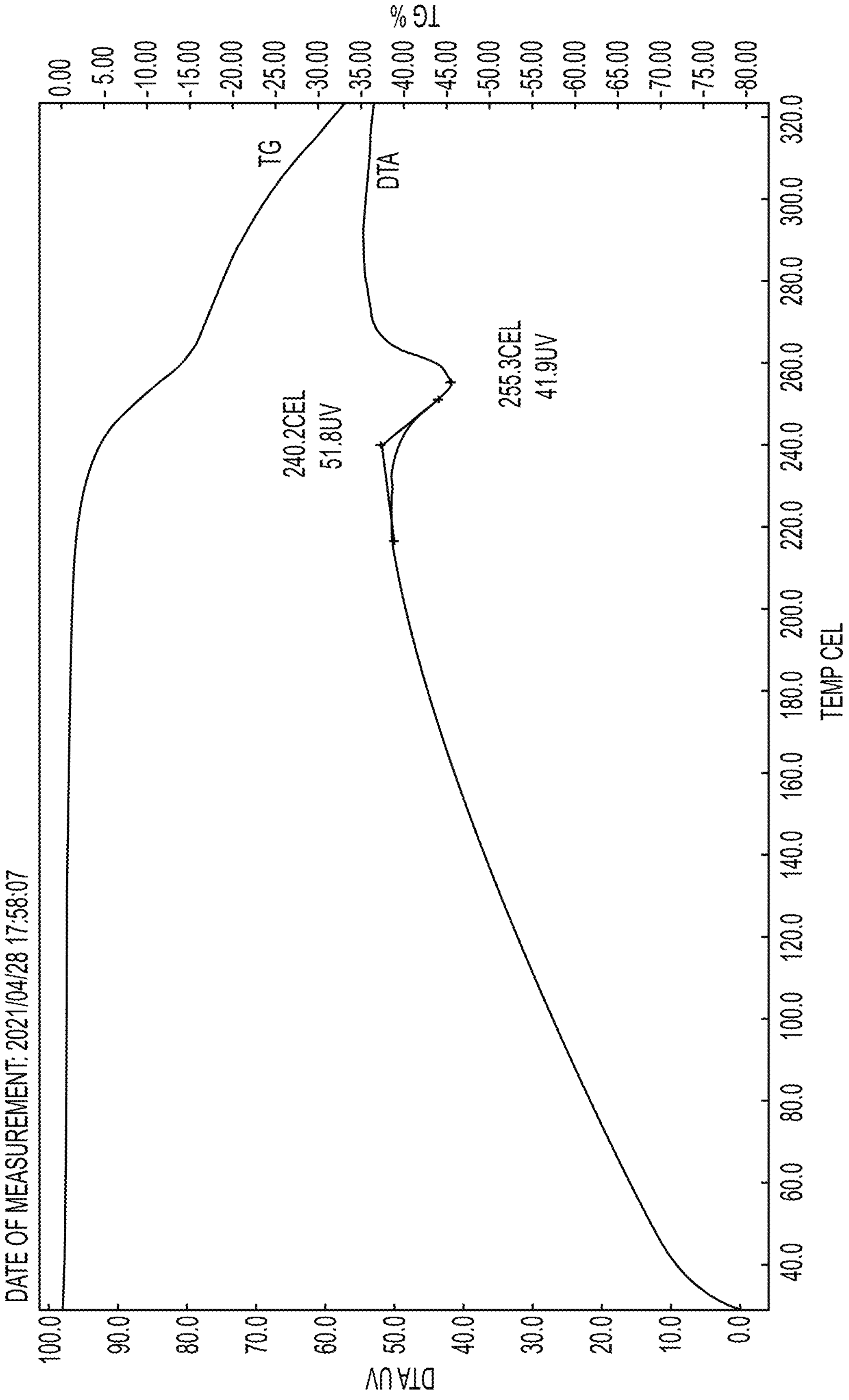
FIG. 5 shows TG/DTA analysis results of fumaric acid cocrystal Form I (Form I) crystal of the compound represented by Formula (VII), which showed the X-ray powder analysis patterns of FIG. 1. The vertical axis represents heat flow (μV) or change in mass (%), and the horizontal axis represents temperature (° C.). Cel in the diagram means degree Celsius (° C.).

FIG. 5 shows TG/DTA analysis results of fumaric acid cocrystal Form I (Form I) of the compound represented by Formula (VII), which showed the X-ray powder analysis patterns of FIG. 1.

Figure 6:
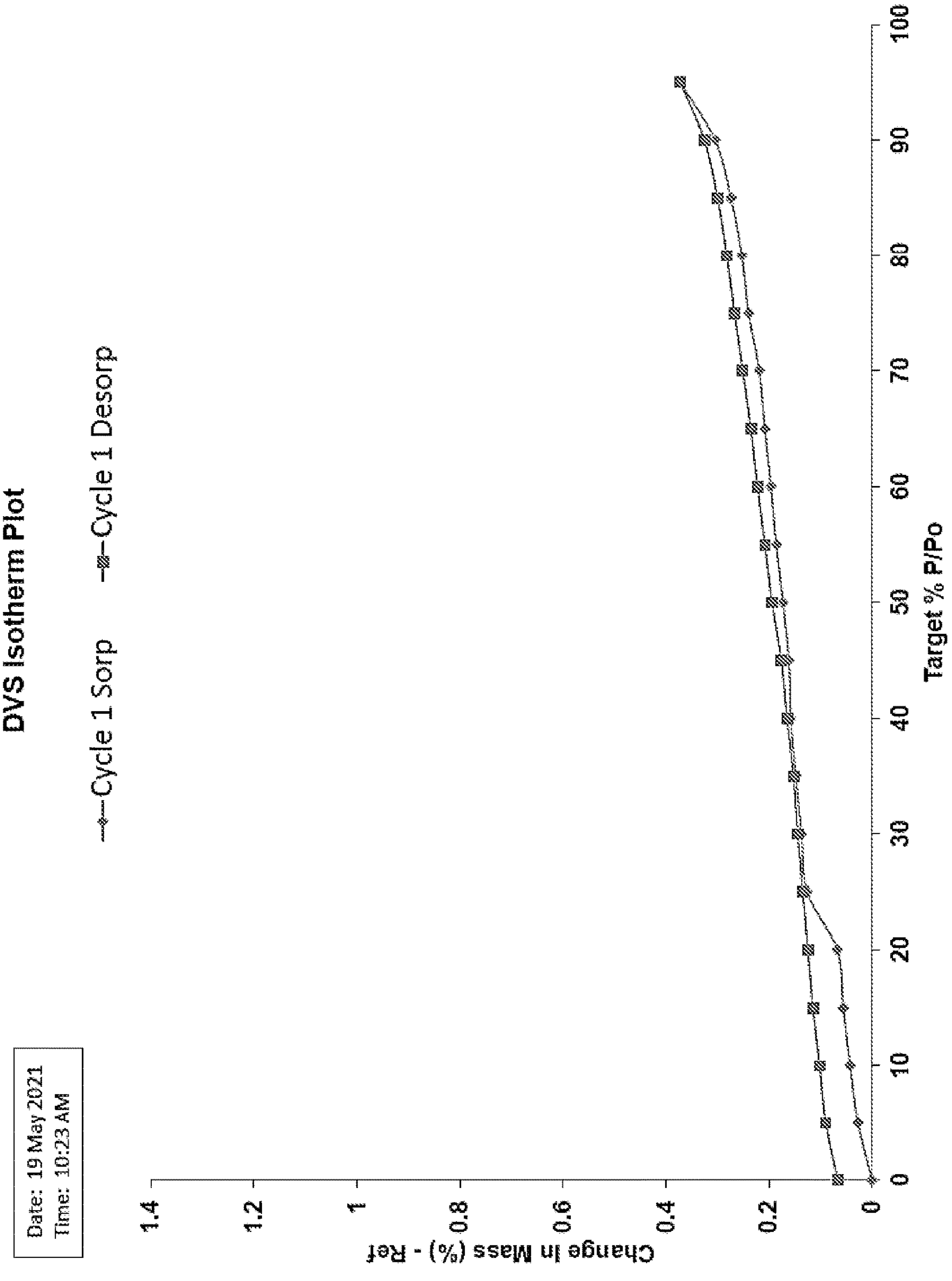
FIG. 6 shows DVS analysis results of fumaric acid cocrystal Form I (Form I) of the compound represented by Formula (VII), which showed the X-ray powder analysis patterns of FIG. 1. No substantial change in mass was observed when the humidity was changed, and the crystal was stable to moisture.

FIG. 6 shows DVS analysis results of fumaric acid cocrystal Form I (Form I) of the compound represented by Formula (VII), which showed the X-ray powder analysis patterns of FIG. 1.

The synthesis of Compound (I-005) represented by Formula (VII) can also be performed as follows.

Step 4'

Figure 8:
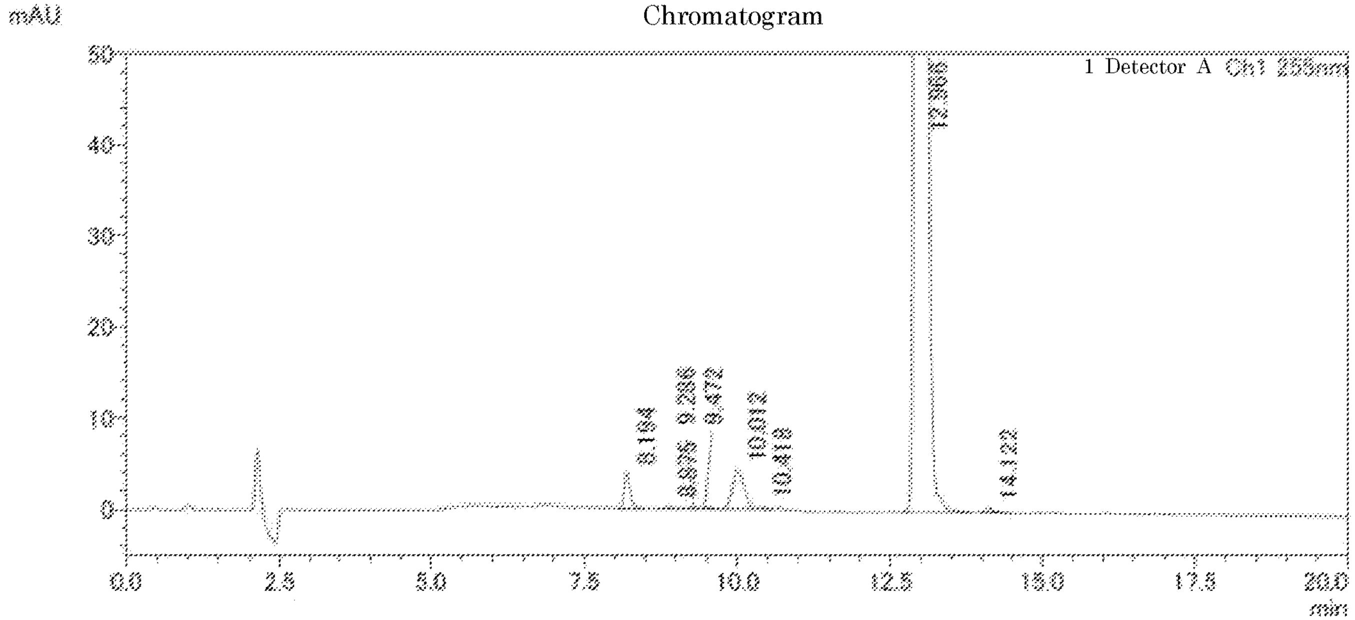
FIG. 8 shows HPLC measurement results of Compound I-005 obtained in Step 4'. The pa % of the compound represented by Formula (VII) (Compound I-005) was about 99 pa %.

To a mixture of Compound 20 (300 mg, 0.727 mmol), 6-chloro-2-methyl-2H-indazole-5-amine (172 mg, 0.946 mmol) in THF (6 mL) was added LHMDS (1M in THF; 1.46 mL, 1.46 mmol) dropwise at 0° C. The reaction solution was stirred at 0° C. for 2.5 hours and then stirred at room temperature for 40 minutes, and a saturated ammonium chloride aqueous solution was added thereto. The aqueous layer was extracted with EtOAc. The organic layer was washed with brine, dried over magnesium sulfate, and concentrated under reduced pressure. The residue was purified by silica gel column chromatography ($CHCl_3$/MeOH, gradient 0 to 20% MeOH). The obtained solid was solidified from acetone/H2O, to give Compound I-005 (95.3 mg, yield 25%, brown solid). The HPLC measurement results of the obtained Compound I-005 are shown in FIG. 8 (about 99 pa %).

Furthermore, the meaning of each abbreviation used herein is as follows.

BINAP: 2,2'-bis(diphenylphosphino)-1,1'-binaphthyl

CPME: cyclopentyl methyl ether

CbzCl: benzyl chloroformate

DME: dimethyl ether

MEK: methyl ethyl ketone

Example b (Method for Identifying Compounds)

NMR analysis of each Example and each Reference Example was performed by 400 MHz using DMSO-$d_6$ and $CDCl_3$. Furthermore, in NMR data shown in Examples and Reference Examples, not all measured peaks may be described.

"RT" or "retention time" means retention time in LC/MS: liquid chromatography/mass spectrometry or liquid chromatography (HPLC) and is measured under the following conditions.

Note that the description MS (m/z) indicates the value observed in the mass spectrometry.

(Measurement Conditions 1)

Column: ACQUITY UPLC (registered trademark) BEH C18 (1.7 μm i.d. 2.1×50 mm) (Waters)

Flow rate: 0.8 mL/min

UV detection wavelength: 254 nm

Mobile phases: [A] is a 0.1% formic acid-containing aqueous solution, and [B] is a 0.1% formic acid-containing acetonitrile solution Gradient: Linear gradient of 5% to 100% solvent [B] for 3.5 minutes was performed, and then 100% solvent [B] was maintained for 0.5 minutes.

(Measurement Conditions 2)

Column: ACQUITY UPLC (registered trademark) BEH C18 (1.7 μm i.d. 2.1×50 mm) (Waters)

Flow rate: 0.8 mL/min

UV detection wavelength: 254 nm

Mobile phases: [A] is a 10 mM ammonium carbonate-containing aqueous solution, and [B] is a 0.1% formic acid-containing acetonitrile solution Gradient: Linear gradient of 5% to 100% solvent [B] for 3.5 minutes was performed, and then 100% solvent [B] was maintained for 0.5 minutes.

(Measurement Conditions 4)

Column: Xselect CSH C18 (3.5 μm i.d. 4.6×150 mm) (Waters)

Column temperature: constant temperature at near 40° C.

UV detection wavelength: 254 nm

Mobile phases: [A] is a 0.1% formic acid-containing aqueous solution, and [B] is acetonitrile for liquid chromatography Gradient: Linear gradient of 5% to 95% solvent [B] for 17 minutes was performed, and then 95% solvent [B] was maintained for 3 minutes.

Flow rate: 1.0 mL/min

Injection amount: 5 μL (Measurement Conditions 5)

Column: Xselect CSH C18 (3.5 μm i.d. 4.6×150 mm) (Waters)

Column temperature: constant temperature at near 40° C.

UV detection wavelength: 254 nm

Mobile phases: [A] is a 0.1% formic acid-containing aqueous solution, and [B] is acetonitrile for liquid chromatography Gradient: Linear gradient of 5% to 95% solvent [B] for 17 minutes was performed, and then 95% solvent [B] was maintained for 3 minutes.

Flow rate: 1.0 mL/min

Injection amount: 10 µL (Measurement Conditions 7)

Column: Xselect CSH Fluoro-Phenyl (3.5 µm i.d. 4.6×150 mm) (Waters)

Column temperature: constant temperature at near 40° C.

UV detection wavelength: 255 nm

Mobile phases: [A] is a 0.1% formic acid-containing aqueous solution, and [B] is acetonitrile for liquid chromatography Gradient: 20% solvent [B] was maintained for 6 minutes, linear gradient of 20% to 42% solvent [B] for 21 minutes was performed, linear gradient of 42% to 50% solvent [B] for 4 minutes was performed, and finally, linear gradient of 50% to 95% solvent [B] for 3 minutes was performed.

Flow rate: 1.0 mL/min

Injection amount: 10 µL (Measurement Conditions 8)

Column: Xselect CSH Fluoro-Phenyl (3.5 µm i.d. 4.6×150 mm) (Waters)

Column temperature: constant temperature at near 40° C.

UV detection wavelength: 255 nm

Mobile phases: [A] is a 0.1% formic acid-containing aqueous solution, and [B] is acetonitrile for liquid chromatography Gradient: 20% solvent [B] was maintained for 2 minutes, linear gradient of 20% to 37% solvent [B] for 6 minutes was performed, linear gradient of 37% to 50% solvent [B] for 10 minutes was performed, and linear gradient of 50% to 95% solvent [B] for 2 minutes was performed.

Flow rate: 1.0 mL/min

Injection amount: 10 µL (Measurement Conditions 9)

Column: YMC Jsphere ODS-H80 (4 µm i.d. 4.6×250 mm)

Column temperature: constant temperature at near 40° C.

UV detection wavelength: 250 nm

Mobile phases: [A] is a 0.2% trifluoroacetic acid-containing aqueous solution, and [B] is methanol for liquid chromatography Gradient: Linear gradient of 10% to 70% solvent [B] for 6 minutes was performed, 70% solvent [B] was maintained for 3 minutes, linear gradient of 70% to 90% for 3 minutes was then performed, 90% solvent [B] was then maintained for 5 minutes, linear gradient of 90% to 95% for 1 minute was then performed, and 95% solvent [B] was then maintained for 5 minutes.

Flow rate: 1.0 mL/min

Injection amount: 5 µL (Measurement Conditions 10)

Column: Xselect CSH C18 (3.5 µm i.d. 4.6×150 mm)

Column temperature: constant temperature at near 40° C.

UV detection wavelength: 254 nm

Mobile phases: [A] is a 0.1% formic acid-containing aqueous solution, and [B] is acetonitrile for liquid chromatography Gradient: Linear gradient of 5% to 95% solvent [B] for 17 minutes was performed, and then 95% solvent [B] was maintained for 3 minutes.

Flow rate: 1.0 mL/min

Injection amount: 10 µL (Measurement Conditions 11)

Column: XBridge C18 (3.5 µm i.d. 4.6×150 mm)

Column temperature: constant temperature at near 40° C.

UV detection wavelength: 210 nm

Mobile phases: [A] is a 10 mM ammonia-containing aqueous solution, and [B] is methanol for liquid chromatography Gradient: 5% solvent [B] was maintained for 5 minutes, linear gradient of 5% to 38% solvent [B] for 10 minutes was performed, and linear gradient of 38% to 95% solvent [B] for 5 minutes was performed.

Flow rate: 0.8 mL/min

Injection amount: 10 µL (Measurement Conditions 12)

Column: C18 column

Column temperature: 40° C.

UV detection wavelength: 255 nm

Mobile phases: [A] is a 10 mM ammonia formate-containing aqueous solution, and [B] is methanol for liquid chromatography Regarding the gradient, the mixing ratio of mobile phase B was gradually increased from 9:1 to 1:9, and the measurement was performed for 28 minutes.

Flow rate: 0.3 mL/min

Injection amount: 4 µL (X-Ray Powder Diffraction Pattern Measurement)

X-ray powder diffraction pattern measurement of crystals obtained in each Example was performed according to a powder X-ray diffraction measurement method described in General Tests in Japanese Pharmacopoeia. Measurement conditions are as follows.

(Device)

MiniFlex600 manufactured by Rigaku Corporation (Operation Method)

Detector: high-speed one-dimensional detector (D/TecUltra2)

Type of light source: Cu bulb

Wavelength used: CuKα ray

Tube current: 15 mA

Tube voltage: 40 Kv

Sample plate: reflection-free sample plate (Measurement of Single Crystal Structural Analysis and Analysis Method)

The measurement conditions of the single crystal structural analysis and the analysis method are as follows.

(Device)

XtaLAB P200 MM007 manufactured by Rigaku Corporation (Measurement Conditions)

Measurement temperature: 25° C.

Wavelength used: CuKα ray (λ=1.5418 Å)

Software: CrysAlisPro 1.171.39.46e (Rigaku Oxford Diffraction, 2018)

(Data Processing)

Software: CrysAlisPro 1.171.39.46e (Rigaku Oxford Diffraction, 2018)

The data were corrected for the Lorentz, polarization and absorption effects.

(Crystal Structural Analysis)

The phase determination was performed by using the direct method program ShelXT (Sheldrick, G. M., 2015), and the structural refinement by full-matrix least-square method was then performed by using ShelXL (Sheldrick, G. M., 2015). All temperature factors of non-hydrogen atoms were refined with anisotropic parameters. Hydrogen atoms were placed by calculation using default parameters of ShelXL and regarded as riding atom. All hydrogen atoms were refined with isotropic parameters.

Figures were made using PLATON (Spek, 1991)/ORTEP (Johnson, 1976).

Measurement of Differential Scanning Calorimetry (DSC))

DSC measurement of crystals obtained in Examples was performed. About 2 mg of a sample was weighed into a SUS pan, and measurement was made by crimping the sample. Measurement conditions are as follows. Incidentally, in the measurement made by differential scanning calorimetry (DSC), an error can occur in the range of ±2° C.

Device: DSC 3+

Measurement temperature range: 30° C. to 300° C.

Rate of temperature increase: 10° C./min

Atmosphere: N2 40 mL/min (Measurement of TG/DTA Data)

About 3 mg of the crystals obtained in Examples were weighed and packed into an aluminum pan, and measurement was performed in an open system.

Measurement conditions are as follows.

Device: Hitachi High-Tech Science Corporation TG/DTA 7200

Measurement temperature range: 30 to 350° C.

Rate of temperature increase: 10° C./min (Moisture Sorption/Desorption Isotherm Measurement)

About 15 to 25 mg of a sample was weighed into a sample pan, and measurement was made. Measurement conditions are as follows.

Device: DVS Adventure manufactured by Surface Measurement Systems Ltd.

Measurement points: 0% to 95% RH every 5%, and 95% RH to 0% every 5%

Temperature: 25° C.

Regarding the comparison of the X-ray powder analysis patterns before and after the DVS measurement, measurement was performed by the following method.

(Device)

SmartLab manufactured by Rigaku Corporation (Operation Method)

Measuring method: reflection method

Wavelength used: CuKα ray

Tube current: 200 mA

Tube voltage: 45 kV

Sampling plate: aluminum

X-ray incident angle: 2.5°

Sampling width: 0.02°

Detector: HyPix-3000 (two-dimensional detection mode)

(Measurement of Particle Size Distribution)

Measurement conditions are as follows.

Manufacturer: Sympatec

Device: laser diffraction HELOS & RODOS particle size distribution measuring device Range: R4

Dispersion pressure: 3 bar

Trigger conditions: stop: 2 s measured concentration≤1% or 10 s real time

Example 1b

Synthesis of Fumaric Acid Cocrystal Form I of Compound Represented by Formula (VII)

[Chemical Formula 35]

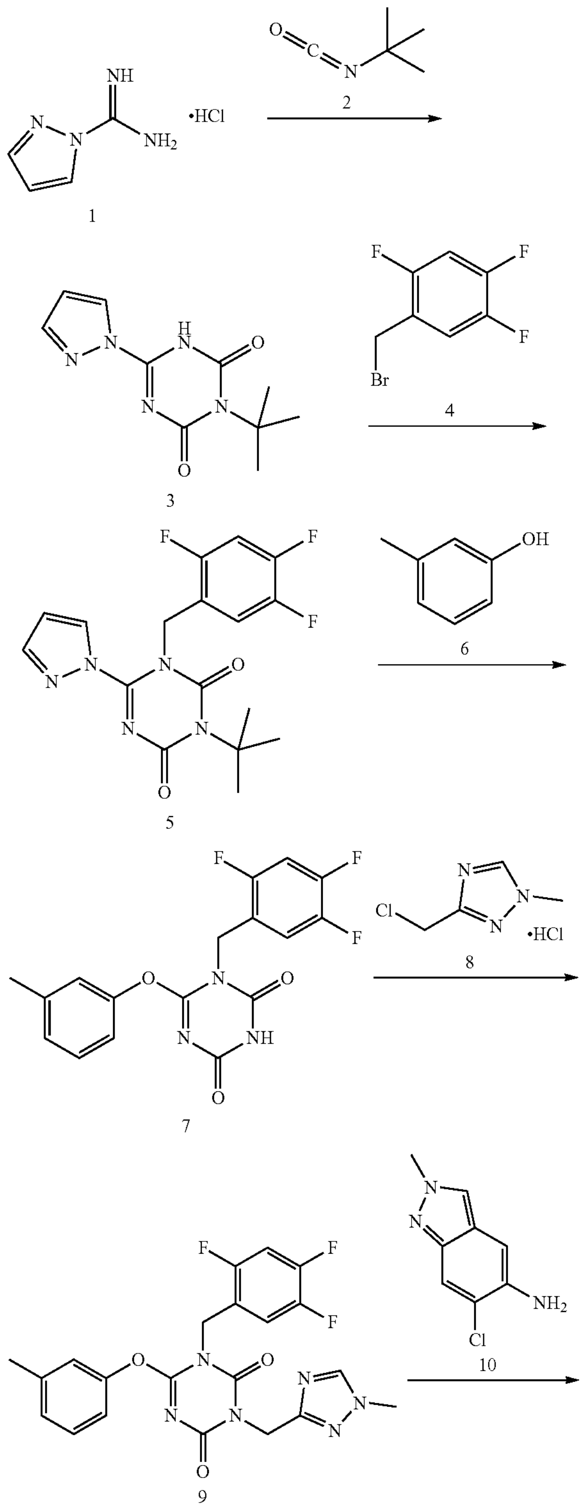

-continued

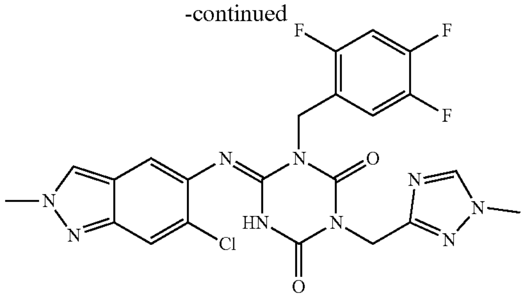

(VII)

Step 1: Synthesis of Compound 3

Compound 1 (35.0 kg, 238.8 mol, hydrochloride), N,N-dimethylacetamide (273 L), 1,8-diazabicyclo[5,4,0]-7-undecene (87.2 kg, 573.1 mol), and Compound 2 (26.0 kg, 262.7 mol) were mixed and stirred at 25° C. for 10 minutes. N,N'-carbonyldiimidazole (50.3 kg, 310.4 mol) and N,N-dimethylacetamide (7 L) were mixed with the reaction solution and stirred at 50° C. for 90 minutes. Methanol (18.4 kg, 573.1 mol) was added to the reaction solution and cooled to 25° C., and the pH was adjusted with 10% sulfuric acid to 2.5. The slurry was cooled to 5° C., and the solid was collected by filtration, washed with 20% methanol water, and dried, to give Compound 3 (38.12 kg, 162.0 mol, yield: 67.9%).

HPLC (UV=254 nm): RT=8.9 min, HPLC measurement conditions 4

Step 2: Synthesis of Compound 5

Compound 3 (34.5 kg, 146.7 mol), acetonitrile (345 L), diisopropylethylamine (26.5 kg, 205.4 mol), and Compound 4 (39.6 kg, 176.0 mol) were mixed and stirred at 60° C. for 300 minutes. The reaction solution was cooled to 25° C. and water (172.5 L) was added thereto. The slurry was cooled to 0° C., and the solid was collected by filtration, washed with 66% acetonitrile water, and dried, to give Compound 5 (46.10 kg, 121.5 mol, yield: 82.9%).

HPLC (UV=254 nm): RT=14.7 min, HPLC measurement conditions 4

Step 3: Synthesis of Compound 7

Compound 5 (29.0 kg, 76.4 mol), trifluoroacetic acid (72.5 L), and Compound 6 (16.5 kg, 152.9 mol) were mixed and stirred at 35° C. for 180 minutes. The reaction solution was cooled, ethyl acetate (348 L) was added thereto, and the resulting product was washed with a 38% tripotassium phosphate aqueous solution, 2.3% saline, and water. Ethyl acetate was concentrated to 203 L and heptane (261 L) was added thereto. The slurry was cooled to 0° C., and the solid was collected by filtration, washed with a mixed solvent of ethyl acetate and heptane, and dried, to give Compound 7 (23.60 kg, 65.0 mol, yield: 85.0%).

HPLC (UV=254 nm): RT=12.5 min, HPLC measurement conditions 5

Step 4: Synthesis of Compound 9

Compound 7 (23.3 kg, 64.1 mol), Compound 8 (14.0 kg, 83.4 mol, hydrochloride), potassium iodide (6.4 kg, 38.5 mol), cesium carbonate (31.3 kg, 96.2 mol), and N,N-dimethylacetamide (139.8 L) were mixed and stirred at 40° C. for 360 minutes. The reaction solution was cooled to 25° C. and acetic acid (34.6 kg, 577.2 mol) was added thereto. The insoluble matters were separated by filtration, and acetonitrile (93.2 L) and water (326.2 L) were added to the filtrate. The slurry was cooled to 0° C., and the solid was collected by filtration, washed with 20% acetonitrile water, and dried to give Compound 9 (20.35 kg, 44.4 mol, yield: 69.2%).

HPLC (UV=255 nm): RT=25.1 min, HPLC measurement conditions 7

The same operation was performed twice for Steps 1 to 4.

Step 5-1: Synthesis of Fumaric Acid Cocrystal Form I of Compound Represented by Formula (VII)

Figure 12:
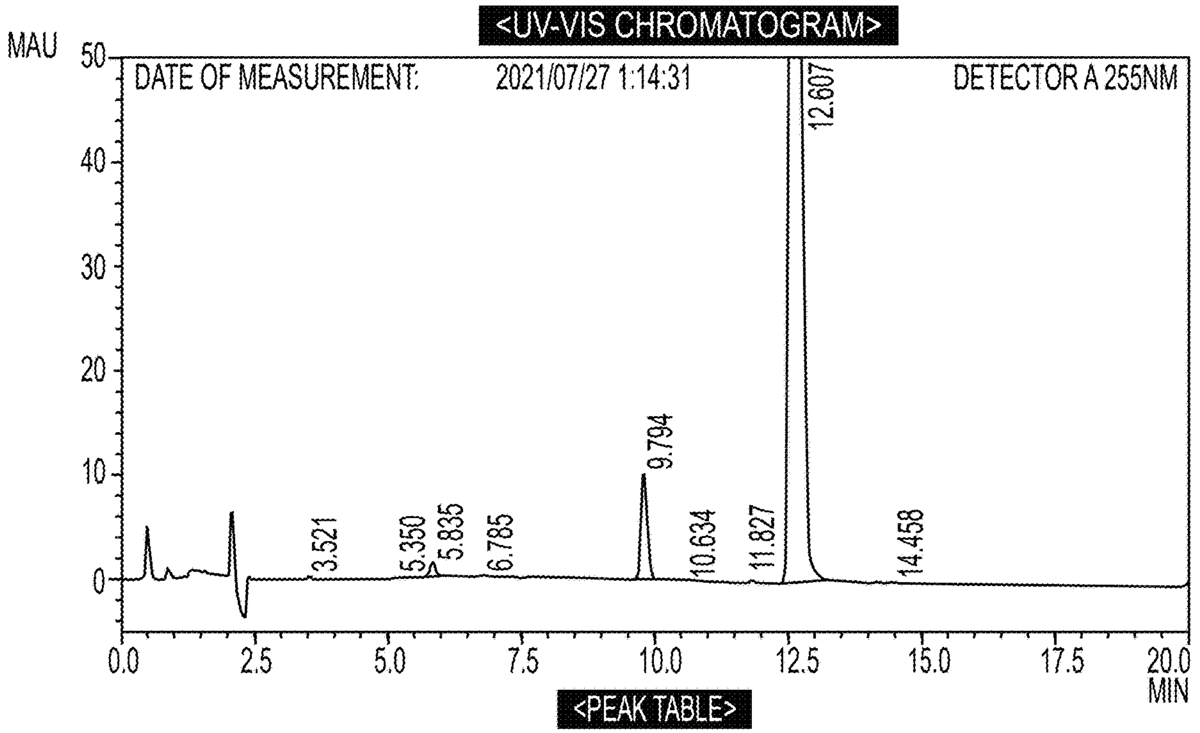
FIG. 12 shows results of HPLC of an undried crystal of the compound represented by Formula (VII) obtained in Step 5-1 of Example 1b. The pa % of the compound represented by Formula (VII) was about 99 pa %.
Figure 13:
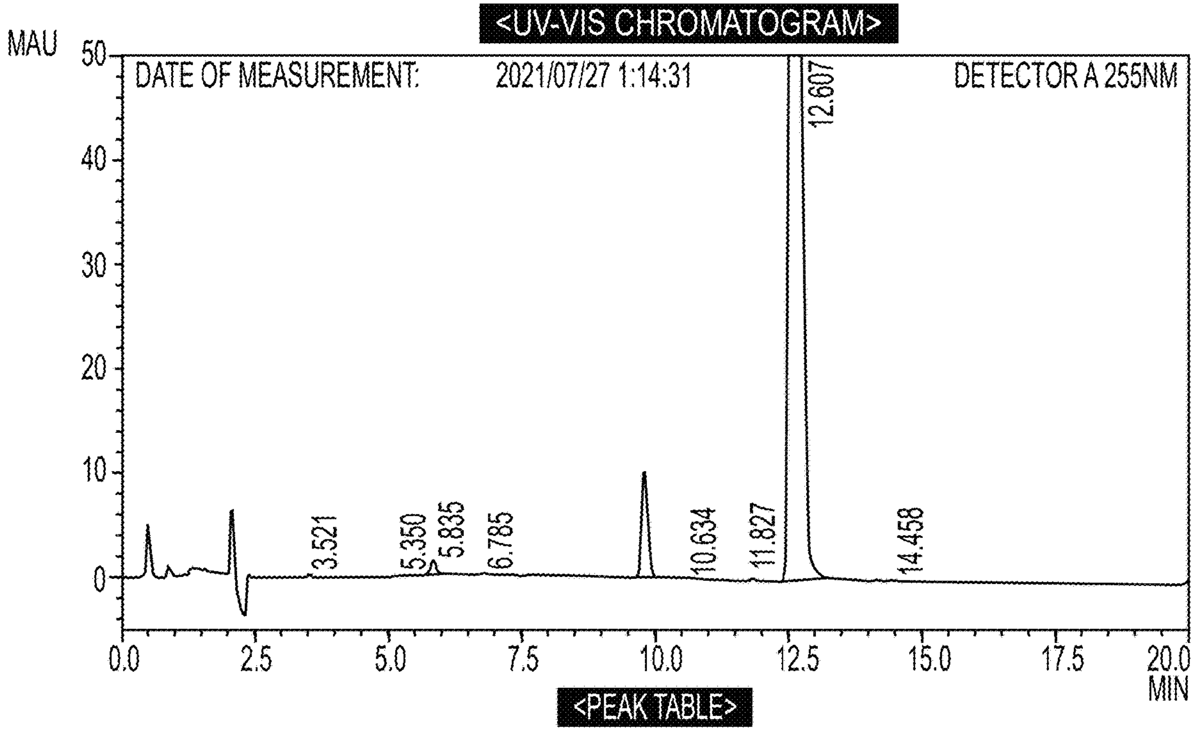
FIG. 13 shows analysis results excluding a peak derived from toluene (RT=about 9.8 min) in FIG. 12. The pa % of the compound represented by Formula (VII) was about 99.7 pa %, and the pa % of each impurity was less than about 0.1 pa %.
Figure 14:
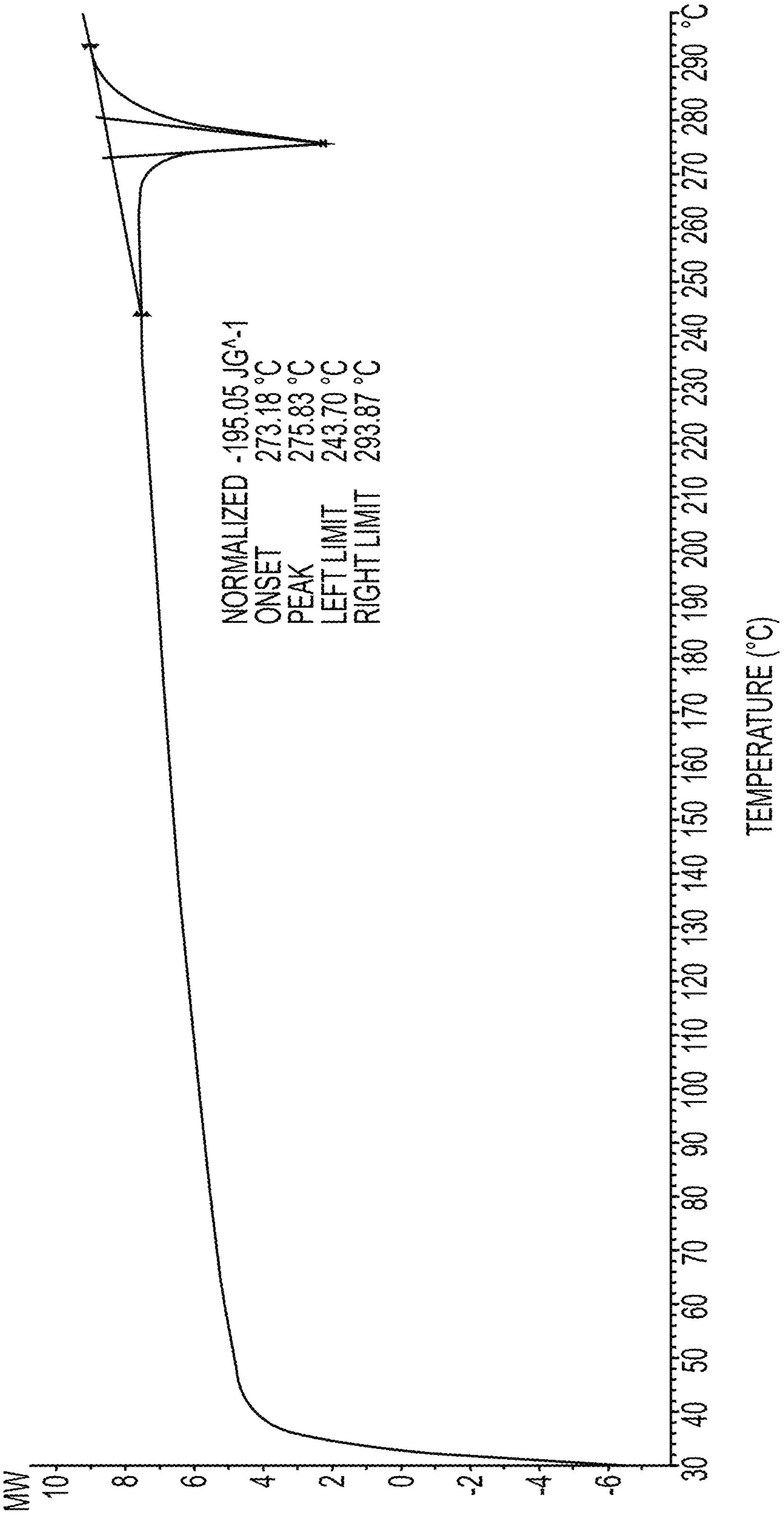
FIG. 14 shows DSC analysis results of fumaric acid cocrystal Form I (Form I) of the compound represented by Formula (VII) obtained in Step 5-2 of Example 1b.
Figure 15:
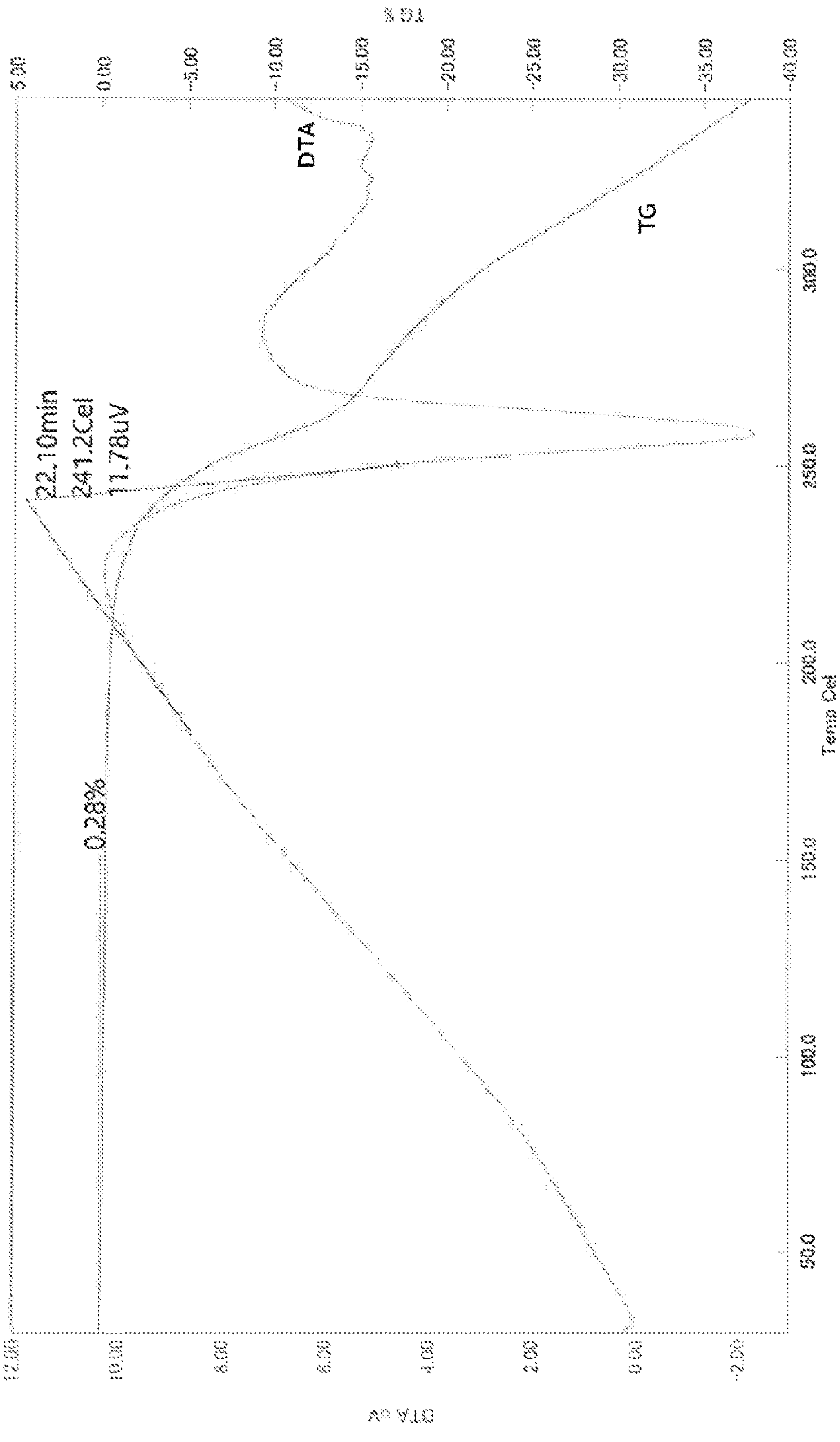
FIG. 15 shows TG/DTA analysis results of fumaric acid cocrystal Form I (Form I) of the compound represented by Formula (VII) obtained in Step 5-2 of Example 1b. The mass loss up to 150° C. was 0.28%.
Figure 16:
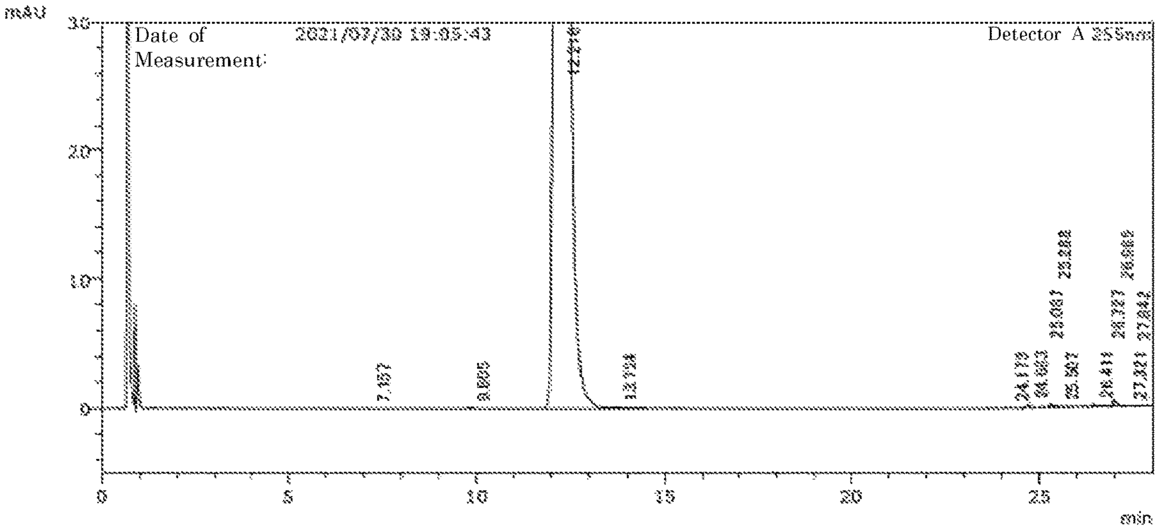
FIG. 16 shows HPLC results of fumaric acid cocrystal Form I (Form I) of the compound represented by Formula (VII) obtained in Step 5-2 of Example 1b.
Figure 17:
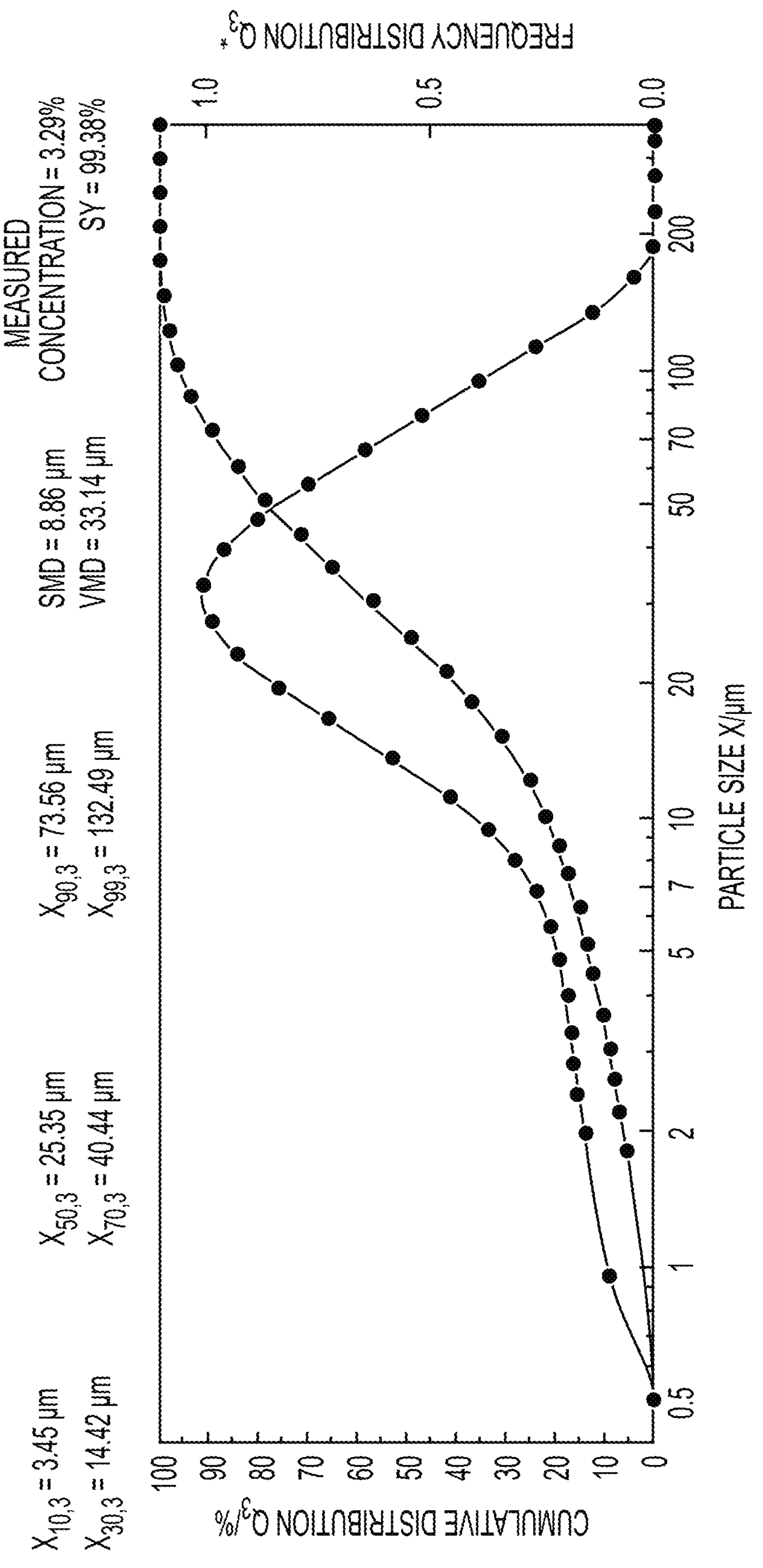
FIG. 17 shows a particle size distribution of fumaric acid cocrystal Form I (Form I) of the compound represented by Formula (VII) obtained in Step 5-2 of Example 1b. D50 was 25.35 μm, and D90 was 73.56 μm.
Figure 18:
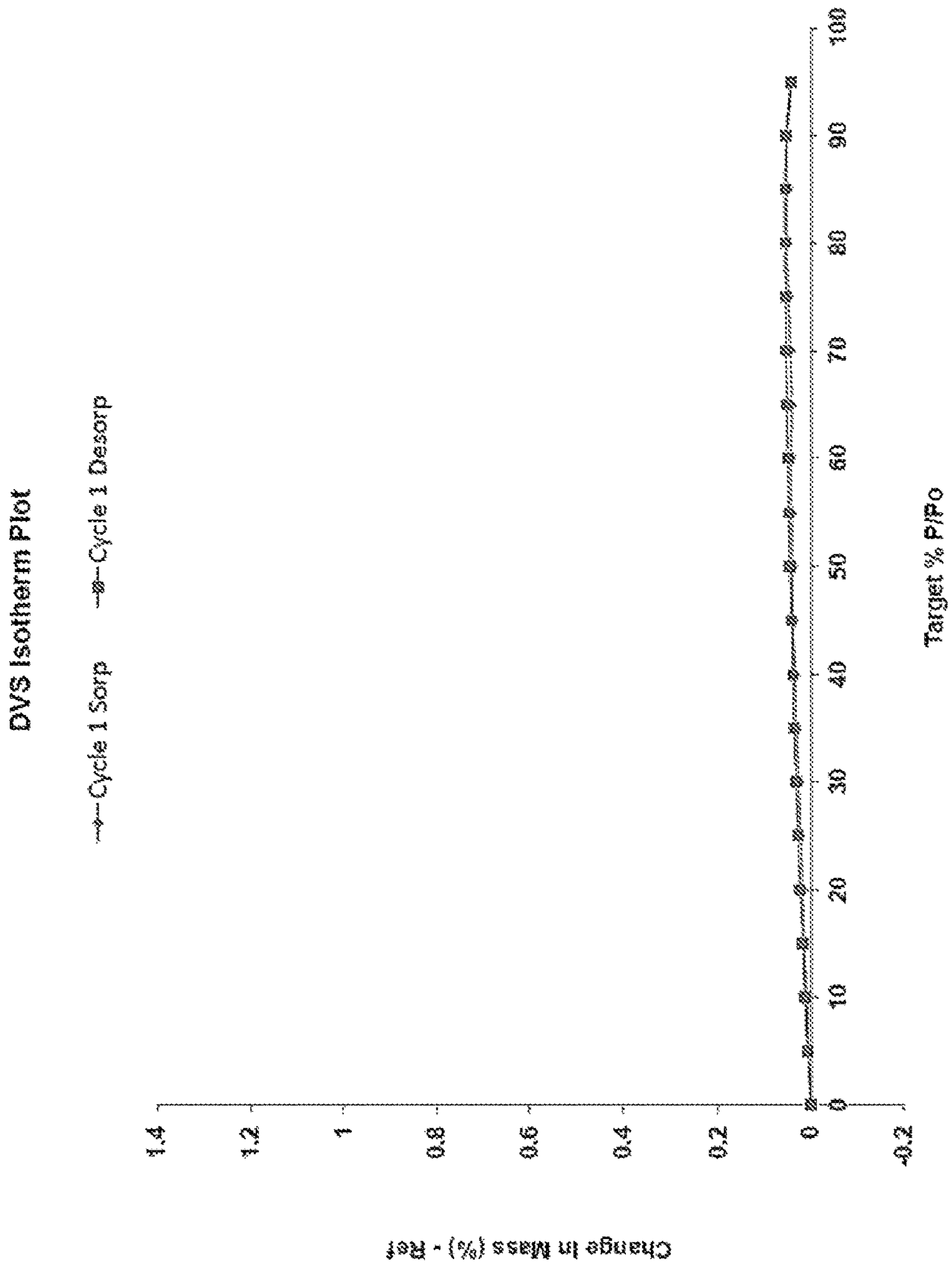
FIG. 18 shows DVS analysis results of fumaric acid cocrystal Form I (Form I) of the compound represented by Formula (VII) obtained in Step 5-2 of Example 1b. No substantial change in mass was observed when the humidity was changed, and the crystal was stable to moisture.

Compound 9 (39.0 kg, 80.7 mol) obtained in Steps 1 to 4, Compound 10 (16.2 kg, 84.8 mol), acetic acid (30.7 kg, 484.3 mol), and toluene (234 L) were mixed and stirred at 100° C. for 360 minutes. Toluene (390 L) was added thereto, and the slurry thus obtained was cooled to 25° C. The solid was collected by filtration and washed with acetone to give an undried crystal of the compound represented by Formula (VII) (the results of HPLC measurement of the obtained undried crystal under HPLC measurement conditions 8 are shown in FIGS. 12 and 13. The peak at RT=9.8 min is toluene).

Figure 19:
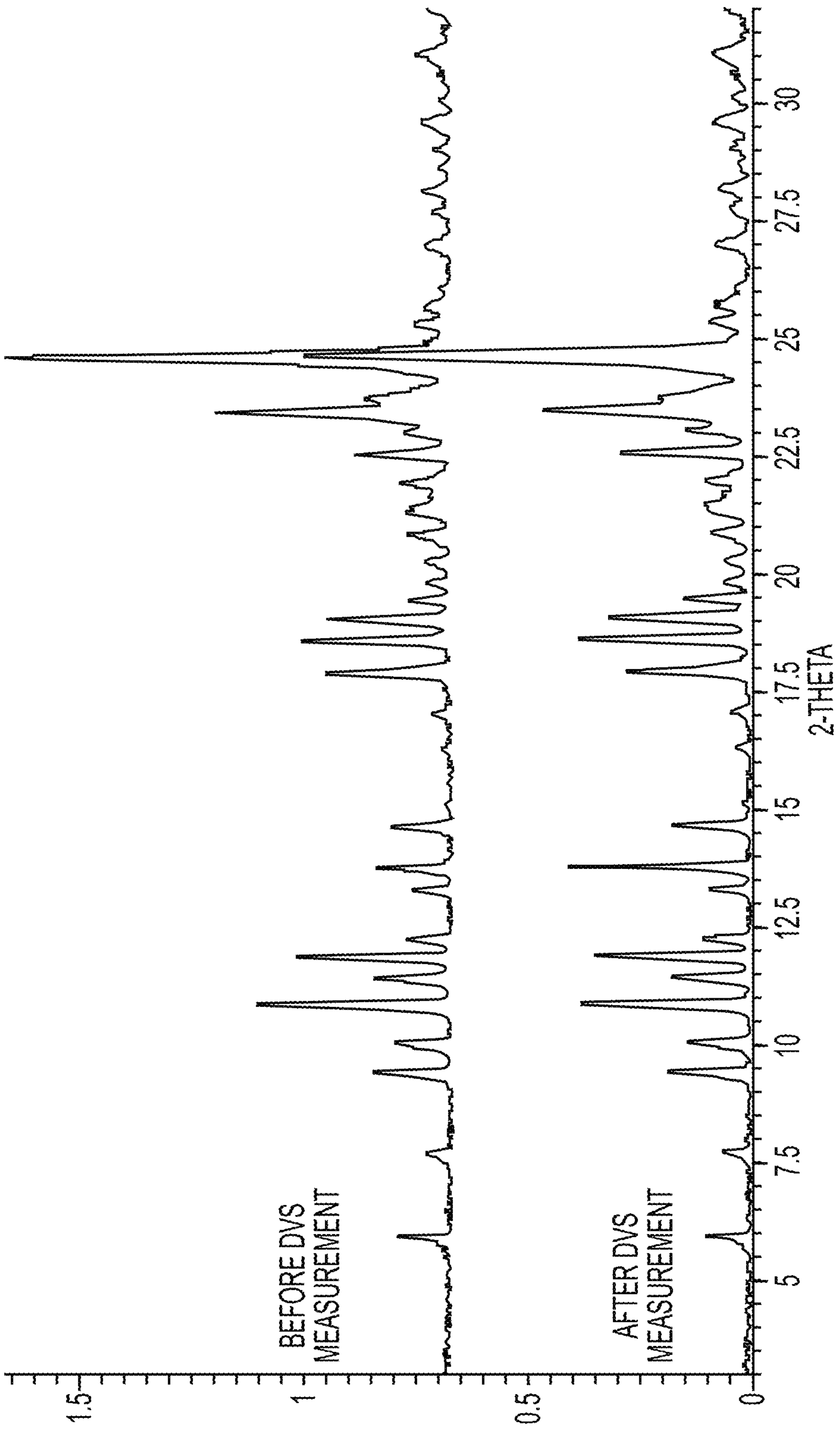
FIG. 19 shows a comparison of X-ray powder analysis patterns before and after the DVS measurement of FIG. 18. The crystalline form did not change before and after the DVS measurement, and was stable.

Step 5-2: To a half of the obtained undried crystal of the compound represented by Formula (VII) were added acetone (613.5 L) and water (109.2 L), and the mixture was dissolved at 50° C. The obtained solution was subjected to an activated carbon treatment, acetone (150.2 L) and water (5.9 L) were added to the treatment liquid, and the resulting solution was concentrated to 702 L. The temperature of the concentrated liquid was adjusted to 50° C., fumaric acid (4.6 kg, 72.6 mol), acetone (150.2 L), and water (5.9 L) were added thereto, and the resulting solution was concentrated to 464 L. Acetone (78 L) was added to the concentrated liquid, the resulting solution was concentrated to 265 L, and acetone (19.5 L) was added thereto. The temperature of the slurry was adjusted to 55° C. and the slurry was stirred for 120 minutes or longer. The slurry was cooled to 0° C., and the solid was collected by filtration, washed with acetone, and then dried (the results of DSC, TG/DTA, HPLC, particle size distribution, and DVS measurement of the obtained dried crystal are shown in FIGS. 14 to 18. HPLC was measured under measurement conditions 12. FIG. 19 shows a comparison of X-ray powder analysis patterns before and after the DVS measurement.).

The same operation was repeated also for the remaining half, to give fumaric acid cocrystal Form I (41.68 kg, 64.3 mol, yield: 75.6%) of the compound represented by Formula (VII).

HPLC (UV=255 nm): RT=12.8 min, HPLC measurement conditions 8

Example 2b

Synthesis of Toluene Solvate of Compound Represented by Formula (VII)

Step 1

Compound 9 (150 mg, 0.327 mmol) and Compound 10 (65.4 mg, 0.360 mmol) were mixed with toluene (1.5 mL) and acetic acid (0.187 ml, 3.27 mmol) and stirred at 100° C. for 9 hours. The resulting mixture was cooled to room temperature and filtered with addition of heptane (1.5 mL, 10 V), and the obtained crystals were washed with heptane (0.7 mL) three times. The drying under reduced pressure was performed, thereby obtaining crystals (168 mg, yield 87%) of the compound represented by Formula (VII). Toluene corresponding to 0.5 to 0.6 molecules was contained as the solvate in the obtained crystals, and toluene was not removed by drying under reduced pressure of a general operation range. The acquisition of the toluene solvate of the compound represented by Formula (VII) that is good in quality was confirmed.

$^1$H-NMR (400 MHz, $CDCl_3$) δ ppm: 7.93 (s, 1H), 7.70 (d, J=2.57 Hz, 2H), 7.62 (brs, 1H), 7.35-7, 45 (m, 1H), 7.07 (m, 1H), 6.92-6.97 (td, J=9.63, 6.42, 1H), 5.34 (s, 2H), 5.14 (s, 2H), 4.20 (s, 3H), 3.87 (s, 2H).

Peaks corresponding to 0.5 to 0.6 molecules of toluene were confirmed at 7.14 to 7.27 ppm and 2.35 ppm.

Reference Example 1 Synthesis of Compound S-4

[Chemical Formula 36]

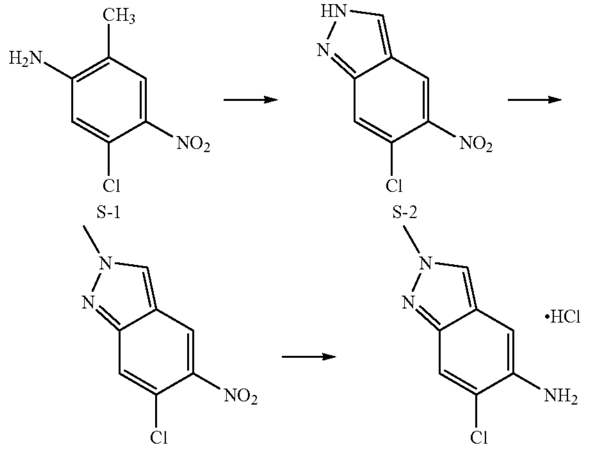

S-1 S-2 S-3 S-4

Step 1: Synthesis of Compound S-2

Compound S-1 (5.50 kg, 29.5 mol), acetonitrile (21.7 kg), and glacial acetic acid (115.00 kg) were mixed and cooled to 5° C. To the resulting mixture, a 17% sodium nitrite aqueous solution (13.03 kg) was added and stirred for 1 hour, heated to 25° C., and then stirred for 1.5 hours. The insoluble matters were separated by filtration and the insoluble matters were washed with acetonitrile (21.7 kg) and tetrahydrofuran (49.0 kg). Water (460 L) was added to the collected filtrate. The slurry was cooled to 0° C., and the solid was collected by filtration, washed with water, and dried, thereby obtaining Compound S-2 (3.75 kg, 19.0 mol, yield: 64.4%).

LC/MS (ESI): m/z=196 (M−H), RT=11.8 min, LC/MS measurement conditions 4

Step 2: Synthesis of Compound S-3

Compound S-2 (3.25 kg, 16.4 mol) and ethyl acetate (58.7 kg) were mixed, and trimethyloxonium tetrafluoroborate (2.09 kg, 14.1 mol) was added thereto and stirred at 25° C. for 7 hours. A mixed liquid of ethyl acetate (29.5 kg) and methanol (10.3 kg) was added to this reaction solution. This mixed liquid was added to a 5% sodium carbonate aqueous solution (66.3 kg), followed by separation into the organic layer and the aqueous layer. The organic layer was washed twice with a 5% sodium chloride aqueous solution (65.8 kg), subjected to an activated carbon treatment, and concentrated to 42 kg. The operation of adding tetrahydrofuran (87.0 kg) and concentrating to 23 kg was performed twice, tetrahydrofuran (87.0 kg) was further added, followed by concentration to 18.9 kg and heating to 33° C. Heptane (47.0 kg) was added to this mixed liquid. The slurry was cooled to 0° C., and the solid was collected by filtration, washed with a mixed liquid of tetrahydrofuran and heptane, and dried, thereby obtaining Compound S-3 (1.68 kg, 7.9 mol, yield: 48.2%).

LC/MS (ESI): m/z=212 (M+H), 253 ($M+CH_3CN+H$) RT=12.4 min, LC/MS measurement conditions 4

Step 3: Synthesis of Compound S-4

Compound S-3 (1040 g, 4.9 mol), 10% palladium carbon (PE type, hydrated) (523 g, 0.25 mol), and ethyl acetate (8.99 kg) were mixed, and hydrazine monohydrate (504 g, 10.1 mol) was added thereto and stirred at 35° C. for 3 hours. 10% palladium carbon was separated by filtration and the 10% palladium carbon was washed with water (1560 g) and ethyl acetate (9.00 kg). To the collected filtrate, 2 mol/L hydrochloric acid (750 g) was added, followed by separation into the organic layer and the aqueous layer. The obtained aqueous layer was extracted with ethyl acetate (4.69 kg). The organic layer was subjected to an activated carbon treatment and concentrated to 11.09 kg. To this concentrated liquid, a 4 mol/L hydrogen chloride-ethyl acetate solution (1124 g) was added. The solid was collected by filtration, washed with ethyl acetate, and dried, thereby obtaining Compound S-4 (0.84 kg, 3.9 mol, yield: 78.5%).

LC/MS (ESI): m/z=182 (M+H), 223 ($M+CH_3CN+H$) RT=6.6 min, LC/MS measurement conditions 4

Chlorine concentration (ion chromatography): 16.74%

Reference Example 2 Synthesis of Compound A-3

[Chemical Formula 37]

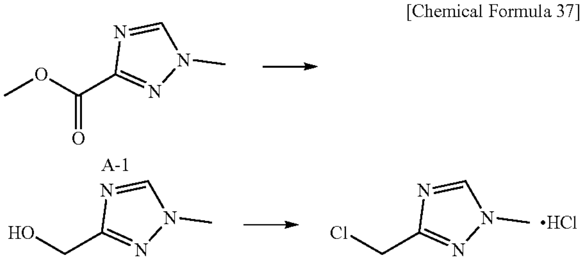

A-1 A-2 8

Step 1: Synthesis of Dichloromethane Solution of Compound A-2

Compound A-1 (9.2 kg, 65.1 mol) and tetrahydrofuran (64 L) were mixed and cooled to 0° C. to prepare slurry. A Red-AL/tetrahydrofuran solution obtained by mixing sodium bis(2-methoxy)aluminum hydride (Red-AL)/toluene solution (65 wt %) (26.4 kg, 84.9 mol) and tetrahydrofuran (28 L) was added dropwise thereto over 60 minutes while the internal temperature was maintained at 8° C. or lower. Thereafter, the resulting solution was stirred at 0° C. to 5° C. for 30 minutes. Acetone (4.9 kg, 84.3 mol) was added dropwise to the reaction solution over 30 minutes and heated to 25° C. A slurry obtained by mixing potassium sodium tartrate tetrahydrate (46 kg, 163 mol) and tetrahydrofuran (138 L) was prepared in another reactor, and the reaction solution obtained by quenching the Red-AL reduction mentioned above with acetone was added dropwise to the slurry over 30 minutes (at this time, the internal temperature was at near 40° C.). The resulting solution was continuously stirred for 2 hour at 40° C. and cooled to 25° C. After water (2.5 kg) was added and stirred, Buchner filtration was performed, and the obtained filtrate was concentrated under reduced pressure to 35 kg (28 L). The filtrate (28 L) was divided equally into three, and toluene (2.6 kg) was added to the first filtrate, subjected repeatedly to the operation of concentration under reduced pressure 8 times, and then finally concentrated and dried. Dichloromethane (13.5 kg) was added to the concentrated and dried product to obtain a dichloromethane solution of Product A-2. The same operation was performed for the second and third filtrates, and an A-2/dichloromethane solution containing A-2 (5.53 kg) and dichloromethane (42.7 kg) was prepared (yield: 74.8%).

$^1$H-NMR (400 MHz, $CDCl_3$, 30° C.) δ ppm: 8.00 (s, 1H), 4.74 (s, 2H), 3.90 (s, 3H).

Step 2: Synthesis of Compound 8

Dichloromethane (44 L) was added to the A-2/dichloromethane solution produced Step 1 (49.8 kg of dichloromethane solution containing 5.53 kg of A-2 (48.8 mol)) and the temperature thereof was adjusted to 25° C. A solution obtained by mixing thionyl chloride (7.8 kg, 65.5 mol) and dichloromethane (27 L) was added dropwise over 30 minutes, subjected to line washing using dichloromethane (8.2 L), and allowed to flow in, and then the resulting solution was stirred at room temperature for 7 hours. Separately, a 20% sodium acetate aqueous solution (179 kg) was prepared from sodium acetate (36.2 kg, 436 mol) and tap water (143 L). To the reaction solution mentioned above, 20% sodium acetate (119 kg) was added dropwise. The pH at the time point of the completion of dropwise addition was around 4.6. The organic layer obtained in this operation was washed with a 10% sodium chloride aqueous solution prepared from sodium chloride (5.5 kg) and tap water (49 L), and the aqueous layer was also extracted with dichloromethane (55 L). The combined organic layer (dichloromethane solution) was concentrated to 33 L, added with ethyl acetate (27.5 L), and concentrated. After the resulting solution was concentrated to 33 L, ethyl acetate (47.5 L) was newly added, the resulting solution was concentrated under normal pressure at a jacket temperature of 60° C., and the produced inorganic salt was filtered. A hydrochloric acid-ethyl acetate solution (4 mol/L, 12.6 kg) was added to the filtrate to obtain hydrochloride, and the resulting solution was stirred at 25° C. for 30 minutes and then cooled at near 5° C. After stirring for 30 minutes and crystal aging, the obtained crystallized slurry was filtered, washed with cooled ethyl acetate (55 L), and dried under reduced pressure, thereby obtaining Compound 8 (5.25 kg) (pale yellow powder, yield: 64.8%).

$^1$H-NMR (400 MHz, DMSO-$d_6$, 30° C.) δ ppm: 8.54 (s, 1H), 4.70 (s, 2H), 3.86 (s, 3H).

Reference Example 3 Synthesis of Compound 10

[Chemical Formula 38]

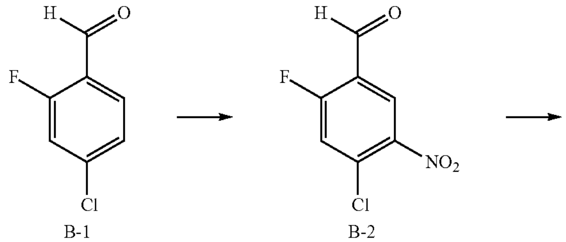

B-1 B-2

-continued

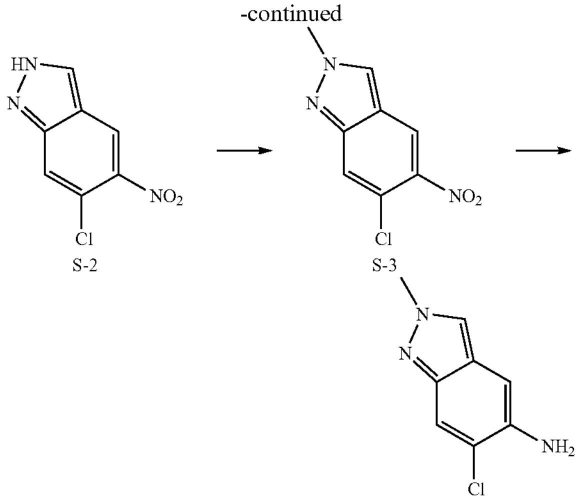

S-2 S-3 10

Step 1: Synthesis of Compound B-2

Compound B-1 (79.1 kg, 499 mol) was added dividedly to 98% sulfuric acid (395.7 L) cooled to 0° C. to 5° C. in a nitrogen atmosphere (the internal temperature was maintained at 0° C. to 5° C.). Potassium nitrate (55.5 kg) was added dividedly in 15 times (with an interval of 20 minutes or longer) while the internal temperature was maintained at 0° C. to 12° C. The resulting solution was stirred at an internal temperature of 0° C. to 5° C. for 5 hours. The aforementioned reaction solution was allowed to slowly flow in water (791 L) cooled to 0° C. to 5° C. while the internal temperature was maintained at 0° C. to 5° C., washed with 98% sulfuric acid (39.6 L), and then stirred at an internal temperature of 0° C. for 5 hours. The slurry was filtered by a centrifuge and washed with water (791 L). The obtained coarse solid was suspended in water (791 L) and stirred at 20° C. to 30° C. for 30 minutes, and the solid was filtered, washed with water (791 L) three times, and dried under reduced pressure, thereby obtaining Compound B-2 (99.61 kg).

$^1$H-NMR (400 MHz, $CDCl_3$) δ ppm: 10.31 (s, 1H), 8.46 (d, J=6.60 Hz, 1H), 7.47 (d, J=9.17 Hz, 1H).

HPLC (UV=250 nm): RT=10.9 min, HPLC measurement conditions 9

Step 2: Synthesis of Compound S-2

Ethanol (697 L), water (697 L), and hydrazine monohydrate (73.5 kg, 1468 mol) were mixed and heated to 45° C. Thereto, a solution obtained by mixing Compound B-2 (99.6 kg, 489 mol) and ethanol (299 L) was added dropwise over 60 minutes and further stirred for 8 hours and at 45° C. to 50° C. for 9 hours. While the internal temperature was maintained at 40° C. to 50° C., an aqueous solution prepared from potassium hydrogen carbonate (53.9 kg, 538 mol) and water (1295 L) was added dropwise over 30 minutes. The resulting solution was cooled to 0° C. to 5° C., stirred for 1 hour, and filtered. Water (1335 L) and ethanol (657 L) were mixed, and the aforementioned solid was washed with an ethanol aqueous solution cooled to 0° C. to 5° C. The drying under reduced pressure was performed, thereby obtaining Compound S-2 (83.25 kg) (yield: 86.9%).

$^1$H-NMR (400 MHz, DMSO-$d_6$) δ ppm: 13.56-13.98 (m, 1H), 8.67 (s, 1H), 8.37 (d, J=0.98 Hz, 1H), 7.92 (d, J=0.61, 1H).

HPLC (UV=250 nm): RT=10.4 min, HPLC measurement conditions 9

Step 3: Synthesis of Compound S-3

Compound S-2 (84 kg, 430 mol) and ethyl acetate (1596 L) were mixed and stirred at 20° C. to 30° C. Trimethyloxonium tetrafluoroborate (77.6 kg, 525 mol) was added dividedly in plural times, ethyl acetate (84 L) was added, and the resulting solution was stirred at 25° C. for 6 hours. A solution obtained by mixing methanol (252 L) and ethyl acetate (420 L) was added dropwise to the reaction solution over 2 hours and quenched with excess trimethyloxonium tetrafluoroborate. The reaction solution obtained after quenching was added dropwise to a sodium carbonate aqueous solution obtained by mixing sodium carbonate (84 kg) and water (1596 L) over 1 hour and ethyl acetate (420 L) and methanol (84 L) were added thereto. The organic layer resulting from the liquid separation operation was washed with saturated saline (1680 kg) twice, and the organic layer thus obtained was filtered with activated carbon. Thereafter, the organic layer was concentrated under reduced pressure, tetrahydrofuran (2520 L) was allowed to flow thereinto, and concentration under reduced pressure was further performed. After the operation of additional inflowing of tetrahydrofuran and concentration under reduced pressure was performed again, heptane (2139 L) was added dropwise, and the resulting product was cooled to −5° C. to 5° C. and then stirred at near 0° C. for 1 hour, followed by crystal aging. The crystallized slurry was filtered and washed with a solution obtained by mixing cooled tetrahydrofuran (224 L) and heptane (912 L). The drying under reduced pressure was performed, thereby obtaining Compound S-3 (65.73 kg) (yield: 74.1%).

$^1$H-NMR (400 MHz, $CDCl_3$) δ ppm: 8.31 (s, 1H), 8.13 (s, 1H), 7.81 (s, 1H), 4.27 (s, 3H).

HPLC (UV=254 nm): RT=10.3 min, HPLC measurement conditions 10

Step 4: Synthesis of Compound 10

Compound S-3 (65.7 kg, 310 mol) and ethyl acetate (657 L) were mixed, and stirred at room temperature, and cooled at near 10° C., and nitrogen substitution was performed. 5% platinum-carbon (57.7 kg, containing 53% moisture) was added. After hydrogen substitution, the resulting solution was stirred for 4 hours while the internal temperature was adjusted to near 25° C. After confirming the disappearance of raw materials, nitrogen substitution and filtration operation were performed to remove the platinum-carbon catalyst. After the liquid separation operation, the organic layer was concentrated, and heptane was added dropwise to the ethyl acetate solution, thereby forming a crystallized slurry. After filtration and washing with heptane/ethyl acetate, the drying under reduced pressure was performed, thereby obtaining Compound 10 (37.24 kg) (yield: 66.2%).

$^1$H-NMR (400 MHz, $CDCl_3$) δ ppm: 7.70 (s, 1H), 7.64 (s, 1H), 6.89 (s, 1H), 4.15 (s, 3H).

HPLC (UV=254 nm): RT=4.8 min, HPLC measurement conditions 10

Reference Example 4 Synthesis of Compound 9

[Chemical Formula 39]

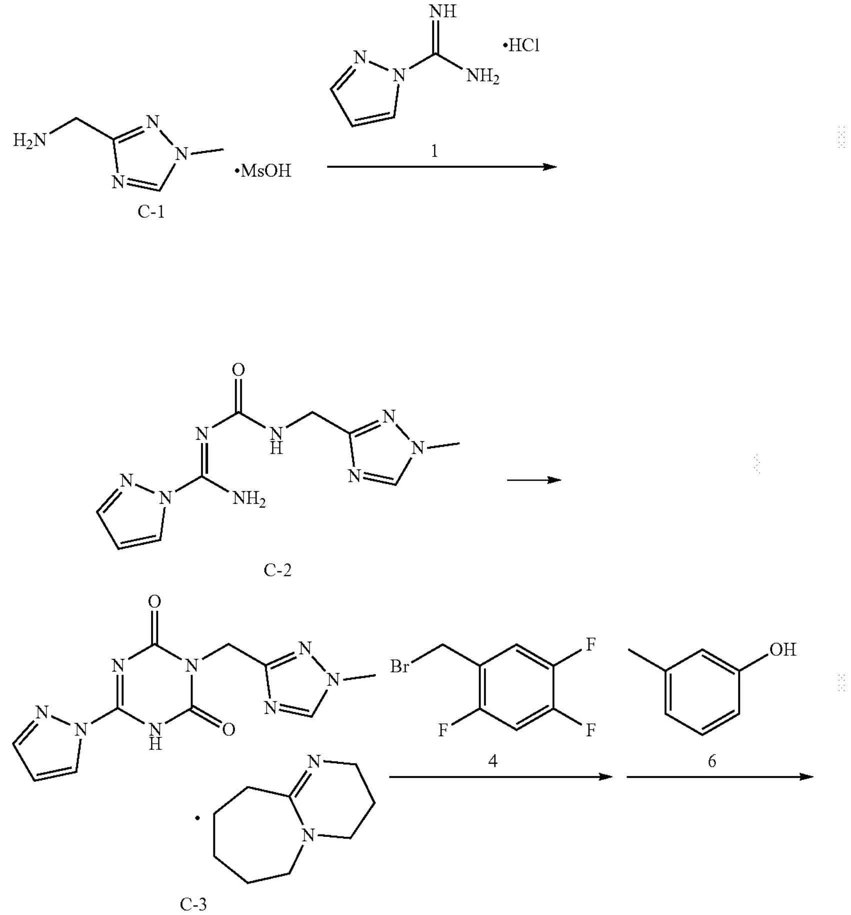

C-1

C-2

C-3

-continued

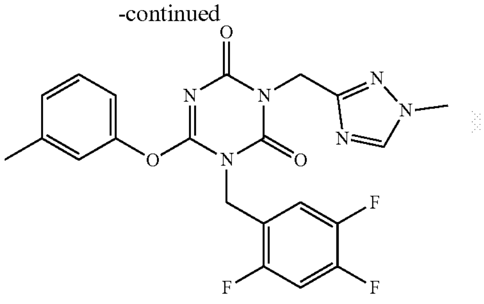

9

Step 1: Synthesis of Compound C-2

Compound C-1 (10.00 g, 48.0 mmol, mesylate), N,N'-carbonyldiimidazole (8.18 g, 50.4 mmol), acetonitrile (60.00 mL), and diisopropylethylamine (6.83 g, 52.8 mmol) were mixed, and the mixture was stirred at 10° C. for 60 minutes. Compound 1 (8.09 g, 55.2 mmol, hydrochloride) and diisopropylethylamine (7.14 g, 55.2 mmol) were mixed with the reaction solution, and the mixture was stirred at 50° C. for 210 minutes. The reaction solution was cooled and concentrated to 45 g. 2-Propanol (100 mL) was added thereto, and the mixture was concentrated to 60 g, then 2-propanol (100 mL) was added thereto. The slurry was cooled to 0° C., and the solid was collected by filtration, washed with 2-propanol, and dried, thereby obtaining Compound C-2 (10.48 g, 42.2 mmol, yield: 88%).

HPLC (UV=210 nm): RT=14.5 min, HPLC measurement conditions 11

Step 2: Synthesis of Compound C-3

Compound C-2 (8.00 g, 32.2 mmol), N,N'-carbonyldiimidazole (6.79 g, 41.9 mmol), tetrahydrofuran (80.0 mL), and 1,8-diazabicyclo[5,4,0]-7-undecene (5.40 g, 35.4 mmol) were mixed, and the mixture was stirred at 25° C. for 120 minutes. Tetrahydrofuran (80.0 mL) was added dropwise, and the reaction solution was cooled to 0° C., thereby forming a crystallized slurry. The solid was collected by filtration, washed with tetrahydrofuran, and then dried by heating, thereby obtaining a crystal of Compound C-3 (12.6 g, 29.6 mmol, 1,8-diazabicyclo[5.4.0]-7-undecene salt, yield: 92%).

HPLC (UV=210 nm): RT=1.9 min, HPLC measurement conditions 11

Step 3: Synthesis of Compound 9

Compound C-3 (1.00 g, 2.3 mmol, 1,8-diazabicyclo [5.4.0]-7-undecene salt), N,N-dimethylacetamide (5.0 mL), and Compound 4 (579.2 mg, 2.6 mmol) were mixed and stirred at 70° C. for 300 minutes. The reaction solution was cooled, and the operation of adding acetonitrile (10 mL) and concentrating to 9.4 g was repeated twice. Compound 6 (461 mg, 4.7 mmol) and diisopropylethylamine (456 mg, 3.5 mmol) were added to the concentrated liquid, and the mixture was stirred at 60° C. for 160 minutes. The reaction solution was cooled to 25° C., acetic acid (703 mg, 11.7 mmol), water (8.0 mL), and seed crystals were added thereto, and the obtained crystallized slurry was cooled to 0° C. Water (12.0 mL) was added to the slurry, and the solid was collected by filtration, washed with a 20% acetonitrile aqueous solution, and dried, thereby obtaining Compound 9 (0.86 g, 1.9 mmol, yield: 79.5%).

HPLC (UV=255 nm): RT=14.5 min, HPLC measurement conditions 8

Reference Example 5 Synthesis of Compound S-3

[Chemical Formula 40]

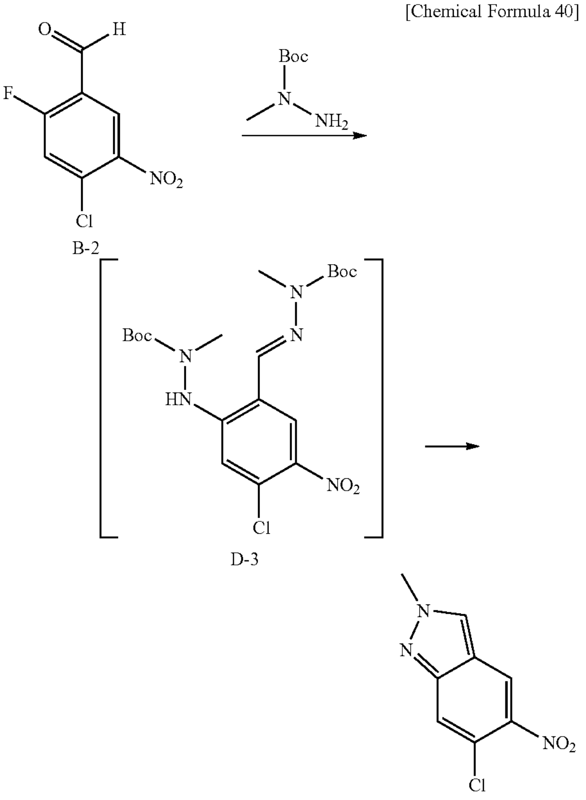

B-2

D-3

S-3

Step 1: Synthesis of Compound S-3

Compound B-2 was obtained in the same manner as in Step 1 of Reference Example 3. Subsequently, Compound B-2 (30 g, 147 mmol) and NMP (120 mL) were mixed, Boc-carboxylate (56 g, 383 mmol) was added thereto under ice cooling, and the mixture was stirred at room temperature for 30 minutes. Diisopropylethylamine (38.6 mL, 221 mmol) was added to the reaction solution and stirred at 90° C. for 20 hours. The reaction solution was adjusted to 80° C., water (240 mL) was added thereto, the mixture was then cooled to room temperature, and precipitated insoluble matters were separated by filtration. The obtained solid was washed three times with a mixed liquid of NMP/water=1/2 (15 mL), and further washed three times with water (30 mL). The obtained solid was suspended in isopropyl acetate (60 mL) and heptane (240 mL) and stirred at room temperature, then washed three times with isopropyl acetate/heptane=1/4 (30 mL), thereby obtaining Compound D-3. The obtained solid was suspended in isopropyl acetate (100 mL). The obtained suspension was added to a mixed solution of mesylic acid (96 mL, 1474 mmol) and isopropyl acetate (100 mL) at 55° C., washed with isopropyl acetate (60 mL), and stirred for 25 minutes at the same temperature. Under ice cooling, water (240 mL), a sodium hydroxide aqueous solution (239 mL, 1916 mmol) and isopropyl acetate (150 mL) were added to the reaction solution, and the mixture was stirred at 40° C. Isopropyl acetate (150 mL) was added to the obtained reaction solution. The obtained organic layer was washed three times with water (90 mL) and concentrated to 45 g. Isopropyl acetate (12 g) and heptane (210 mL) were added, the obtained insoluble matters were separated by filtration, and the solid was washed three times with isopropyl acetate/heptane=1/7 (30 ml) and dried, thereby obtaining Compound S-3 (25.3 g, 120 mmol, yield: 81.1%).

$^1$H-NMR (400 MHz, $CDCl_3$) δ ppm: 8.34 (s, 1H), 8.13 (s, 1H), 7.84 (s, 1H), 4.28 (s, 3H).

Reference Example 6 Synthesis of Compound 10

[Chemical Formula 41]

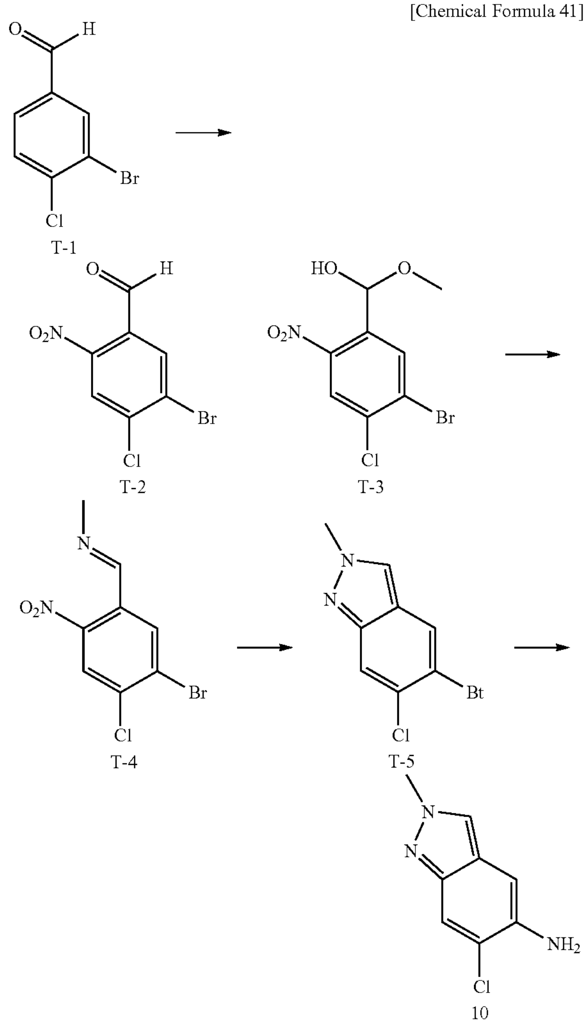

T-1 T-2 T-3 T-4 T-5 10

Step 1: Synthesis of Compounds T-2 and T-3

Under ice cooling, Compound T-1 (40 g, 182 mmol), concentrated sulfuric acid (200 mL, 3677 mmol), and 69% nitric acid (23.3 g, 255 mmol) were mixed, and the mixture was stirred at a temperature from ice cooling to room temperature for 3 hours, and then allowed to stand overnight. The mixed liquid was injected into 520 mL of ice water, dichloromethane (200 mL) was added thereto, and a liquid separation operation was performed. The obtained dichloromethane solution was washed twice with a 5% sodium hydrogen carbonate aqueous solution (400 mL), and concentrated and dried. Methanol (120 mL) was added to the obtained solid, and then the mixture was concentrated until the content amount thereof reached 116 g. Methanol was added to the obtained slurry until the content amount reached 333 g, then water (240 mL) was added, the obtained insoluble matters were separated by filtration, and the solid was washed with methanol/water=1/1 (200 mL) and dried, thereby obtaining a mixture of Compound T-2/T-3=1/2.78 (30.67 g, yield: 58.5%).

LC/MS (ESI): MS not detected as m/z, RT=2.04 min, LC/MS measurement conditions 1

Step 2: Synthesis of Compound T-4

Under a nitrogen stream, 2-propanol (1.4 mL) was added to a mixture (200 mg) of T-2/T-3=1/2.78, the temperature was raised to 60° C., triethylamine (0.289 mL, 2.07 mmol) was added thereto, and the mixture was stirred for 1.5 hours. Thereafter, a solution obtained by dissolving methylamine hydrochloride (94 mg, 1.39 mmol) in water (0.4 mL) was added to the reaction solution at 60° C., and the mixture was stirred for 3 hours. Water (8 mL) was added to the obtained reaction solution at 60° C., then the mixture was cooled to room temperature, and stirred for 30 minutes. The precipitated insoluble matters were separated by filtration, and the obtained solid was washed with water (5 mL) and dried, thereby obtaining Compound T-4 (194 mg, 0.699 mmol, yield: 100%).

LC/MS (ESI): m/z=277 (M+H), RT=2.46 min, LC/MS measurement conditions 2

Step 3: Synthesis of Compound T-5

Under a nitrogen stream, Compound T-4 (500 mg, 1.80 mmol), 2-propanol (2.5 mL), and tributylphosphine (802 mg, 3.96 mmol) were mixed, and the mixture was stirred at 80° C. for 1.5 hours. After cooling to room temperature, solvent substitution was performed three times with toluene (3 mL), and concentration was performed until the residue after concentration reached 5 g. Thereafter, the reaction solution was ice-cooled to 4° C., and a 4 mol/L hydrochloric acid-ethyl acetate solution (1.5 mL) was added, and the mixture was stirred for 20 minutes. The obtained crystallized slurry was separated by filtration, washed with toluene (2.5 mL), and dried, thereby obtaining a solid. The obtained solid was added portionwise to a mixed solution of water (4.3 mL) and sodium hydrogen carbonate (0.192 g, 2.29 mmol), and the pH was adjusted to 7 to 8, followed by stirring for 30 minutes, thereby obtaining a crystallized slurry. The mixture was separated by filtration, washed with water (8.6 mL), and dried, thereby obtaining Compound T-5 (351 mg, 1.43 mmol, yield: 79.4%).

LC/MS (ESI): m/z=245 (M+H), RT=1.90 min, LC/MS measurement conditions 1

Step 4: Synthesis of Compound 10

Under a nitrogen stream, Compound T-5 (2.015 g, 8.21 mmol), DME (20 mL), sodium tert-butoxide (1.104 g, 11.49 mmol), benzophenone imine (1.645 mL, 9.80 mmol), BINAP (0.153 g, 0.246 mmol), and diacetoxy palladium (0.036 g, 0.160 mmol) were mixed, stirred at 80° C. for 9 hours, and allowed to stand overnight. Ethanol (10 mL) was added to the obtained suspension, and the mixture was cooled to 5° C. 30% Sulfuric acid (20 mL) was added to the suspension portionwise, and the mixture was stirred at room temperature overnight. Ethyl acetate (40 mL) and water (20 mL) were added to the obtained reaction solution, and a liquid separation operation was performed. The obtained aqueous layer was washed with ethyl acetate (10 mL), and the organic layer was washed with 10% sulfuric acid (10 mL). The obtained aqueous layers were combined, and after ice cooling, neutralized using a 48% sodium hydroxide aqueous solution until the pH reached 8. Ethyl acetate (20 mL) was added, and precipitated sodium sulfate was separated by filtration, and a liquid separation operation was performed. Ethyl acetate (20 mL) was added to the obtained aqueous layer, and a liquid separation operation was performed. The obtained organic layers were combined, concentrated, and further solvent substitution was repeated four times with ethyl acetate (10 mL). Heptane (12 mL) was added, and the obtained crystallized slurry was stirred for 1 hour under ice cooling. The mixture was separated by filtration, washed with ethyl acetate/heptane=1/3 (6 mL), and dried, thereby obtaining Compound 10 (1.18 g, 6.5 mmol, yield: 79.2%).

LC/MS (ESI): m/z=182 (M+H), RT=0.88 min, LC/MS measurement conditions 1

Reference Example 7 Synthesis of Compound U-4

[Chemical Formula 42]

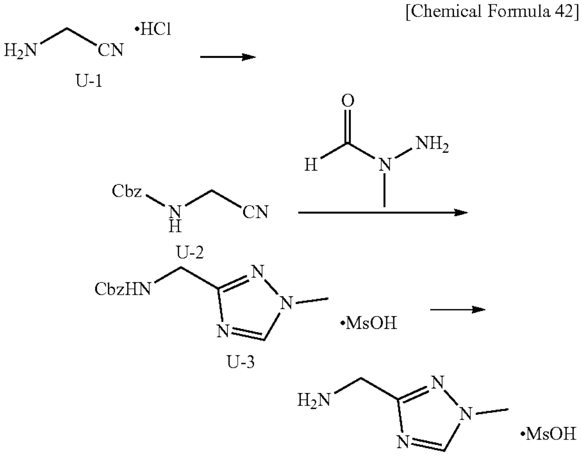
U-1
U-2
U-3
C-1

Step 1: Synthesis of Compound U-2

Compound U-1 (2.09 g, 22.6 mmol, hydrochloride), CPME (12.04 g), and water (7 g) were mixed, and a solution obtained by dissolving potassium carbonate (4.25 g, 30.8 mmol) in water (7 g) was slowly added so that the temperature of the reaction solution was 20 to 30° C. The obtained mixed solution was vigorously stirred, CbzCl (3.50 g, 20.5 mmol) was slowly added thereto so that the temperature of the reaction solution was 20 to 30° C., and the mixture was stirred at room temperature for 1 hour. The obtained solution was subjected to a liquid separation operation, and the organic layer was washed with water (14 g) and then concentrated. CPME (15.05 g) was added to the residue, and the residue was further concentrated to 10.5 g. The obtained solution was heated to 45° C., heptane (9.58 g) was added thereto over 30 minutes while maintaining the temperature, and then the mixture was further stirred for 30 minutes. Heptane (19.15 g) was added, and the obtained crystallized slurry was stirred for 30 minutes under ice cooling. The crystallized slurry was separated by filtration, and the obtained solid was washed with a mixed solution of CPME-heptane (3 g-9.58 g) and dried, thereby obtaining Compound U-2 (3.41 g, 17.93 mmol, yield: 86%).

HPLC (UV=254 nm): RT=9.51 min, HPLC measurement conditions 5

Step 2: Synthesis of Compound U-3

Methanol (31.66 g) was added to Compound U-2 (8.00 g, 42.1 mmol), and the mixture was cooled to 0° C. Thereafter, a 28% methanol solution of sodium methoxide (2.43 g, 12.6 mmol) was added thereto, and the mixture was stirred for 4 hours at the same temperature. To the obtained solution, a solution obtained by dissolving N-methylformohydrazide (3.74 g, 50.5 mmol) in methanol (19 g) was added at 0 to 5° C., and acetic acid (2.53 g, 42.1 mmol) was further added at the same temperature, then the mixture was stirred at 0° C. for 2 hours. The obtained solution was heated to 60° C. and stirred at the same temperature for 4 hours. The reaction solution was concentrated to 32 g, and then ethyl acetate (57.73 g) and a 5% sodium hydrogen carbonate aqueous solution (67.53 g) were added thereto. The obtained mixed solution was stirred for 10 minutes, and a liquid separation operation was performed. The obtained aqueous layer was also extracted with ethyl acetate (57.73 g). The combined organic layers were concentrated to 40 g. The operation of adding MEK (64.4 g) and further concentrating to 40 g was repeated twice. A solution obtained by dissolving mesylic acid (4.04 g, 42.0 mmol) in MEK (32.2 g) was added to the obtained concentrated liquid at 20 to 30° C., and the mixture was stirred at room temperature for 30 minutes. The precipitated crystallized slurry was separated by filtration, and the obtained solid was washed with MEK (25.76 g) and dried, thereby obtaining Compound U-3 (10.1 g, 29.5 mmol, mesylate, yield: 70%).

HPLC (UV=254 nm): RT=7.90 min, HPLC measurement conditions 5

Step 3: Synthesis of Compound C-1

Compound U-3 (10 g, 29.2 mol, mesylate) and methanol (79.15 g) were mixed, and stirred at room temperature, and then nitrogen substitution was performed. Palladium-carbon (palladium 10%) (0.5 g, 5 wt %) was added thereto, hydrogen substitution was performed, and then the mixture was stirred at room temperature for 7 hours. After nitrogen substitution, the palladium-carbon catalyst was removed by a Celite (registered trademark) filtration operation. The obtained filtrate was concentrated to 50 g. The operation of adding MEK (40.25 g) and concentrating to 40 g was repeated twice. The obtained crystallized slurry was separated by filtration, and washed with MEK (25.76 g) and dried, thereby obtaining Compound C-1 (5.3 g, 25.5 mmol, mesylate, yield: 87%).

HPLC (UV=254 nm): RT=2.75 min, HPLC measurement conditions 11

The result of the single crystal structural analysis of fumaric acid cocrystal Form I of the compound represented by Formula (VII) is shown below.

R1 (I>2.00s(I)) was 0.0470, and it was confirmed that there is neither a lack of electronic density neither misplacing of atom from final difference Fourier.

Crystallographic data are shown in Table 2.

TABLE 2

| Space group | P-1 |
|---|---|
| a (Å) | 8.4374(2) |
| b (Å) | 11.6780(3) |
| c (Å) | 15.1612(4) |
| α (°) | 83.827(2) |
| β (°) | 78.868(2) |
| γ (°) | 77.147(2 |
| Volume ($Å^3$) | 1425.77(6) |
| Z | 2 |
| Density (calculated value) ($g/cm^3$) | 1.509 |
| Measurement temperature (K) | 298 |

Herein, Volume means the unit lattice volume, and Z means the number of molecules in the unit lattice.

Furthermore, the atomic coordinates of non-hydrogen atoms are shown in Table 3 and Table 4. Herein, U (eq) means an equivalence isotropic temperature factor.

TABLE 3

| Atom | x | y | z | U(eq) |
|---|---|---|---|---|
| Cl36 | 8115.3(9) | 8341.6(8) | 5010.7(5) | 79.9(3) |
| F32 | 8958.5(19) | 7981.3(17) | 307.5(9) | 78.5(5) |
| O35 | 7267(2) | 5961.4(16) | 1399.9(10) | 56.3(5) |
| O34 | 5322(3) | 4254.8(16) | 4098.2(11) | 63.3(5) |
| O38 | 3536(2) | 9367.5(19) | 8936.3(12) | 64.2(5) |
| N12 | 6506(2) | 7056.8(18) | 2611.0(12) | 44.2(5) |
| F33 | 13870(2) | 7642(2) | 1402.1(13) | 100.3(7) |
| N16 | 5475(2) | 6174.4(18) | 3988.1(12) | 48.2(5) |
| N14 | 6120(3) | 5115.3(18) | 2713.0(12) | 47.3(5) |
| N9 | 2815(3) | 8924(2) | 7397.8(13) | 55.4(6) |
| N10 | 5772(3) | 8146(2) | 3856.1(13) | 55.1(6) |
| N1 | 1276(3) | 8864(2) | 7324.6(14) | 60.2(6) |
| F31 | 12197(3) | 7751(3) | 3084.6(13) | 124.9(9) |
| N23 | 3644(3) | 4434(2) | 1818.7(15) | 64.5(6) |
| N20 | 3122(3) | 4249(2) | 1061.4(15) | 64.9(6) |
| C11 | 6673(3) | 6043(2) | 2193.8(15) | 44.7(6) |
| C9 | 5879(3) | 7178(2) | 3527.6(15) | 44.2(6) |
| C10 | 5619(3) | 5119(2) | 3639.3(15) | 48.4(6) |
| N22 | 5784(3) | 3621(2) | 814.1(15) | 67.8(7) |
| O39 | 6151(3) | 8893(3) | 8285.8(15) | 109.2(10) |
| C12 | 6985(3) | 8068(2) | 2049.4(15) | 47.2(6) |
| C20 | 5248(3) | 4044(2) | 1633.9(16) | 50.7(6) |
| C7 | 5022(3) | 8298(2) | 4770.9(15) | 50.8(6) |
| C4 | 3693(3) | 8762(2) | 6554.3(16) | 49.4(6) |
| C13 | 8823(3) | 7976(2) | 1872.6(15) | 48.8(6) |
| C5 | 5385(3) | 8700(2) | 6267.8(17) | 56.4(7) |
| C19 | 6380(3) | 4009(2) | 2279.5(17) | 54.5(7) |
| C14 | 9741(3) | 7934(2) | 1013.2(16) | 54.7(7) |
| C3 | 2685(3) | 8593(2) | 5965.2(17) | 54.4(7) |
| C6 | 6015(3) | 8469(2) | 5392.0(16) | 54.3(7) |
| C23 | 5121(4) | 9287(3) | 8898.3(18) | 62.1(7) |
| O41 | 1842(3) | 4874(3) | 3529.1(18) | 119.8(10) |
| C8 | 3370(3) | 8376(2) | 5054.8(17) | 57.4(7) |
| C24 | 5542(3) | 9730(3) | 9679.7(17) | 61.9(7) |
| C18 | 9684(4) | 7917(3) | 2570.7(18) | 67.1(8) |
| C15 | 11431(3) | 7827(3) | 831.3(19) | 67.8(8) |
| C16 | 12217(3) | 7760(3) | 1541(2) | 67.9(8) |
| C2 | 1134(4) | 8867(3) | 6497.1(18) | 67.4(8) |

TABLE 4

| Atom | x | y | z | U(eq) |
|---|---|---|---|---|
| C17 | 11360(4) | 7806(3) | 2405(2) | 75.0(9) |
| C21 | 4400(4) | 3767(3) | 485.7(19) | 70.6(8) |
| O43 | −464(4) | 4618(4) | 3203.2(19) | 154.2(15) |
| C1 | 9(4) | 8943(3) | 8139(2) | 81.7(10) |
| C26 | 307(4) | 4766(4) | 3745(2) | 93.6(12) |
| C25 | −384(4) | 4909(4) | 4700(2) | 92.1(11) |
| C22 | 1397(4) | 4562(4) | 963(3) | 102.7(13) |

Next, the atomic coordinates of hydrogen atoms are shown in Table 5. Herein, U (iso) means an isotropic temperature factor. Furthermore, the numbers of hydrogen atoms in Table 5 were assigned in relation to the numbers of non-hydrogen atoms that are bonded.

TABLE 5

| Atom | x | y | z | U(iso) |
|---|---|---|---|---|
| H38 | 3370.9 | 9206.88 | 8452.86 | 96 |
| H16 | 5092.25 | 6215.55 | 4554.71 | 58 |
| H12A | 6452.59 | 8783.45 | 2347.49 | 57 |
| H12B | 6603.63 | 8119.01 | 1479.7 | 57 |
| H5 | 6053.99 | 8811.71 | 6658.45 | 68 |
| H19A | 6229.72 | 3381.57 | 2741.61 | 65 |
| H19B | 7509.94 | 3824.57 | 1962.58 | 65 |
| H41 | 2202.36 | 4700.41 | 3007.94 | 180 |
| H8 | 2702.01 | 8287.11 | 4656.27 | 69 |
| H24 | 6652.83 | 9619.42 | 9719.44 | 74 |
| H18 | 9115.24 | 7953.15 | 3160.4 | 81 |
| H15 | 12010.7 | 7800.84 | 243.55 | 81 |
| H2 | 176.44 | 8593.16 | 6310.6 | 81 |
| H21 | 4344.44 | 3553.57 | −79.51 | 85 |
| H1A | 260.69 | 3258.79 | 8539.89 | 122 |
| H1B | −1049.48 | 8985.26 | 7978.29 | 122 |
| H1C | −14.15 | 9635.57 | 8433.78 | 122 |
| H25 | −1486.76 | 4863.66 | 4886.06 | 110 |
| H22A | 719.4 | 4375.73 | 1521.91 | 154 |
| H22B | 1225.91 | 4127.33 | 499 | 154 |
| H22C | 1105.77 | 5390.24 | 801.98 | 154 |

Further, the interatomic bond length (unit: angstrom) is shown in Table 6.

TABLE 6

| Atom | Atom | Length/Å | Atom | Atom | Length/Å |
|---|---|---|---|---|---|
| Cl36 | C6 | 1.733(3) | N22 | C20 | 1.345(3) |
| F32 | C14 | 1.352(3) | N22 | C21 | 1.326(4) |
| O35 | C11 | 1.216(3) | O39 | C23 | 1.196(3) |
| O34 | C10 | 1.208(3) | C12 | C13 | 1.503(3) |
| O38 | C23 | 1.310(3) | C20 | C19 | 1.485(4) |
| N12 | C11 | 1.369(3) | C7 | C6 | 1.431(4) |
| N12 | C9 | 1.398(3) | C7 | C8 | 1.362(4) |
| N12 | C12 | 1.465(3) | C4 | C5 | 1.398(4) |
| F33 | C16 | 1.347(3) | C4 | C3 | 1.402(3) |
| N16 | C9 | 1.373(3) | C13 | C14 | 1.381(3) |
| N16 | C10 | 1.365(3) | C13 | C18 | 1.383(4) |
| N14 | C11 | 1.382(3) | C5 | C6 | 1.364(3) |
| N14 | C10 | 1.366(3) | C14 | C15 | 1.379(4) |
| N14 | C19 | 1.466(3) | C3 | C8 | 1.416(3) |
| N9 | N1 | 1.342(3) | C3 | C2 | 1.388(4) |
| N9 | C4 | 1.358(3) | C23 | C24 | 1.475(4) |
| N10 | C9 | 1.262(3) | O41 | C26 | 1.304(4) |
| N10 | C7 | 1.421(3) | C24 | C24[1] | 1.307(5) |
| N1 | C2 | 1.332(3) | C18 | C17 | 1.367(4) |
| N1 | C1 | 1.466(3) | C15 | C16 | 1.355(4) |
| F31 | C17 | 1.345(3) | C16 | C17 | 1.370(4) |
| N23 | N20 | 1.360(3) | O43 | C26 | 1.189(4) |
| N23 | C20 | 1.313(3) | C26 | C25 | 1.466(5) |
| N20 | C21 | 1.309(4) | C25 | C25[2] | 1.273(7) |
| N20 | C22 | 1.453(4) | | | |

In the fumaric acid cocrystal Form I of the compound represented by Formula (VII), one molecule of the compound represented by Formula (VII) existed in an asymmetric unit. The structure of the fumaric acid cocrystal Form I of the compound represented by Formula (VII) in the asymmetric unit is shown in FIG. 11.

Figure 11:
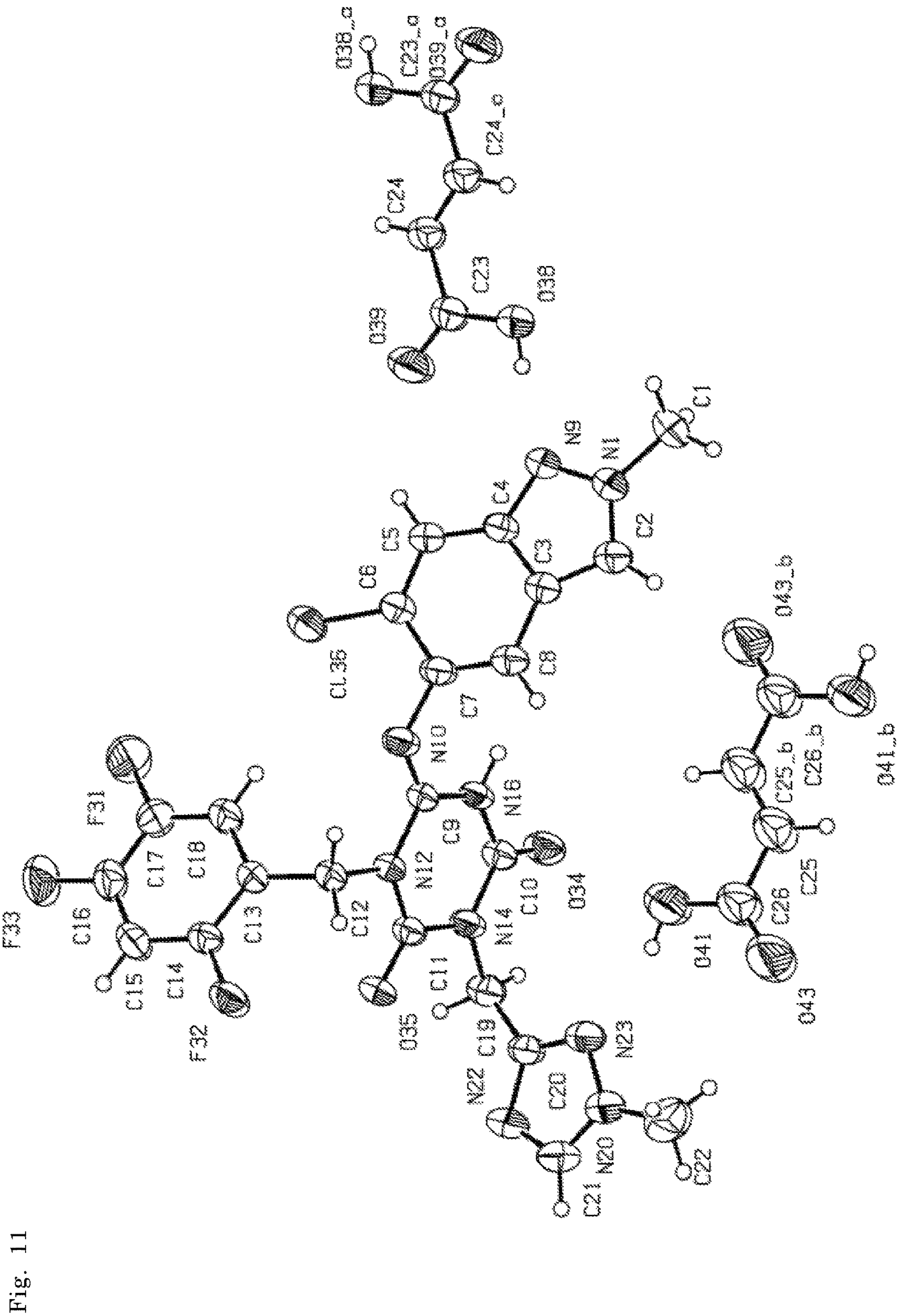
FIG. 11 shows a molecular structure of fumaric acid cocrystal Form I (Form I) of the compound represented by Formula (VII) in an asymmetric unit.

Note that, the numbers of non-hydrogen atoms in Table 3 to Table 4 and Table 6 correspond to the numbers shown in FIG. 11, respectively.

As shown in Table 6, the bond length of N10-C9 was about 1.26 Å, and the bond length of N16-C9 was about 1.37 Å.

Since the bond length of N10-C9 (about 1.26 Å) is shorter than that of N16-C9 (about 1.37 Å), the fumaric acid cocrystal Form I of the compound represented by Formula (VII) was identified as imino structure:

[Chemical Formula 43]

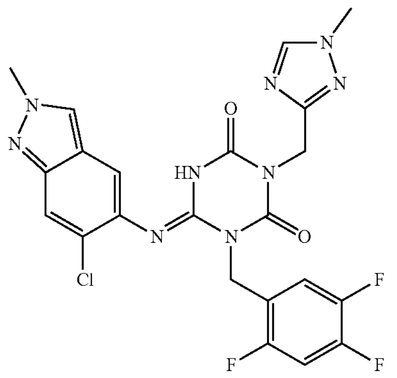

That is, even with the same compound, there are cases where the compound has an imino structure or an amino structure depending on crystallization conditions and the like. Even in the case of forming its salt or complex, there are cases where the compound has an imino structure or an amino structure depending on the types of the counter molecule of its salt or complex. Even with the same counter molecule, there are cases where the compound has an imino structure or an amino structure depending on crystallization conditions and the like. Furthermore, it may also be a mixture of a compound having an imino structure, its salt or complex, and a compound having an amino structure, its salt or complex.

The results of the X-ray powder diffraction of the fumaric acid cocrystal Form I of the compound represented by Formula (VII) which was obtained by the similar preparation method as in Step 5-2 of Example 1b are shown.

In the X-ray powder diffraction pattern, the peaks were observed at the diffraction angle (2θ): 7.7±0.2°, 9.5±0.2°, 10.0±0.2°, 10.9±0.2°, 13.8±0.2°, 14.6±0.2°, 18.6±0.2°, 22.6±0.2°, 23.4±0.2°, and 24.6±0.2°.

Figure 9:
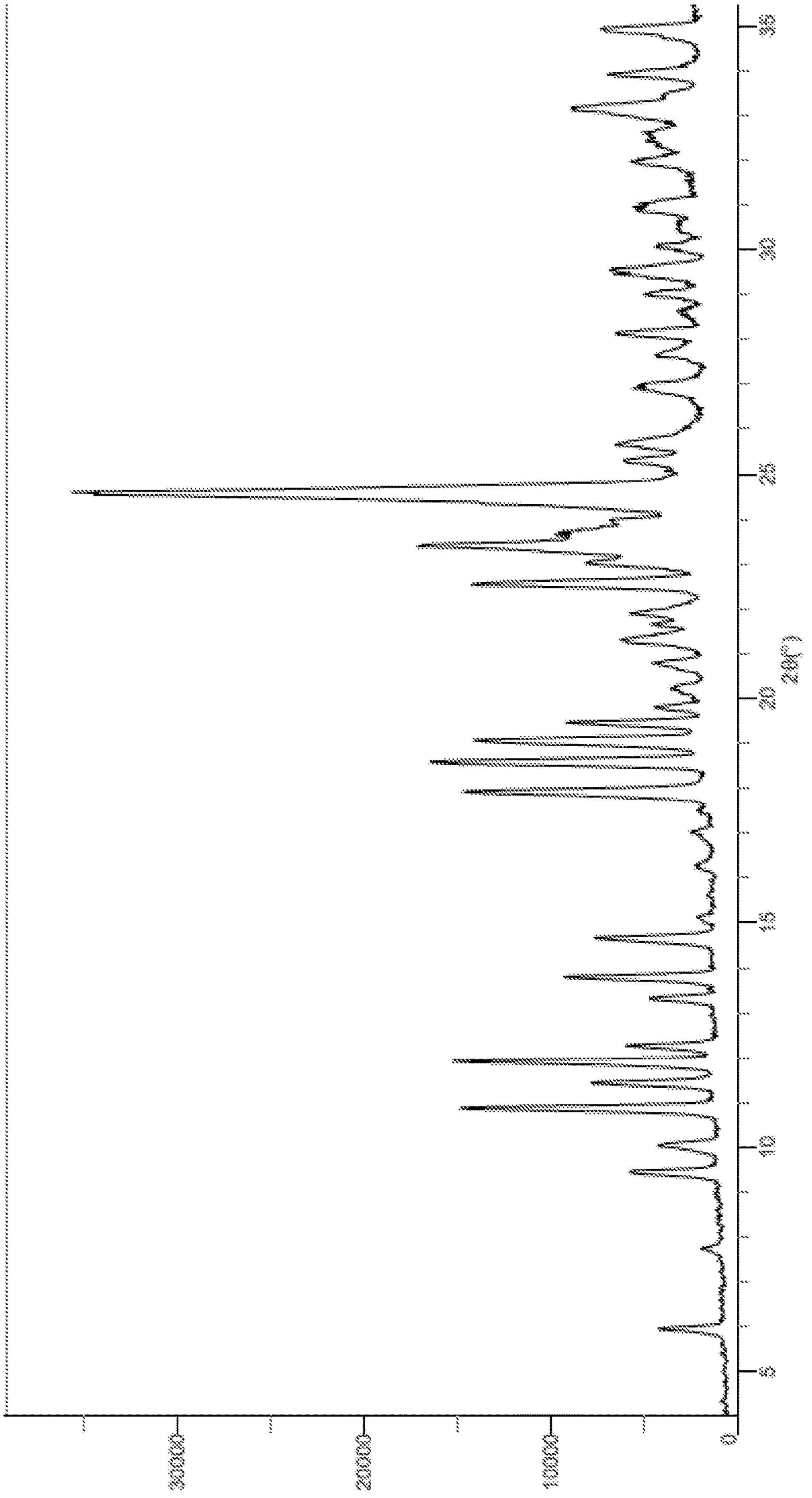
FIG. 9 shows X-ray powder diffraction patterns of fumaric acid cocrystal Form I (Form I) of a compound represented by Formula (VII) in Example b. The horizontal axis represents 2θ (°) and the vertical axis represents intensity (Count).

X-ray powder diffraction patterns of fumaric acid cocrystal Form I (Form I) of the compound represented by Formula (VII) are shown in FIG. 9. The horizontal axis represents 2θ (°) and the vertical axis represents intensity (Count).

The peak table of the X-ray powder diffraction patterns of FIG. 9 is shown in FIG. 10.

Furthermore, the X-ray powder diffraction results of the toluene solvate of the compound represented by Formula (VII) are shown.

In the X-ray powder diffraction pattern, the peaks were observed at the diffraction angle (2θ): 7.4±0.2°, 8.1±0.2°, 13.7±0.2°, 15.1±0.2°, 16.3±0.2°, 19.3±0.2°, 21.4±0.2°, 22.6±0.2°, 24.6±0.2°, 26.6±0.2°, 27.8±0.2°, and 29.5±0.2°.

Figure 20:
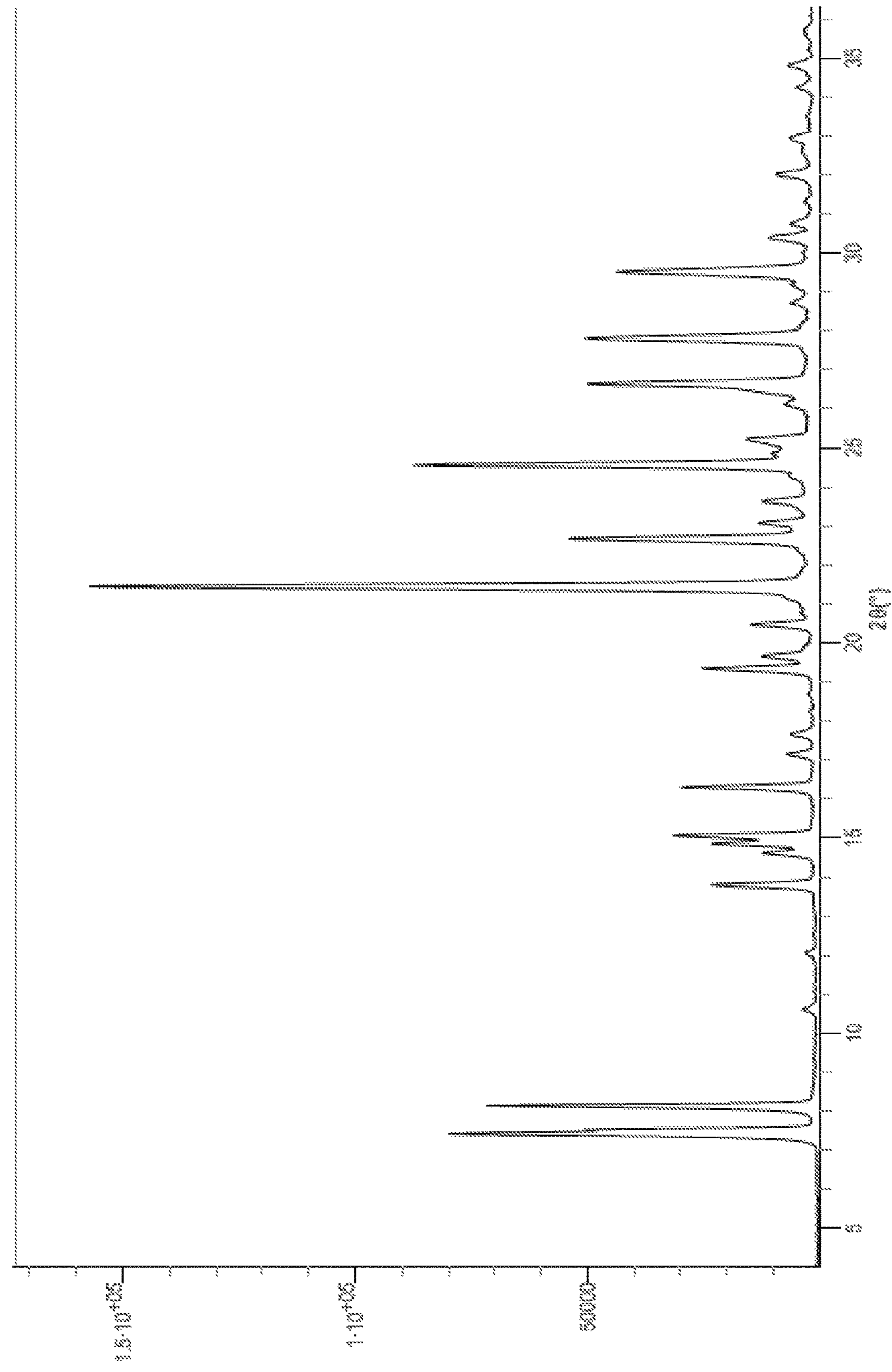
FIG. 20 shows X-ray powder diffraction patterns of a toluene solvate of the compound represented by Formula (VII). The horizontal axis represents 2θ (°) and the vertical axis represents intensity (Count).

X-ray powder diffraction patterns of a toluene solvate of the compound represented by Formula (VII) are shown in FIG. 20. The horizontal axis represents 2θ (°) and the vertical axis represents intensity (Count).

Regarding the toluene solvate of the compound represented by Formula (VII), the molecular structure (amino form/imino form) is not identified.

Hereinafter, biological test examples of the compound of the present invention are described.

The compound represented by Formula (VII) according to the present invention may have coronavirus 3CL protease inhibitory activity and may inhibit coronavirus 3CL protease.

Specifically, in the evaluation method described below, IC50 is preferably 50 μM or less, more preferably 1 μM or less, and even more preferably 100 nM or less.

Test Example 1: Inhibitory Activity of Cytopathic Effect (CPE) in Vero E6 Cells Expressing Human TMPRSS2 (Vero E6/TMPRSS2 Cells)

<Operation Procedure>

Diluting and Dispensing of Test Sample

The test sample is preliminarily diluted with DMSO to an appropriate concentration, and a 2- to 5-fold serial dilution series is prepared and then dispensed into a 384-well plate.

Diluting and Dispensing of Cells and SARS-CoV-2

VeroE6/TMPRSS2 cells (JCRB1819, $5\times10^3$ cells/well) and SARS-CoV-2 (100 $TCID_{50}$/well) are mixed in a culture medium (MEM, 2% FBS, penicillin-streptomycin), dispensed into a well containing the test sample, and then cultured in a $CO_2$ incubator for 3 days.

Dispensing and Measuring of Luminescence Signal of CellTiter-Glo (Registered Trademark) 2.0

After returning the plate cultured for 3 days to room temperature, CellTiter-Glo (registered trademark) 2.0 is dispensed into each well and mixed with a plate mixer. After a certain time interval, the luminescence signal (Lum) is measured with a plate reader.

<Calculation of Each Measurement Item>

Calculation of 50% SARS-CoV-2 Infected Cell Death Inhibitory Concentration ($EC_{50}$)

When x is taken as the logarithmic value of the compound concentration and y as % Efficacy, the inhibition curve is approximated by the following Logistic regression equation, and the value of x when substituting 50(%) for y is calculated as $EC_{50}$.

$$y=\min+(\max-\min)/\{1+(X50/x)^\wedge\mathrm{Hill}\}$$

$$\%\ \mathrm{Efficacy}=\{(\mathrm{Sample}-\mathrm{virus\ control})/(\mathrm{cell\ control}-\mathrm{virus\ control})\}*100\%$$

cell control: the average of Lum of cell control wells virus control: the average of Lum of virus control wells min: lower limit of y-axis, max: upper limit of y-axis, X50: x-coordinate of inflection point, Hill: slope of curve at midpoint between min and max The compounds of the present invention were tested essentially as described above. Results are shown below.

Compound I-005: 0.328 μM

Test Example 2: Inhibitory Activity Test Against SARS-CoV-2 3CL Protease

<Material>

Commercially Available Recombinant SARS-CoV-2 3CL Protease

Commercially Available Substrate Peptide

Dabcyl-Lys-Thr-Ser-Ala-Val-Leu-Gln-Ser-Gly-Phe-Arg-Lys-Met-Glu(Edans)-NH2 (SEQ ID NO: 1)

Internal Standard Peptide

Dabcyl-Lys-Thr-Ser-Ala-Val-Leu(13C6,15N)-Gln (SEQ ID NO: 2)

Dabcyl-Lys-Thr-Ser-Ala-Val-Leu(13C6,15N)-Gln can be synthesized with reference to the literature (Atherton, E.; Sheppard, R. C., "In Solid Phase Peptide Synthesis, A Practical Approach", IRL Press at Oxford University Pres, 1989. and Bioorg. Med. Chem., Volume 5, Issue 9, 1997, pp. 1883-1891, etc.). An example will be described below.

H-Lys-Thr-Ser-Ala-Val-Leu(13C6,15N)-Glu(resin)-OαOtBu (the Lys side chain is Boc-protected, the Thr side chain is protected with a tert-butyl group, the Ser side chain is protected with a tert-butyl group, the C-terminal OH of Glu is protected with a tert-butyl group, and the carboxylic acid of the Glu side chain is condensed into the resin) is synthesized using Rink amide resin by Fmoc solid-phase synthesis. Modification of the N-terminus Dabcyl group condenses 4-dimethylaminoazobenzene-4'-carboxylic acid (Dabcyl-OH) on resins using EDC/HOBT. Final deprotection and excision from the resins are performed by treatment with TFA/EDT=95:5. Thereafter, purification is performed by reverse phase HPLC.

RapidFire Cartridge C4 TypeA

<Operation Procedure>

Preparation of Assay Buffer

In this test, an assay buffer consisting of 20 mM Tris-HCl, 100 mM sodium chloride, 1 mM EDTA, 10 mM DTT, and 0.01% BSA is used. For compounds with an $IC_{50}$ value of 10 nM or less, an assay buffer consisting of 20 mM Tris-HCl, 1 mM EDTA, 10 mM DTT, and 0.01% BSA is used.

Diluting and Dispensing of Test Sample

The test sample is preliminarily diluted with DMSO to an appropriate concentration, and a 2- to 5-fold serial dilution series is prepared and then dispensed into a 384-well plate.

Addition of Enzyme and Substrate and Enzymatic Reaction

To the prepared compound plate, 8 μM of substrate and 6 or 0.6 nM of enzyme solution are added and incubation is performed for 3 to 5 hours at room temperature. Thereafter, a reaction stop solution (0.067 μM Internal Standard, 0.1% formic acid, 10 or 25% acetonitrile) is added to stop the enzymatic reaction.

Measurement of Reaction Product

The plate in which the reaction has been completed is measured using RapidFire System 360 and mass spectrometer (Agilent Technologies, Inc., 6550 iFunnel Q-TOF), or RapidFire System 365 and mass spectrometer (Agilent Technologies, Inc., 6495C Triple Quadrupole). As the mobile phase at the time of measurement, A solution (75% isopropanol, 15% acetonitrile, 5 mM ammonium formate) and B solution (0.01% trifluoroacetic acid, 0.09% formic acid) are used.

Reaction products detected by the mass spectrometer are calculated using RapidFire Integrator or a program capable of performing equivalent analysis and are taken as Product area value. Furthermore, Internal Standard detected at the same time is also calculated and taken as Internal Standard area value.

<Calculation of Each Measurement Item>

Calculation of P/IS

The area values obtained in the previous section is calculated by the following equation to calculate P/IS.

$$P/IS = \text{Product area value}/\text{Internal Standard area value}$$

Calculation of 50% SARS-CoV-2 3CL Protease Inhibitory Concentration ($IC_{50}$)

When x is taken as the logarithmic value of the compound concentration and y as % Inhibition, the inhibition curve is approximated by the following Logistic regression equation, and the value of x when substituting 50(%) for y is calculated as $IC_{50}$.

$$y=\min+(\max-\min)/\{1+(X50/x)\hat{}\,\text{Hill}\}$$

$$\%\ \text{Inhibition}=\{1-(\text{Sample}-\text{Control}(-))/(\text{Control}(+)-\text{Control}(-))\}*100$$

Control(−): the average of P/IS of enzyme inhibited condition wells

Control(+): the average of P/IS of DMSO control wells min: lower limit of y-axis, max: upper limit of y-axis, X50: x-coordinate of inflection point, Hill: slope of curve at midpoint between min and max The compounds of the present invention were tested essentially as described above. Results are shown below.

Compound I-005: 0.010 μM

Test Example 1-2: Inhibitory Activity of Cytopathic Effect (CPE) in Vero E6 Cells Expressing Human TMPRSS2 (Vero E6/TMPRSS2 Cells)

<Operation Procedure>

Diluting and Dispensing of Test Sample

The test sample is preliminarily diluted with DMSO to an appropriate concentration, and a 3-fold serial dilution series is prepared and then dispensed into a 96-well plate.

Diluting and Dispensing of Cells and SARS-CoV-2

VeroE6/TMPRSS2 cells (JCRB1819, $1.5\times10^4$ cells/well) and SARS-CoV-2 hCoV-19/Japan/TY/WK-521/2020, hCoV-19/Japan/QK002/2020, hCoV-19/Japan/QHNO01/2020, hCoV-19/Japan/QHN002/2020, hCoV-19/Japan/TY7-501/2021, hCoV-19/Japan/TY7-503/2021, hCoV-19/Japan/TY8-612/2021, hCoV-19/Japan/TY11-927-P1/2021 (30-1000 $TCID_{50}$/well) are mixed in a culture medium (MEM, 2% FBS, penicillin-streptomycin), dispensed into a well containing the test sample, and then cultured in a $CO_2$ incubator for 3 days.

Dispensing and Measuring of Luminescence Signal of CellTiter-Glo (Registered Trademark) 2.0

After returning the plate cultured for 3 days to room temperature, CellTiter-Glo (registered trademark) 2.0 is dispensed into each well and mixed with a plate mixer. After a certain time interval, the luminescence signal (Lum) is measured with a plate reader.

<Calculation of Each Measurement Item>

Calculation of 50% SARS-CoV-2 Infected Cell Death Inhibitory Concentration ($EC_{50}$)

When x is taken as the logarithmic value of the compound concentration and y as % Efficacy, the inhibition curve is approximated by the following Logistic regression equation, and the value of x when substituting 50(%) for y is calculated as $EC_{50}$.

$$y=\min+(\max-\min)/\{1+(X50/x)\hat{}\,\text{Hill}\}$$

$$\%\ \text{Efficacy}=\{(\text{Sample}-\text{virus control})/(\text{cell control}-\text{virus control})\}*100\%$$

cell control: the average of Lum of cell control wells virus control: the average of Lum of virus control wells min: lower limit of y-axis, max: upper limit of y-axis, X50: x-coordinate of inflection point, Hill: slope of curve at midpoint between min and max The compounds of the present invention were tested essentially as described above. Results are shown below.

(SARS-CoV-2 hCoV-19/Japan/TY/WK-521/2020)

Fumaric acid cocrystal Form I of the compound represented by Formula (VII): 0.37 μM Test Example 2-2: Inhibitory Activity Test Against SARS-CoV-2 3CL Protease <Material>

Commercially Available Recombinant SARS-CoV-2 3CL Protease

Commercially Available Substrate Peptide

Dabcyl-Lys-Thr-Ser-Ala-Val-Leu-Gln-Ser-Gly-Phe-Arg-Lys-Met-Glu(Edans)-NH2 (SEQ ID NO: 1)

Internal Standard Peptide

Dabcyl-Lys-Thr-Ser-Ala-Val-Leu(13C6,15N)-Gln (SEQ ID NO: 2)

Dabcyl-Lys-Thr-Ser-Ala-Val-Leu(13C6,15N)-Gln can be synthesized with reference to the literature (Atherton, E.; Sheppard, R. C., "In Solid Phase Peptide Synthesis, A Practical Approach", IRL Press at Oxford University Pres, 1989. and Bioorg. Med. Chem., Volume 5, Issue 9, 1997, pp. 1883-1891, etc.). An example will be described below.

H-Lys-Thr-Ser-Ala-Val-Leu(13C6,15N)-Glu(resin)-OαOtBu (the Lys side chain is Boc-protected, the Thr side chain is protected with a tert-butyl group, the Ser side chain is protected with a tert-butyl group, the C-terminal OH of Glu is protected with a tert-butyl group, and the carboxylic acid of the Glu side chain is condensed into the resin) is synthesized using Rink amide resin by Fmoc solid-phase synthesis. Modification of the N-terminus Dabcyl group condenses 4-dimethylaminoazobenzene-4'-carboxylic acid (Dabcyl-OH) on resins using EDC/HOBT. Final deprotection and excision from the resins are performed by treatment with TFA/EDT=95:5. Thereafter, purification is performed by reverse phase HPLC.

RapidFire Cartridge C4 TypeA

<Operation Procedure>

Preparation of Assay Buffer

In this test, an assay buffer consisting of 20 mM Tris-HCl, 1 mM EDTA, 10 mM DTT, and 0.01% BSA is used.

Diluting and Dispensing of Test Sample

The test sample is preliminarily diluted with DMSO to an appropriate concentration, and a 3-fold serial dilution series is prepared and then dispensed into a 384-well plate.

Addition of Enzyme and Substrate and Enzymatic Reaction

To the prepared compound plate, 8 μM of substrate and 6 nM of enzyme solution are added and incubation is performed for 3 hours at room temperature. Thereafter, a reaction stop solution (0.072 μM Internal Standard, 0.1% formic acid, 10% acetonitrile) is added to stop the enzymatic reaction.

Measurement of Reaction Product

The plate in which the reaction has been completed is measured using RapidFire System 360 and mass spectrometer (Agilent Technologies, Inc., 6550 iFunnel Q-TOF). As the mobile phase at the time of measurement, A solution (75% isopropanol, 15% acetonitrile, 5 mM ammonium formate) and B solution (0.01% trifluoroacetic acid, 0.09% formic acid) are used.

Reaction products detected by the mass spectrometer are calculated using RapidFire Integrator and are taken as Product area value. Furthermore, Internal Standard detected at the same time is also calculated and taken as Internal Standard area value.

<Calculation of Each Measurement Item>

Calculation of P/IS

The area values obtained in the previous section is calculated by the following equation to calculate P/IS.

$$P/IS = \text{Product area value}/\text{Internal Standard area value}$$

Calculation of 50% SARS-CoV-2 3CL Protease Inhibitory Concentration ($IC_{50}$)

When x is taken as the logarithmic value of the compound concentration and y as % Inhibition, the inhibition curve is approximated by the following Logistic regression equation, and the value of x when substituting 50(%) for y is calculated as $IC_{50}$.

$$y = \min + (\max - \min)/\{1 + (X50/x)^{\wedge}\text{Hill}\}$$

$$\%\ \text{Inhibition} = \{1 - (\text{Sample} - \text{Control}(-))/\text{Control}(+) - \text{Control}(-))\} * 100$$

Control(−): the average of P/IS ratio in the wells without SARS-CoV-2 3CL protease and test substance Control(+): the average of P/IS ratio in the wells with SARS-CoV-2 3CL protease and without test substance min: lower limit of y-axis, max: upper limit of y-axis, X50: x-coordinate of inflection point, Hill: slope of curve at midpoint between min and max The compounds of the present invention were tested essentially as described above. Results are shown below.

Fumaric acid cocrystal Form I of the compound represented by Formula (VII): 0.0132 μM Example 5

The fumaric acid cocrystal Form I of the compound represented by Formula (VII) was weighed so that the amount of the compound represented by Formula (VII) became about 1.8 (w/v) %, and it was added to an aqueous solution obtained by dissolving 0.3 (w/v) % of polymer, and then was dispersed.

As the additives, amino alkyl methacrylate copolymer E (manufactured by Evonik), hydroxypropylcellulose (manufactured by Nippon Soda Co., Ltd.), hypromellose (manufactured by Shin-Etsu Chemical Co., Ltd.), polyvinyl alcohol (manufactured by Merck & Co., Inc.), polyvinylpyrrolidone (manufactured by BASF), and polyvinyl alcohol-methyl methacrylate-acrylic acid copolymer (manufactured by Nisshin Kasei Co., Ltd.) were used.

TABLE 7

| | High molecular |
|---|---|
| Example 5A | — |
| Example 5B | Aminoalkyl Methacrylate Copolymer E |
| Example 5C | Hydroxypropyl cellulose |
| Example 5D | Hypromellose |
| Example 5E | Polyvinyl alcohol |
| Example 5F | Polyvinylpyrrolidone |
| Example 5G | Polyvinyl alcohol/methyl methacrylate/ acrylic acid copolymer |

Test Example 3: Evaluation of Solubility

To 14 mL of fasted state simulated artificial intestinal fluid (FaSSIF), 1 mL of each dispersion of Example 5 was added and stirred at 37° C. and 400 rpm for 1 hour with a constant temperature stirrer. After stirring for 1 hour, the specimen was filtered with a 0.45-μm filter, and the concentration of the compound represented by Formula (VII) in the filtrate was measured by a liquid chromatography method.

(Measurement Method)

Detector: ultraviolet absorptiometer (measurement wavelength: 222 nm)

Column: ACQUITY UPLC BEH C18 2.1×50 mm, 1.7 μm

Column temperature: constant temperature at near 40° C.

Mobile phase A: 0.1 M ammonium formate solution,

Mobile phase B: acetonitrile

Feed of mobile phase: The mixing ratio of mobile phase A and mobile phase B was changed to 7:3 or as shown in the following table to control concentration gradient.

TABLE 8

| Time after injection (minutes) | Mobile phase A (vol %) | Mobile phase B (vol %) |
|---|---|---|
| 0 to 5.00 | 85 → 30 | 15 → 70 |
| 5.00 to 5.01 | 30 → 10 | 70 → 90 |
| 5.01 to 6.00 | 10 | 90 |
| 6.00 to 6.01 | 10 → 85 | 90 → 15 |
| 6.01 to 7.50 | 85 | 15 |

Flow rate: about 0.6 mL/min

Injection amount: 1 μL or 1.5 μL

Sample cooler temperature: about 10° C.

Washing solution of auto injector: water/methanol mixed solution (7:3)

Range of measured area: for 4 minutes or 7.5 minutes after injection of test solution Calculation Equation of Amount of Compound Represented by Formula (VII)

$$\text{Amount (\%) of compound represented by Formula (VII)} = ATII/\Sigma AT \times 100$$

ATII: peak area of compound represented by Formula (VII) of test solution

ΣAT: sum of peak area of test solution (except for blank and system peak)

(Results)

The solubility test results of the compound represented by Formula (VII) are shown in the following table. As a result, the solubility of the compound represented by Formula (VII) was significantly improved by adding the polymer.

TABLE 9

| | solubility (μg/mL) |
|---|---|
| Example 5A | 8.2 |
| Example 5B | 139.1 |
| Example 5C | 174.4 |
| Example 5D | 129.7 |
| Example 5E | 33.1 |
| Example 5F | 33.1 |
| Example 5G | 33.1 |

The particle size of the fumaric acid cocrystal Form I of the compound represented by Formula (VII) used in the present experiment was 3.44 μm of D50 and 8.33 μm of D90.

Example 6

(Method for Producing Tablet)

Tablets containing the fumaric acid cocrystal Form I of the compound represented by Formula (VII) were produced.

The formulations per tablet are shown in the following table. The fumaric acid cocrystal Form I of the compound represented by Formula (VII), D-mannitol (manufactured by Roquette Freres), croscarmellose sodium (manufactured by DuPont), hydroxypropylcellulose (manufactured by Nippon Soda Co., Ltd.), light anhydrous silicic acid (manufactured by Cabot Corporation), and magnesium stearate (manufactured by Mallinckrodt Pharmaceuticals) were sieved with a 30-mesh sieve and mixed, and then granulated.

The granulated and milled granules, crystalline cellulose (manufactured by Asahi Kasei Corp.), and magnesium stearate (manufactured by Mallinckrodt Pharmaceuticals) or light anhydrous silicic acid (manufactured by Cabot Corporation) were added and mixed, and then compression-molded into a diameter of 9.0 mm by a static compressor or a rotary tablet machine so as to obtain tablets having the following compositions.

TABLE 10

| Raw material name (mg) | Example 6A | Example 6B | Example 6C | Example 6D |
|---|---|---|---|---|
| Fumaric acid cocrystal Form I of compound represented by Formula (VII) | 152.3 | 152.3 | 152.3 | 152.3 |
| Content of compound represented by Formula (VII) | 125.0 | 125.0 | 125.0 | 125.0 |
| D-mannitol | 103.8 | 89.7 | 103.8 | 89.7 |
| Croscarmellose sodium | 51.3 | 31.3 | 31.3 | 31.3 |
| Hydroxypropyl cellulose | 17.2 | 31.3 | 17.2 | 31.3 |
| Light anhydrous silicic acid | 3.2 | 3.2 | 6.7 | 6.7 |
| Crystalline cellulose | 15 | 15 | 15 | 15 |
| Magnesium stearate | 9.2 | 9.2 | 19.7 | 19.7 |
| Total (mg) | 332 | 332 | 346 | 346 |

Test Example 4: Dissolution Test of Tablet (Dissolution Test Method)

A dissolution test was performed by the Japanese Pharmacopoeia, Eighteenth Edition, Dissolution Test, Method 2nd (the first fluid for dissolution test containing a surfactant, paddle method, paddle rotation number: 50 rpm, result: average of two tablets).

(Test Results)

Figure 21:
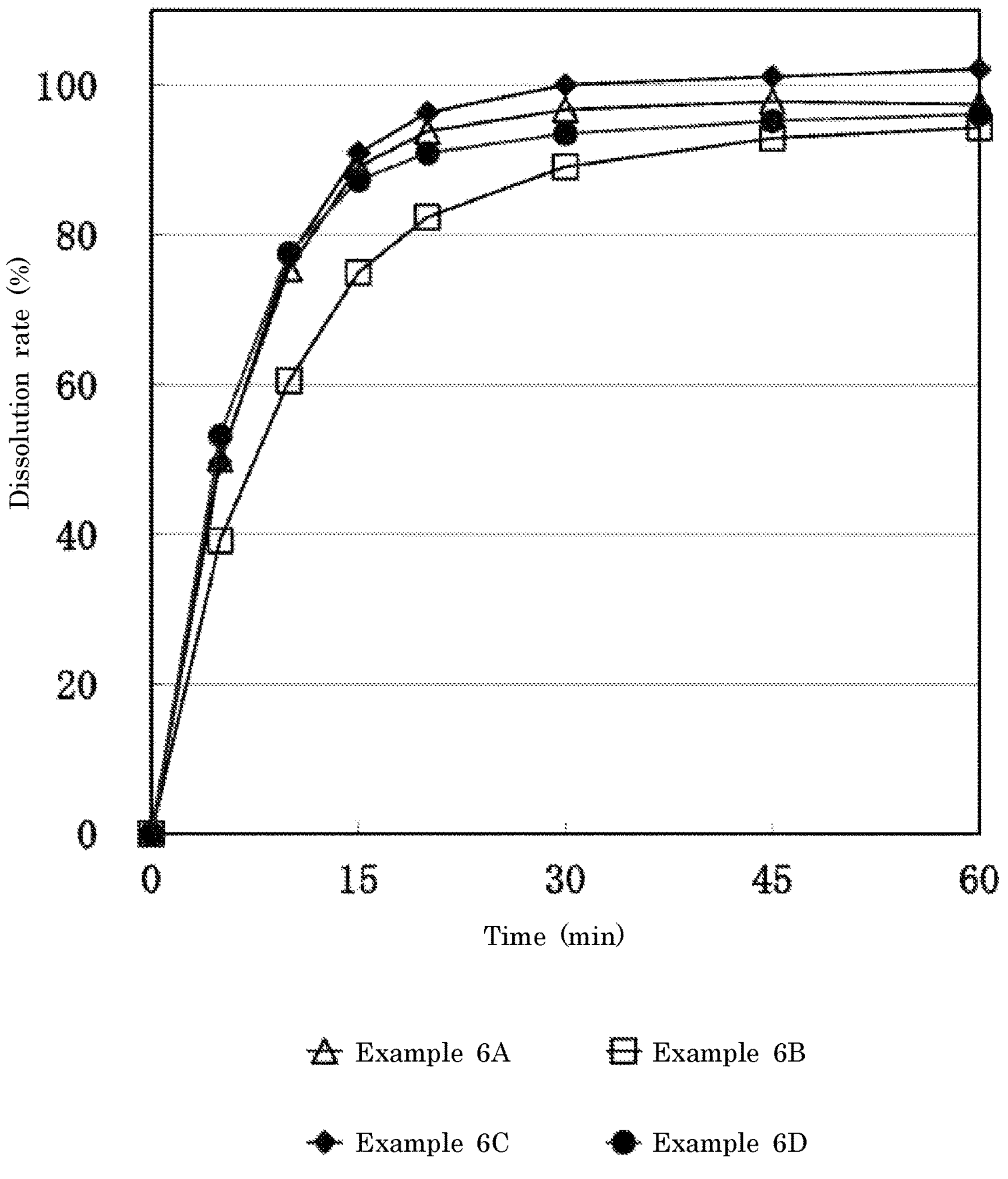
FIG. 21 shows a dissolution behavior of Example 6. The horizontal axis represents time (min) and the vertical axis represents a dissolution rate (%).

The dissolution test results of Examples 6A, 6B, 6C, and 6D are shown in FIG. 21. As a result, faster dissolution were shown in all Examples.

Figure 22:
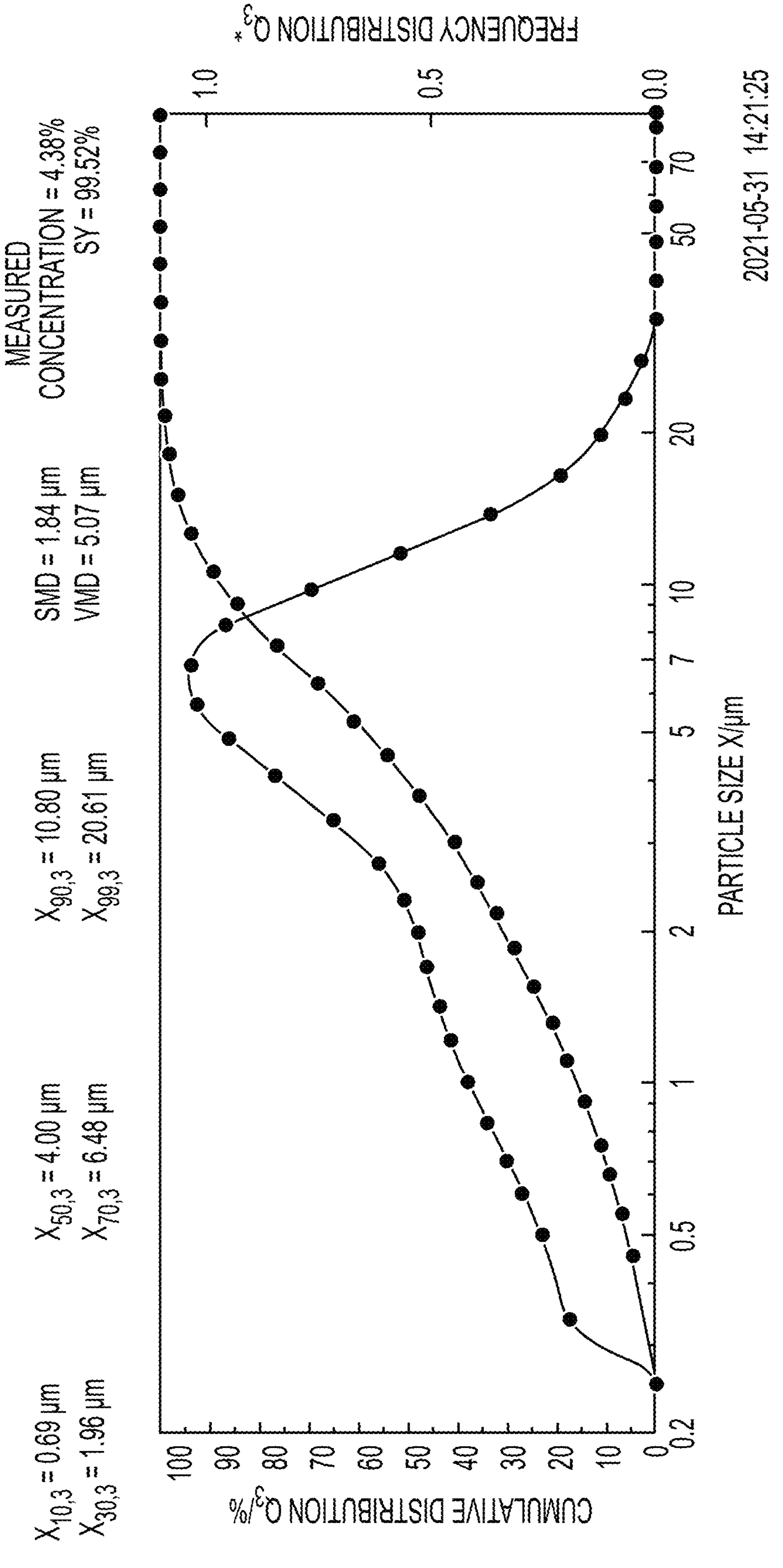
FIG. 22 shows a particle size distribution of an active ingredient (fumaric acid cocrystal Form I of the compound represented by Formula (VII)) used in formulations of Examples 6A and 6B.

The particle size distribution of the active ingredient (fumaric acid cocrystal Form I of the compound represented by Formula (VII)) used in formulations of Examples 6A and 6B used in Test Example 4 is shown in FIG. 22. The 10% particle size was 0.69 μm, the 50% particle size was 4.00 μm, and the 90% particle size was 10.80 μm.

Figure 23:
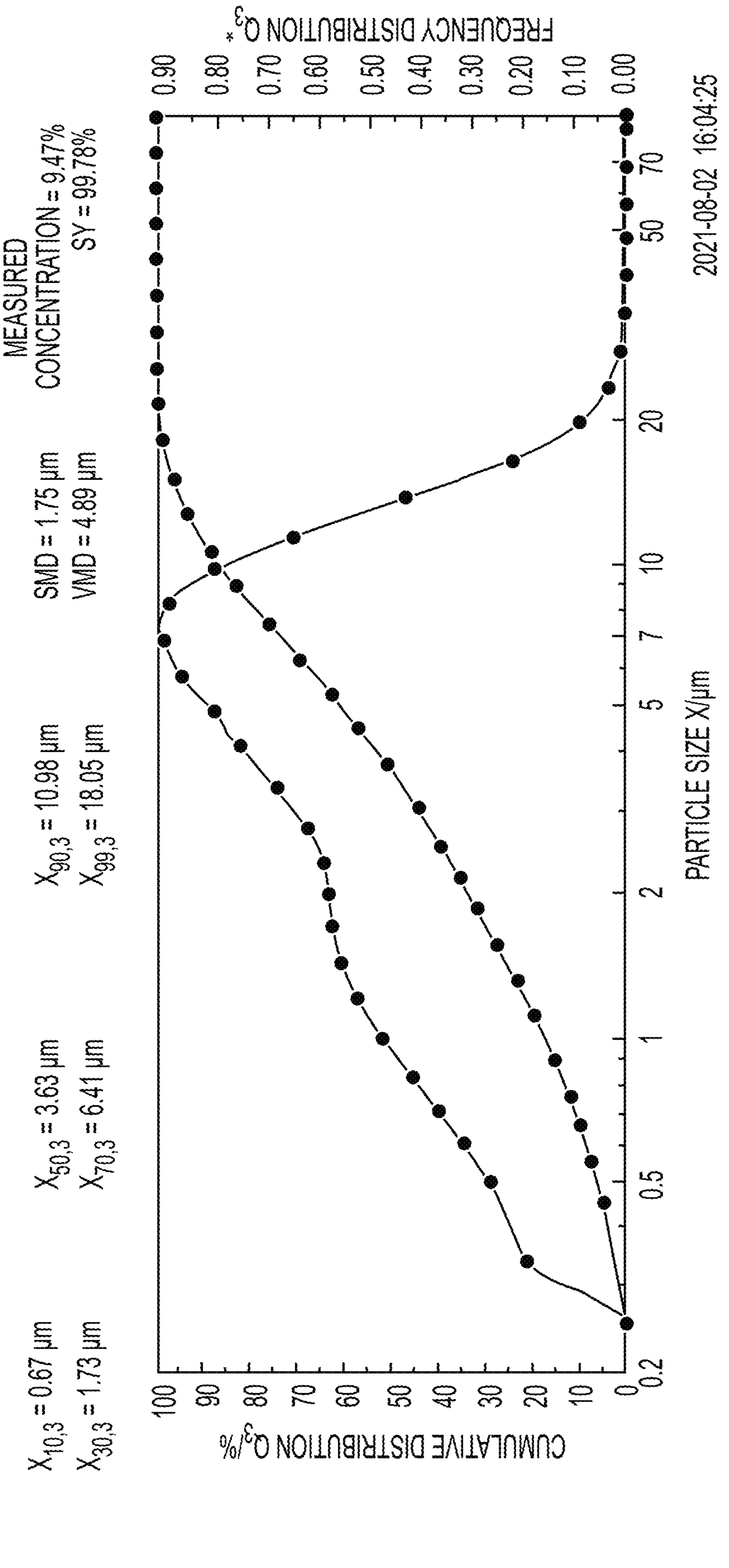
FIG. 23 shows a particle size distribution of an active ingredient (fumaric acid cocrystal Form I of the compound represented by Formula (VII)) used in formulations of Examples 6C and 6D.

The particle size distribution of the active ingredient (fumaric acid cocrystal Form I of the compound represented by Formula (VII)) used in formulations of Examples 6C and 6D used in Test Example 4 is shown in FIG. 23. The 10% particle size was 0.67 μm, the 50% particle size was 3.63 μm, and the 90% particle size was 10.98 μm.

Measurement conditions of the particle size distribution are as follows.

Manufacturer: Sympatec

Device: laser diffraction HELOS & RODOS particle size distribution measuring device Range: R2

Dispersion pressure: 3 bar

Trigger conditions: stop: 2 s measured concentration ≤1% or 10 s real time

Test Example 5: Effect of Stabilizing Agent in Formulations in Temporal Stability Test The results of confirming temporal stability of the formulation of Example 6A of the same lot as that used in Test Example 4 are shown.

a. Stability Test Method

The formulations of Example 6A were stored 1) in a closed brown glass bottle at 60° C. for 2 weeks with, or 2) in a opened brown glass bottle at 40° C. under 75% relative humidity for 1 month. Thereafter, amount of related substances of the compound represented by Formula (VII) in the formulation of the present invention was measured.

(Method for Preparing Sample Solution)

(Measurement Method)

Amount of related substances of the compound represented by Formula (VII) in the formulation of the present invention was measured with a solution chromatograph according to the following method and conditions.

Detector: ultraviolet absorptiometer (measurement wavelength: 222 nm)

Column: C18 column

Column temperature: constant temperature at near 40° C.

Mobile phase A: 0.01 mol/L ammonium formate solution,

Mobile phase B: acetonitrile

Regarding the mixing ratio of mobile phase A and mobile phase B, the mixing ratio of mobile phase B was gradually increased from 9:1 to 1:9, and the measurement was performed for 32 minutes.

Flow rate: 0.6 mL/min

For the amount of related substance, the total peak area of chromatogram of HPLC chart was taken as 100%, and the ratio (%) of the amount was calculated.

b. Result

The results of the stability test are shown in the following table. The total amount of related substances in the formulation of Example 6A did not increase even after storage 1) in a closed brown glass bottle at 60° C. for 2 weeks, and 2) in a opened brown glass bottle at 40° C. under 75% relative humidity for 1 month, and were stable.

TABLE 11

| | Total amount of related substances (%) |
|---|---|
| Initial | 0.36 |
| After storage at 60° C. for 2 weeks | 0.34 |
| After storage at 40° C. under 75% RH for 1 month | 0.35 |

From the above, the formulation of the present invention has high stability against humidity and temperature.

Example 7

Test Example 6 Clinical Study (Ph2a)

Efficacy and safety of repeated oral administration of a test drug (active ingredient: fumaric acid cocrystal Form I of the compound represented by Formula (VII)) to SARS-CoV-2-infected subjects having only mild/moderate and asymptomatic/mild symptoms were evaluated by a placebo-controlled, randomized, double-blind, comparative study.

The primary endpoint of Phase 2a Part was a change from baseline in SARS-CoV-2 virus titer at each time point in common among mild/moderate and asymptomatic SARS-CoV-2-infected subjects, and the antiviral effect of the test drug was confirmed.

Regarding mild/moderate SARS-CoV-2-infected subjects, patients who met all of the following criteria were selected.

(a) Male or female patients who are 12 years old or older and younger than 70 years old.

(b) Those diagnosed as SARS-CoV-2-positive within 120 hours prior to enrollment.

(c) Those whose time from onset of COVID-19 to enrollment is within 120 hours.

(d) Those having one or more moderate (COVID-19 symptom score: 2) or higher symptoms in any of the following symptoms due to COVID-19 (12 symptoms of COVID-19) (except for symptoms that were present before onset of COVID-19) at the time of enrollment.

Systemic symptoms: fatigue, muscle or body pain, headache, chill, feverishness

Respiratory symptoms: runny nose or nasal congestion, sore throat, cough, shortness of breath Gastrointestinal symptoms: nausea, vomiting, diarrhea Regarding asymptomatic SARS-CoV-2-infected subjects, patients who met all of the following criteria were selected.

(a) Male or female patients who are 12 years old or older and younger than 70 years old.

(b) Those diagnosed as SARS-CoV-2-positive within 120 hours prior to enrollment.

(c) Asymptomatic: Those who do not have the following COVID-19 symptoms (except for symptoms that were present before SARS-CoV-2 infection) within 2 weeks prior to enrollment.

Systemic symptoms: fatigue, muscle or body pain, headache, chill, feverishness, dysgeusia, dysosmia Respiratory symptoms: runny nose or nasal congestion, sore throat, cough, shortness of breath Gastrointestinal symptoms: nausea, vomiting, diarrhea Asymptomatic/mild symptoms only: Those not having moderate (COVID-19 symptom score: 2) or higher symptoms in any of the following symptoms due to COVID-19 (12 symptoms of COVID-19) (except for symptoms that were present before onset of COVID-19) within 2 weeks before randomization.

Systemic symptoms: malaise (fatigue), muscle or body pain, headache, chill/sweating, feverishness or fever Respiratory symptoms: runny nose or nasal congestion, sore throat, cough, shortness of breath (dyspnea)

Gastrointestinal symptoms: nausea, vomiting, diarrhea

Method of Administration of Investigational New Drug (i) Test Drug 250 mg tablet: The tablet contains fumaric acid cocrystal Form I of the compound represented by Formula (VII), and contains 250 mg of the compound represented by Formula (VII). The 250 mg tablet is a tablet prepared by doubling each composition similar as in Example 6C.

125 mg tablet: The tablet contains fumaric acid cocrystal Form I of the compound represented by Formula (VII), and contains 125 mg of the compound represented by Formula (VII). The 125 mg tablet is a tablet having the similar composition as in Example 6C.

(ii) Placebo

Placebo-D tablet: It is a tablet having an appearance indistinguishable from the above 250 mg tablet, and does not contain the fumaric acid cocrystal Form I of the compound represented by Formula (VII).

Placebo-B tablet: It is a tablet having an appearance indistinguishable from the above 125 mg tablet, and does not contain the fumaric acid cocrystal Form I of the compound represented by Formula (VII).

Dose and Method of Administration

In Phase 2a Part, subjects who were determined to be eligible as mild/moderate or asymptomatic SARS-CoV-2-infected subjects were randomly assigned at a ratio of 1:1:1 to any of the test drug 375/125 mg group, the test drug 750/250 mg group, and the placebo group.

Investigational New Drug by Treatment Group

375/125 mg Group 3 tablets each of 125 mg tablets and Placebo-D tablets are administered on Day 1, and 1 tablet each of 125 mg tablets and Placebo-D tablets is administered on Days 2 to 5 per day.

750/250 mg Group 3 tablets each of 250 mg tablets and Placebo-B tablets are administered on Day 1, and 1 tablet each of 250 mg tablets and Placebo-B tablets is administered on Days 2 to 5 per day.

Placebo Group 3 tablets each of Placebo-D tablets and Placebo-B tablets are administered on Day 1, and 1 tablet each of Placebo-D tablets and Placebo-B tablets is administered on Days 2 to 5 per day.

"Day 1" represents the first day of administration, and "Day 2 to Day 5" represent the second to fifth days counted from the first day of administration.

Primary Efficacy Endpoint (Phase 2a Part)

The primary efficacy endpoint of Phase 2a Part was a change from baseline in SARS-CoV-2 virus titer at each time point in common among mild/moderate and asymptomatic SARS-CoV-2-infected subjects. It is defined as an absolute change from baseline in observed value of SARS-CoV-2 virus titer at each time point.

Analysis of Primary Endpoint (Phase 2a Part)

For each of the mild/moderate SARS-CoV-2-infected subject population, the asymptomatic SARS-CoV-2-infected subject population, and the merged population thereof, summary statistics of a change from baseline in SARS-CoV-2 virus titer at each time point were calculated for the mITT population. Furthermore, a van Elteren test was applied to a combined population of mild/moderate and asymptomatic SARS-CoV-2-infected subjects, and pairwise comparisons were made between each test drug dose group and the placebo group for SARS-CoV-2 virus titer at each time point at a two-sided significance level of 5%. For the layers used in the van Elteren test, the mild/moderate SARS-CoV-2-infected subject population and the asymptomatic SARS-CoV-2-infected subject population were used.

Results of Primary Endpoint (1) Change From Baseline in SARS-CoV-2 Virus Titer at Each Time Point (Phase 2a Part)

69 cases were randomized in Phase 2a Part, and 22 cases (of which 1 case did not receive administration) were assigned to the 375/125 mg group, 23 cases were assigned to the 750/250 mg group, and 24 cases were assigned to the placebo group. Among the 69 cases, the number of cases positive for baseline RT-PCR was 44, and among them, the number of cases in which a baseline virus titer was detected was 40. The constitution of the 40 cases was 14 cases in the 375/125 mg group, 13 cases in the 750/250 mg group, and 13 cases in the placebo group. Note that the number of cases of these populations and the breakdown thereof were calculated on the basis of the RT-PCR measurement results and the virus titer measurement results available by Jan. 17, 2022.

As a final result of Phase 2a Part, among the 69 cases, the number of cases positive for baseline RT-PCR was 47, and among them, the number of cases in which a baseline virus titer was detected was 43. The constitution of the 43 cases was 15 cases in the 375/125 mg group, 14 cases in the 750/250 mg group, and 14 cases in the placebo group.

The visit date defined in the study protocol is denoted by Visit, and the correspondence relationship with the administration date (Day) and the permitted window are as follows. Op V means Optional Visit and indicates any visit date.

TABLE 12

| Visit | V1 | V2 | Op V1 | V3 | Op V2 | V4 | V5 | V6 | V7 | V8 |
|---|---|---|---|---|---|---|---|---|---|---|
| Day | 1 | 2 | 3 | 4 | 5 | 6 | 9 | 14 | 21 | 28 |
| Permitted window | −1 | +1 | — | +1 | — | +1 | ±1 | ±2 | ±3 | ±3 |
| | Administration | Administration | Administration | Administration | Administration | | | | | |

Figure 24:
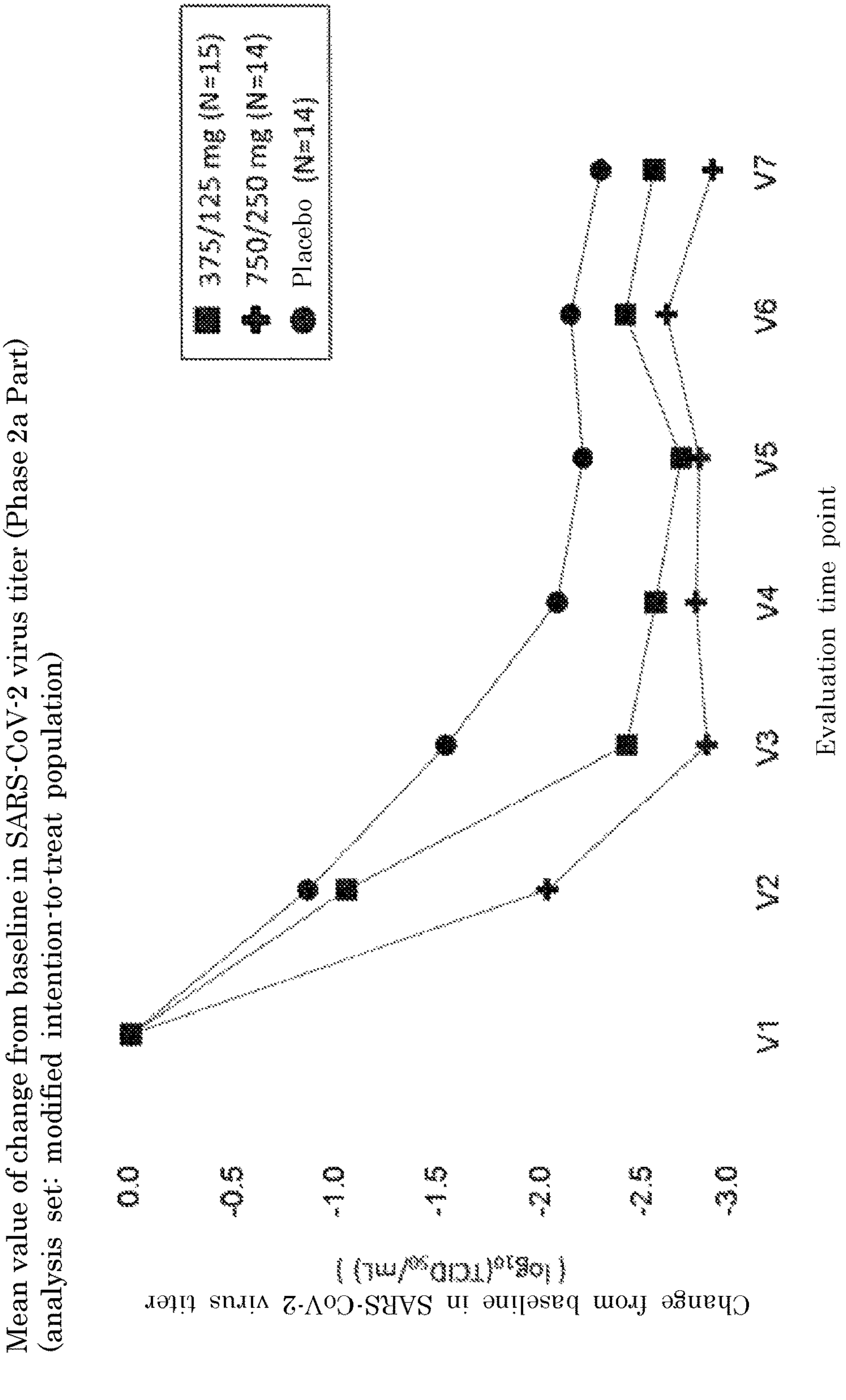
FIG. 24 shows a change from baseline in SARS-CoV-2 virus titer in Phase 2a Part. The vertical axis represents a change from baseline in virus titer ($\log_{10}$ ($TCID_{50}$/mL)), and the horizontal axis represents an evaluation time point.

FIG. 24 shows a time course of a mean value of a change from baseline in SARS-CoV-2 virus titer for each group in the modified intention-to-treat population (all subjects randomized and positive for both baseline RT-PCR and virus titer). This analysis included mild/moderate SARS-CoV-2-infected subjects and asymptomatic SARS-CoV-2-infected subjects, and only Visit that was set as an essential visit date was displayed. In addition, when the virus titer was less than the lower detection limit (0.8 $\log_{10}$ ($TCID_{50}$/mL)), the value of the virus titer was handled as 0.8 $\log_{10}$ ($TCID_{50}$/mL). At the time points of Visit 3 (Day 4 after the start of administration) in the 375/125 mg group, Visit 2 (Day 2 after the start of administration) and Visit 3 (Day 4 after the start of administration) in the 750/250 mg group, the virus titer statistically significantly decreased at a significance level of 0.05 as compared to the placebo group. In the RT-PCR measurement results and the virus titer measurement results that were available by the time point of Jan. 17, 2022, there was also a tendency for the virus titer to decrease as compared to the placebo group at all time points after Visit 3 (Day 4 after the start of administration) in the 375/125 mg group and after Visit 2 (Day 2 after the start of administration) in the 750/250 mg group.

A proportion of patients with a positive virus titer at each time point is shown below.

At the time point of Day 4, with respect to the proportion of patients with a positive virus titer of 0.8 or more in the placebo group, the proportion decreased by 80% in the 750/250 mg group and by 63% in the 375/125 mg group. At the time point of Day 6, with respect to the proportion of patients with a positive virus titer of 0.8 or more in the placebo group, the proportion decreased by 54% in the 750/250 mg group and by 100% in the 375/125 mg group.

At the time points of Day 4 and Day 6, the proportion of patients with a positive virus titer tended to be lower in both the 750/250 mg group and the 375/125 mg group compared to the placebo group. Therefore, it was suggested that by taking the pharmaceutical composition of the present invention, the number of patients who shed infectious viruses can be rapidly reduced.

Results of Secondary Endpoints (1) Time Until Negative Virus Titer is First Confirmed (Phase 2a Part)

Time until a negative virus titer of SARS-CoV-2 is first confirmed is shown in Table 13 below and FIG. 25.

Among 69 cases of Phase 2a Part, the results in 15 cases in the 375/125 mg group, 13 cases in the 750/250 mg group, and 14 cases in the placebo group are shown.

TABLE 13

| | 375/125 mg group | 750/250 mg group | Placebo group |
|---|---|---|---|
| Number of cases | 15 | 13 | 14 |
| Median (hour) | 61.3 | 62.7 | 111.1 |
| [95% confidence interval] | [38.0, 68.4] | [39.2, 72.3] | [23.2, 158.5] |
| Difference in median | −49.8 | −48.4 | — |
| [95% confidence interval] | [−96.7, 30.9] | [−95.9, 28.5] | |
| Stratified log rank test | P = 0.0159 | P = 0.0205 | — |

[In the stratified log rank test, the subject layer (mild/moderate, asymptomatic/mild only) is used as a stratification factor]

As shown in Table 13, in the 375/125 mg group, the median was 49.8 hours shorter than that in the placebo group, and there was a significant difference in the time until a negative virus titer was first confirmed (p=0.0159). In the 750/250 mg group, the median was 48.4 hours shorter than that in the placebo group, and there was a significant difference in the time until a negative virus titer was first confirmed (p=0.0205).

Figure 25:
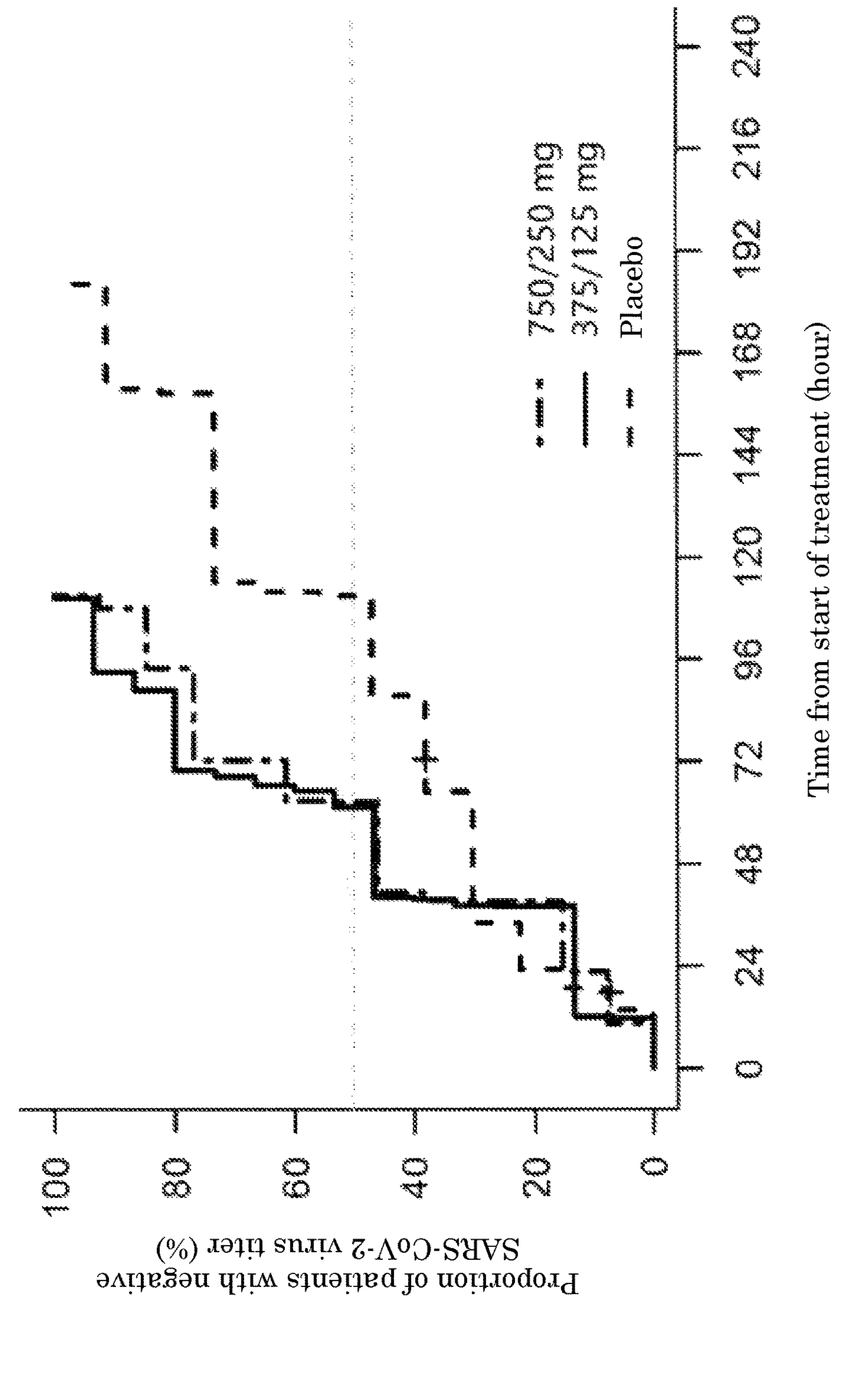
FIG. 25 shows time until a negative virus titer is first confirmed. The vertical axis represents a proportion of patients with a negative SARS-CoV-2 virus titer (unit: %). The horizontal axis represents time from the start of treatment (unit: hour).

In addition, as shown in FIG. 25, in the placebo group, the time until the virus titer of 50% of patients became negative was about 4.6 days after the start of treatment. On the other hand, in the 750/250 mg group and the 375/125 mg group, the time until the virus titer of 50% of patients became negative was about 2.6 days after the start of treatment. Thus, it was confirmed that the time until the virus titer of 50% of patients became negative first was reduced by about 2 days.

(2) Change From Baseline in COVID-19 12-Symptom Total Score at Each Time Point (Phase 2a Part)

A change from baseline in COVID-19 12-symptom total score at each time point is shown in FIG. 6.

Among 69 cases of Phase 2a Part, the results in 13 cases in the 375/125 mg group, 12 cases in the 750/250 mg group, and 14 cases in the placebo group for mild/moderate subjects are shown.

Figure 26:
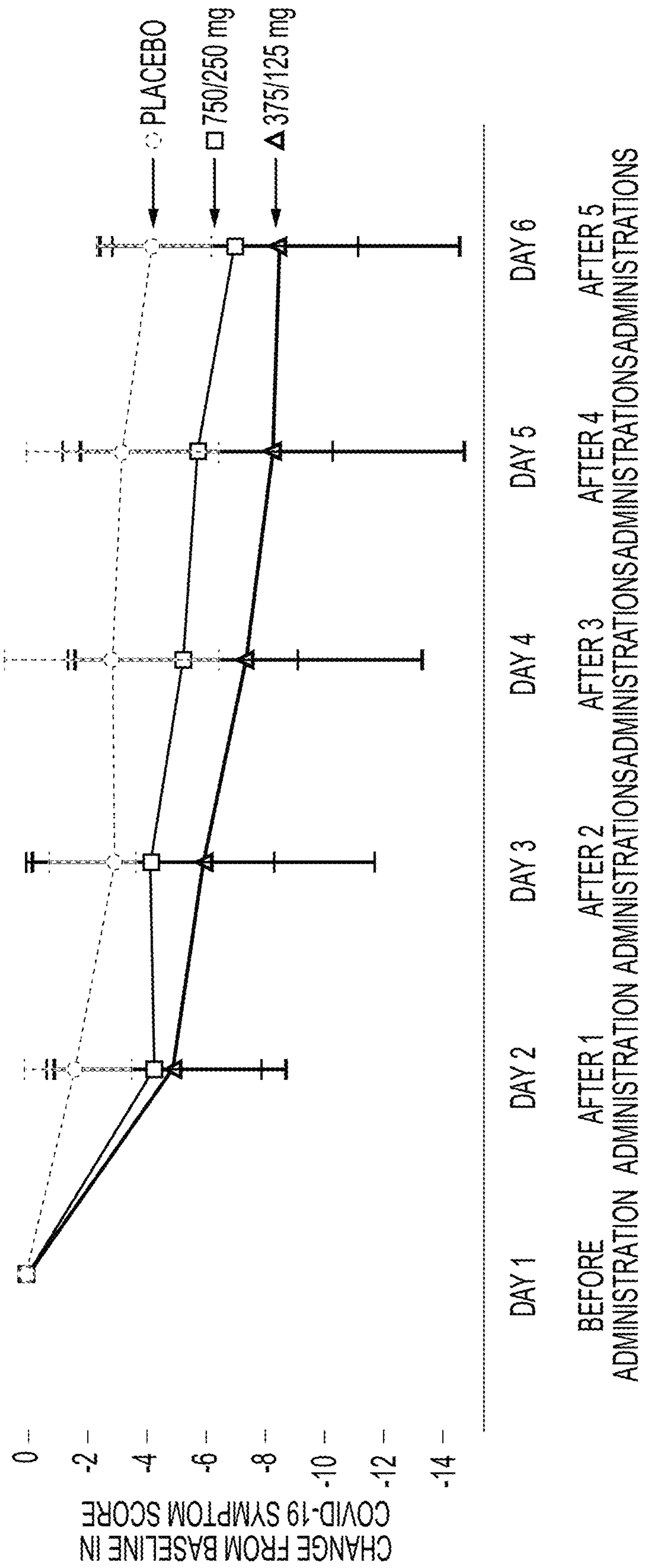
FIG. 26 shows a change from baseline in COVID-19 12-symptom total score at each time point. The vertical axis represents a change from baseline in COVID-19 12-symptom total score. The horizontal axis represents an evaluation time point.

As shown in FIG. 26, in the 375/125 mg group and the 750/250 mg group, there was a tendency for the COVID-19 12-symptom total score to numerically improve as compared to the placebo group at all time points on Day 2 (after 1 administration) and thereafter.

(3) Deterioration-Suppressing Effect (Phase 2a Part)

Among 69 cases of Phase 2a Part, for subjects with mild/moderate disease, a proportion of subjects whose Ordinal scale (ordinal scale to classify clinical severity in 8 stages, Table 14) score deteriorated to 3 or more for the first time at any time point after the start of administration is shown in Table 15.

TABLE 14

| 8-Point Ordinal Scale | Score |
|---|---|
| No symptoms observed | 0 |
| Having symptoms, and no trouble in daily life | 1 |
| Having symptoms, and trouble in daily life | 2 |
| Hospitalization or equivalent medical treatment is required | 3 |
| Subjects in need of hospitalization or equivalent medical treatment and oxygen administration (less than 5 L/min) | 4 |

TABLE 14-continued

| 8-Point Ordinal Scale | Score |
|---|---|
| Subjects in need of hospitalization or equivalent medical treatment and oxygen administration (5 L/min or more) | 5 |
| Subjects in need of hospitalization or equivalent medical treatment and ventilator | 6 |
| Death | 7 |

TABLE 15

| | 375/125 mg group | 750/250 mg group | Placebo group |
|---|---|---|---|
| Exacerbation rate | 0.0% | 0.0% | 14.3% |
| Number of exacerbations/number of cases to be analyzed | 0/13 | 0/12 | 2/14 |

As shown in Table 15, in the 375/125 mg group and the 750/250 mg group, cases in which Ordinal scale deteriorated to 3 or more for the first time after the start of administration were not confirmed.

Frequency of Adverse Events

In Phase 2a Part, there were no deaths, serious adverse events, or adverse events leading to discontinuation of administration.

The formulation of the present invention can be used for children who are 12 years old or older and adults.

Example 8

(Method for Producing Tablet)

Tablets containing the fumaric acid cocrystal Form I of the compound represented by Formula (VII) were produced.

The formulations per tablet are shown in the following table. The fumaric acid cocrystal Form I of the compound represented by Formula (VII), D-mannitol (manufactured by Roquette Freres), croscarmellose sodium (manufactured by DuPont), hydroxypropylcellulose (manufactured by Nippon Soda Co., Ltd.), light anhydrous silicic acid (manufactured by Cabot Corporation), and magnesium stearate (manufactured by Mallinckrodt Pharmaceuticals) were sieved with a 30-mesh sieve and mixed, and then granulated.

The granulated and milled granules, crystalline cellulose (manufactured by Asahi Kasei Corp.), and magnesium stearate (manufactured by Mallinckrodt Pharmaceuticals) or light anhydrous silicic acid (manufactured by Cabot Corporation) were added and mixed, and then compression-molded into a major axis of 15.4 mm×minor axis of 8 mm by a static compressor or a rotary tablet machine so as to obtain tablets having the following compositions.

TABLE 16

| Raw material name (mg) | Example 8A | Example 8B | Example 8C | Example 8D |
|---|---|---|---|---|
| Fumaric acid cocrystal Form I of compound represented by Formula (VII) | 304.6 | 304.6 | 304.6 | 304.6 |
| Content of compound represented by Formula (VII) | 250.0 | 250.0 | 250.0 | 250.0 |
| D-mannitol | 207.6 | 179.4 | 207.6 | 179.4 |
| Croscarmellose sodium | 62.6 | 62.6 | 62.6 | 62.6 |
| Hydroxypropyl cellulose | 34.4 | 62.6 | 34.4 | 62.6 |
| Light anhydrous silicic acid | 6.4 | 6.4 | 13.4 | 13.4 |
| Crystalline cellulose | 30 | 30 | 30 | 30 |
| Magnesium stearate | 18.4 | 18.4 | 39.4 | 39.4 |
| Total (mg) | 664 | 664 | 692 | 692 |

Test Example 7: Dissolution Test of Tablet (Dissolution Test Method)

For Examples 8A, 8B, 8C, and 8D, dissolution tests were performed by the Japanese Pharmacopoeia, Eighteenth Edition, Dissolution Test, Method 2nd (the first fluid for dissolution test containing a surfactant, paddle method, paddle rotation number: 50 rpm, result: average of two tablets).

(Test Results)

Faster dissolution were shown in all Examples.

Example 9

(Method for Producing Tablet)

Tablet containing the fumaric acid cocrystal Form I of the compound represented by Formula (VII) are produced.

The formulations per tablet are shown in the following table. The fumaric acid cocrystal Form I of the compound represented by Formula (VII), D-mannitol (manufactured by Roquette Frères), croscarmellose sodium (manufactured by DuPont), hydroxypropylcellulose (manufactured by Nippon Soda Co., Ltd.), light anhydrous silicic acid (manufactured by Cabot Corporation), and magnesium stearate (manufactured by Mallinckrodt Pharmaceuticals) are sieved with a 30-mesh sieve and mixed, and then granulated.

The granulated and milled granules, crystalline cellulose (manufactured by Asahi Kasei Corp.), and magnesium stearate (manufactured by Mallinckrodt Pharmaceuticals) or light anhydrous silicic acid (manufactured by Cabot Corporation) are added and mixed, and then compression-molded into a diameter of 5.0 mm or 5.5 mm by a static compressor or a rotary tablet machine so as to obtain tablets having the following compositions.

TABLE 17

| Raw material name (mg) | Example 9A | Example 9B | Example 9C | Example 9D |
|---|---|---|---|---|
| Fumaric acid cocrystal Form I of compound represented by Formula (I-B) | 30.46 | 30.46 | 30.46 | 30.46 |
| Content of compound represented by Formula (I-B) | 25.0 | 25.0 | 25.0 | 25.0 |
| D-mannitol | 20.76 | 17.94 | 20.76 | 17.94 |
| Croscarmellose sodium | 6.26 | 6.26 | 6.26 | 6.26 |
| Hydroxypropyl cellulose | 3.44 | 6.26 | 3.44 | 6.26 |
| Light anhydrous silicic acid | 0.64 | 0.64 | 1.34 | 1.34 |
| Crystalline cellulose | 3 | 3 | 3 | 3 |
| Magnesium stearate | 1.84 | 1.84 | 3.94 | 3.94 |
| Total (mg) | 66.4 | 66.4 | 69.2 | 69.2 |

Test Example 8: Dissolution Test of Tablet (Dissolution Test Method)

For two formulations of Example 9, dissolution tests were performed by the Japanese Pharmacopoeia, Eighteenth Edition, Dissolution Test, Method 2nd (the first fluid for dissolution test containing a surfactant, paddle method, paddle rotation number: 50 rpm, result: average of two tablets).

(Test Results)

Faster dissolutions were shown in all Examples.

The formulation of the present invention can also be used for children who are 6 years old or older and younger than 12 years old.

Example 10

(Method for Producing Granule)

Granules containing the fumaric acid cocrystal Form I of the compound represented by Formula (VII) are produced.

The formulations per granule are shown in the following table. The fumaric acid cocrystal Form I of the compound represented by Formula (VII), D-mannitol (manufactured by Roquette Freres), powdered reduced maltose starch syrup (maltitol, manufactured by Roquette Freres), croscarmellose sodium (manufactured by DuPont), hydroxypropylcellulose (manufactured by Nippon Soda Co., Ltd.), light anhydrous silicic acid (manufactured by Cabot Corporation), magnesium stearate (manufactured by Mallinckrodt Pharmaceuticals), and sucralose (manufactured by San-Ei Gen F.F.I., Inc.) are sieved with a 30-mesh sieve and mixed, and then granulated.

The granulated and milled granules, light anhydrous silicic acid (manufactured by Cabot Corporation), and sucralose (manufactured by San-Ei Gen F.F.I., Inc.) are added and mixed so as to obtain granules having the following compositions.

TABLE 18

| Raw material name (mg) | Example 10A | Example 10B | Example 10C | Example 10D |
|---|---|---|---|---|
| Fumaric acid cocrystal Form I of compound represented by Formula (VII) | 152.3 | 152.3 | 152.3 | 152.3 |
| Content of compound represented by Formula (VII) | 125.0 | 125.0 | 125.0 | 125.0 |
| D-mannitol | 1147.8 | 1072.7 | 1179.3 | 1104.2 |
| Powdered reduced maltose starch syrup (maltitol) | 226.5 | 226.5 | 226.5 | 226.5 |
| Croscarmellose sodium | 31.3 | 31.3 | 31.3 | 31.3 |
| Hydroxypropyl cellulose | 92.7 | 167.8 | 92.7 | 167.8 |
| Light anhydrous silicic acid | 40.7 | 40.7 | 40.7 | 40.7 |
| Magnesium stearate | 30.7 | 30.7 | 30.7 | 30.7 |
| Sucralose | 63 | 63 | 31.5 | 31.5 |
| Total (mg) | 1785 | 1785 | 1785 | 1785 |

Test Example 9: Dissolution Test of Granule (Dissolution Test Method)

For two formulations of Example 10, dissolution tests were performed by the Japanese Pharmacopoeia, Eighteenth Edition, Dissolution Test, Method 2nd (the first fluid for dissolution test containing a surfactant, paddle method, paddle rotation number: 50 rpm, result: average of two granules).

(Test Results)

Figure 27:
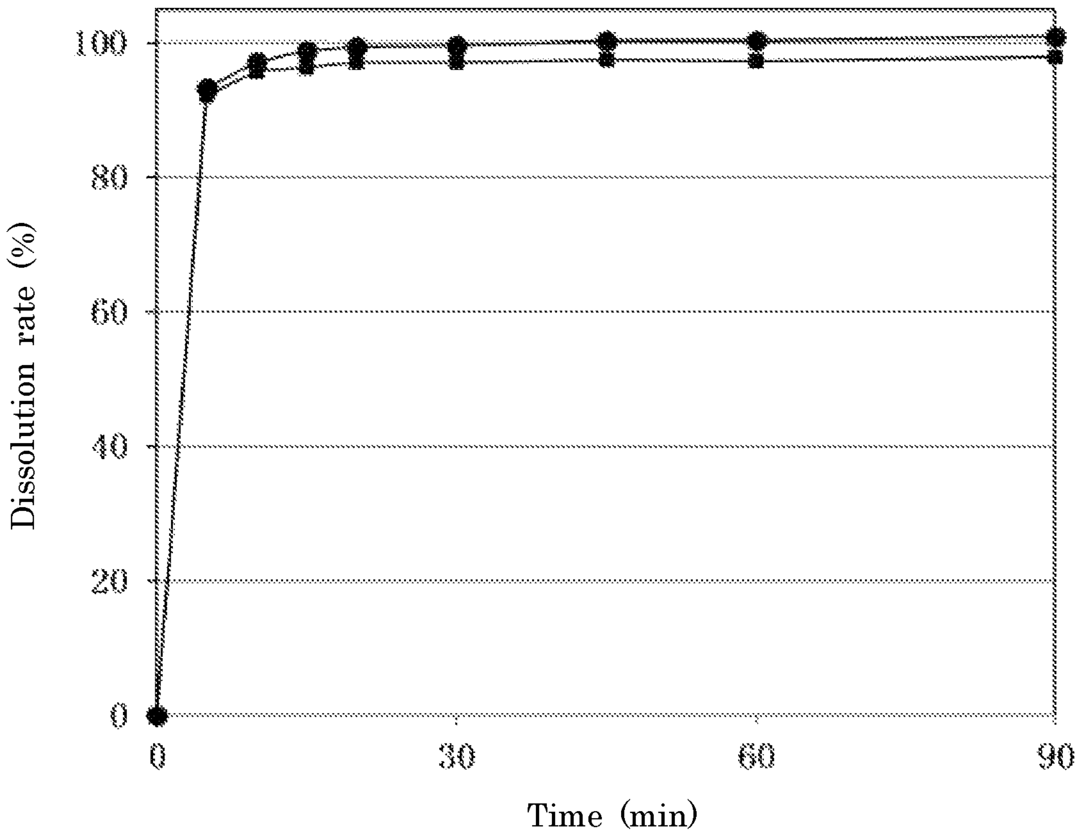
FIG. 27 shows a dissolution behavior of Example 10. The horizontal axis represents time (min) and the vertical axis represents a content-corrected dissolution rate (%).

The content-corrected dissolution test results are shown in FIG. 27. As a result, faster dissolutions were shown in all Examples.

Test Example 10: Temporal Stability Test of Granule

The results of confirming temporal stability of 2 formulations of Example 10 are shown.

a. Stability Test Method

The formulations of Example 10 were stored 1) in a closed DUMA bottle (plastic container, GERRESHEIMER) at 40° C. under 75% relative humidity for 3 weeks, or 2) in a closed DUMA bottle (plastic container, GERRESHEIMER) containing silica gel at 40° C. under 75% relative humidity for 3 weeks, or 3) in a closed DUMA bottle (plastic container, GERRESHEIMER) at 40° C. under 75% relative humidity for 1 month, or 4) in a closed DUMA bottle (plastic container, GERRESHEIMER) containing silica gel at 40° C. under 75% relative humidity for 1 month. Amount of related substances of the compound represented by Formula (VII) in the formulation of the present invention were measured.

(Method for Preparing Sample Solution)

(Measurement Method)

An amount of an related substance of the compound represented by Formula (VII) in the formulation of the present invention was measured with a solution chromatograph according to the following method and conditions.

Detector: ultraviolet absorptiometer (measurement wavelength: 222 nm)

Column: C18 column

Column temperature: constant temperature at near 40° C.

Mobile phase A: 0.01 mol/L ammonium formate solution,

Mobile phase B: acetonitrile

Regarding the mixing ratio of mobile phase A and mobile phase B, the mixing ratio of mobile phase B was gradually increased from 9:1 to 1:9, and the measurement was performed for 32 minutes.

Flow rate: 0.3 mL/min

For the amount of the related substance, the total peak area of chromatogram of HPLC chart was taken as 100%, and the ratio (%) of the amount was calculated.

b. Result

The results of the stability test are shown in Tables 19 and 20 below. The total amount of related substances in the formulation of Example 10 did not increase under any conditions, and were stable.

TABLE 19

| Packaging form | Storage conditions | Storage period | Total amount of related substances (%) |
|---|---|---|---|
| — | Initial | | 0.08 |
| closed DUMA bottle | 40° C./75% RH | 3 weeks | 0.09 |
| closed DUMA bottle containing silica gel | 40° C./75% RH | 3 weeks | 0.07 |

TABLE 20

| Packaging form | Storage conditions | Storage period | Total amount of related substances (%) |
|---|---|---|---|
| — | Initial | | 0.09 |
| closed DUMA bottle | 40° C./75% RH | 1 month | 0.08 |
| closed DUMA bottle containing silica gel | 40° C./75% RH | 1 month | 0.10 |

From the above, the formulations of the present invention have high stability against humidity and temperature.

The following formulation examples are merely examples and not intended to limit the scope of the invention.

The compound of the present invention can be administered as a pharmaceutical composition in any conventional route, particularly, in an enteral route, for example, orally, for example in the form of a tablet, a granule, or a capsule, or parenterally, for example, in the form of an injection or a suspension, locally, for example, in the form of a lotion, a gelling agent, an ointment, or a cream, or in the intranasal form or suppository form. The pharmaceutical composition comprising the compound of the present invention in the free form or in the form of a pharmaceutically acceptable salt can be produced together with at least one kind of pharmaceutically acceptable carrier or diluent by a conventional method such as a mixing, granulating, or coating method. For example, as a composition for oral, tablets, granules, and capsules containing excipients, disintegrants, binders, lubricants, etc. and an active ingredient, etc. can be used. Furthermore, as a composition for injection, solutions or suspensions can be used, and sterilization can be carried out, or preservatives, stabilizing agents, buffer agents, and the like may be contained.

(Formulation Example 1) Suspension

For example, water for injection was added to the active pharmaceutical ingredient, the compound represented by Formula (VII), to prepare a suspension.

(Formulation Example 2) Tablet

For example, D-mannitol and magnesium stearate were added as additives to the active pharmaceutical ingredient, the compound represented by Formula (VII), to prepare tablets.

(Formulation Example 3) Granule

For example, D-mannitol and magnesium stearate were added as additives to the active pharmaceutical ingredient, the compound represented by Formula (VII), to prepare granules.

INDUSTRIAL APPLICABILITY

The compound prepared by the manufacturing method according to the present invention has inhibitory activity against the coronavirus 3CL protease and is considered to be useful as a therapeutic agent and/or prophylactic agent for diseases or states that involve the coronavirus 3CL protease. The novel synthetic intermediate according to the present invention or its salt and the production method according to the present invention are useful in production of a pharmaceutical product.

The formulation of the present invention has inhibitory activity against the coronavirus 3CL protease and is considered to be useful as a therapeutic and/or prophylactic agent for diseases or states that involve the coronavirus 3CL protease.

Sequence Listing

```
                                 SEQUENCE LISTING


Sequence total quantity: 2
SEQ ID NO: 1             moltype = AA  length = 14
FEATURE                  Location/Qualifiers
source                   1..14
                         mol_type = protein
                         organism = synthetic construct
REGION                   1..14
                         note = Substrate Peptide
SEQUENCE: 1
KTSAVLQSGF RKME                                                      14

SEQ ID NO: 2             moltype = AA  length = 7
FEATURE                  Location/Qualifiers
REGION                   1..7
                         note = Internal Standard Peptide
source                   1..7
                         mol_type = protein
                         organism = synthetic construct
SEQUENCE: 2
KTSAVLQ                                                              7
```

The invention claimed is:

1. A solid formulation for oral administration, comprising a compound represented by Formula (VII):

(VII)

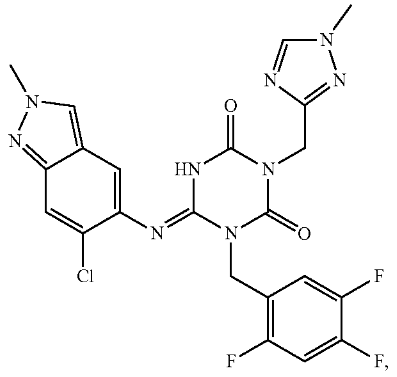

its pharmaceutically acceptable salt, or a complex thereof, as an active ingredient.

2. The solid formulation according to claim 1, further comprising a polymer.

3. The solid formulation according to claim 2, wherein the polymer is at least one selected from the group consisting of a cellulose-based polymer, an acrylic acid-based polymer, and a vinyl-based polymer.

4. The solid formulation according to claim 1, further comprising at least one additive selected from the group consisting of an excipient, a binder, a disintegrant, and a lubricant, and optionally further comprising at least one fluidizer.

5. The solid formulation according to claim 4, comprising at least one excipient, wherein the at least one excipient is mannitol.

6. The solid formulation according to claim 4, comprising at least one excipient, wherein the at least one excipient is crystalline cellulose.

7. The solid formulation according to claim 4, comprising at least one binder, wherein the at least one binder is hydroxypropylcellulose.

8. The solid formulation according to claim 4, comprising at least one disintegrant, wherein the at least one disintegrant is croscarmellose sodium.

9. The solid formulation according to claim 4, comprising at least one lubricant, wherein the at least one lubricant is magnesium stearate.

10. The solid formulation according to claim 4, comprising at least one fluidizer, wherein the at least one fluidizer is light anhydrous silicic acid.

11. The solid formulation according to claim 4, comprising mannitol, crystalline cellulose, hydroxypropylcellulose, croscarmellose sodium, magnesium stearate, and light anhydrous silicic acid.

12. The solid formulation according to claim 1, wherein the active ingredient is a complex of the compound represented by Formula (VII) and fumaric acid.

13. The solid formulation according to claim 12, wherein the complex is a cocrystal comprising the compound represented by Formula (VII) and fumaric acid in a molar ratio of 1:1.

14. The solid formulation according to claim 12, wherein the complex comprises a 50% particle size of 3.63 μm to 4.00 μm, and the complex comprises a 90% particle size of 10.80 μm to 10.98 μm.

15. The solid formulation according to claim 12, comprising 125 mg of the compound represented by Formula (VII).

16. The solid formulation according to claim 12, comprising 152.3 mg of the complex comprising the compound represented by Formula (VII) and fumaric acid in a molar ratio of 1:1.

* * * * *